US012648970B2

(12) United States Patent
Chabu et al.

(10) Patent No.: US 12,648,970 B2
(45) Date of Patent: Jun. 9, 2026

(54) COMPOSITIONS AND METHODS OF TREATMENT COMPRISING TUMOR-TARGETING BACTERIA AND CHEMOTHERAPY OR IMMUNOTHERAPY AGENT

(71) Applicant: The Curators of the University of Missouri, Columbia, MO (US)

(72) Inventors: Chiswili Yves Chabu, Columbia, MO (US); Bakul Dhagat, Columbia, MO (US); Robert Kazmierczak, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 447 days.

(21) Appl. No.: 18/042,070

(22) PCT Filed: Aug. 18, 2021

(86) PCT No.: PCT/US2021/046582
§ 371 (c)(1),
(2) Date: Feb. 17, 2023

(87) PCT Pub. No.: WO2022/040365
PCT Pub. Date: Feb. 24, 2022

(65) Prior Publication Data
US 2024/0009252 A1     Jan. 11, 2024

Related U.S. Application Data

(60) Provisional application No. 63/067,144, filed on Aug. 18, 2020.

(51) Int. Cl.
*A61K 35/74* (2015.01)
*A61K 9/00* (2006.01)
(Continued)

(52) U.S. Cl.
CPC ........... *A61K 35/74* (2013.01); *A61K 9/0019* (2013.01); *A61K 31/337* (2013.01);
(Continued)

(58) Field of Classification Search
CPC .... A61K 35/74; A61K 9/0019; A61K 31/337; A61K 31/404; A61K 31/4166;
(Continued)

(56) References Cited

U.S. PATENT DOCUMENTS 8,282,919 B2 * 10/2012 Eisenstark .............. A61P 35/00
435/252.8
8,916,372 B2 12/2014 Bereta et al.
(Continued)

FOREIGN PATENT DOCUMENTS

WO      2018/217237 A1     11/2018

OTHER PUBLICATIONS

Kazmierczak, Robert A. et al., Evaluations of CRC2631 toxicity, tumor colonization, and genetic stability in the TRAMP prostate cancer model, Oncotarget, 2020, vol. 11 (No. 44) pp. 3943-3958.
(Continued)

*Primary Examiner* — Robert B Mondesi
(74) *Attorney, Agent, or Firm* — Stinson LLP

(57) ABSTRACT

The present disclosure relates to a composition of a biologically pure isolate of the genus *Salmonella* comprising archival strain CRC1674, wherein the isolate further comprises a disruption of at least one gene selected from the group consisting of aroA, rfaH, and thyA and a chemotherapy agent, an immunotherapy agent, an androgen receptor antagonist, or a combination thereof. The present disclosure also relates to the method of use of this composition in treating cancer, particularly prostate cancer and pancreatic cancer.

20 Claims, 29 Drawing Sheets

Specification includes a Sequence Listing.

(51) Int. Cl.

| | |
|---|---|
| *A61K 31/337* | (2006.01) |
| *A61K 31/404* | (2006.01) |
| *A61K 31/4166* | (2006.01) |
| *A61K 39/00* | (2006.01) |
| *A61P 35/04* | (2006.01) |
| *C07K 16/28* | (2006.01) |

(52) U.S. Cl.
CPC ........ *A61K 31/404* (2013.01); *A61K 31/4166* (2013.01); *A61K 39/0011* (2013.01); *A61P 35/04* (2018.01); *C07K 16/2827* (2013.01); *A61K 2039/5156* (2013.01)

(58) Field of Classification Search
CPC ........ A61K 39/0011; A61K 2039/5156; A61K 2039/852; A61K 39/0275; A61K 39/3955; A61K 2039/585; A61K 2039/884; A61P 35/04; A61P 35/00; A61P 37/04; A61P 43/00; C07K 16/2827; C07K 14/255; C07K 2319/03; Y02A 50/30; C12N 1/205; C12N 9/1007; C12N 9/1092; C12N 15/74; C12R 2001/42; C12Y 201/01045; C12Y 205/01019
USPC ......................................................... 424/93.4
See application file for complete search history.

(56) References Cited

U.S. PATENT DOCUMENTS

| | | | |
|---|---|---|---|
| 9,795,641 B2 * | 10/2017 | Nardelli Haefliger ...................... A61K 45/06 |
| 9,861,621 B2 * | 1/2018 | Saha .................. C07K 16/2818 |
| 2009/0220459 A1 * | 9/2009 | Fensterle ............... A61P 37/06 435/253.1 |
| 2019/0070233 A1 | 3/2019 | Yeung et al. |

OTHER PUBLICATIONS

Liang, Kang et al., Genetically engineered Salmonella Typhimurium: Recent advances in cancer therapy, Cancer Letters 448 (2019) pp. 168-181.

Wang, Cheng-Zhi et al., Strains, Mechanism, and Perspective: *Salmonella*-Based Cancer Therapy, International Journal of Microbiology (2016) Article ID 5678702, 10 pages.

International Search Report and Written Opinion dated Dec. 21, 2021 relating to PCT Application No. PCT/US2021/046582, 11 pages.

* cited by examiner

Fig. 1A
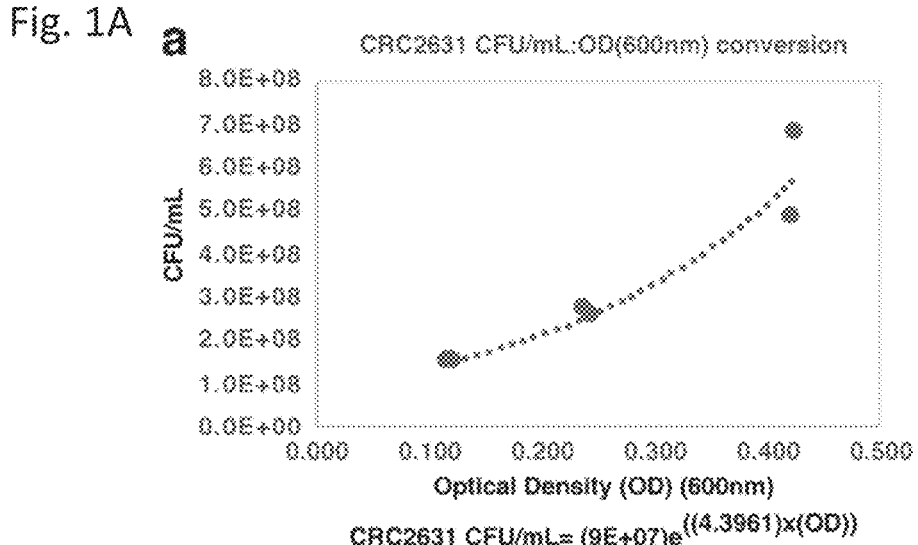
CRC2631 CFU/mL= (9E+07)e$^{((4.3961)x(OD))}$
Fig. 1B
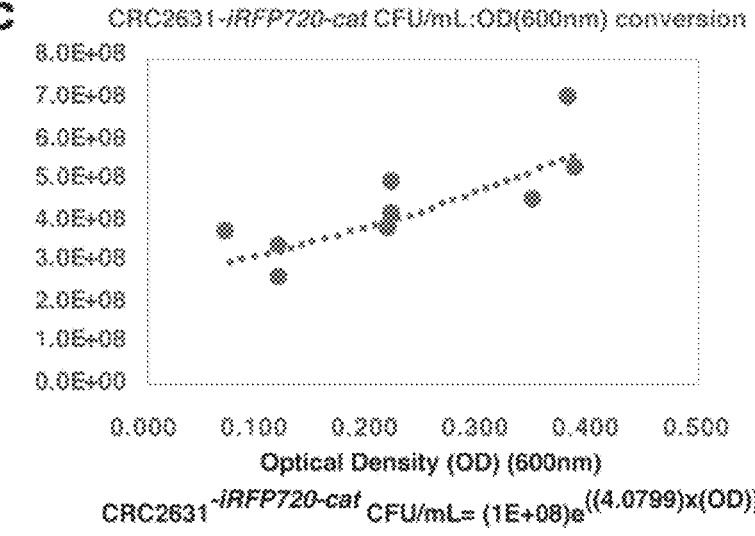
VNP20009 CFU/mL= (2E+08)e$^{((4.093)x(OD))}$
Fig. 1C
CRC2631$^{-iRFP720-cat}$ CFU/mL= (1E+08)e$^{((4.0799)x(OD))}$ a b e f NCI-H660 Cells

COMPOSITIONS AND METHODS OF TREATMENT COMPRISING TUMOR-TARGETING BACTERIA AND CHEMOTHERAPY OR IMMUNOTHERAPY AGENT

CROSS REFERENCE TO RELATED APPLICATIONS

This application is a Section 371 U.S. National Phase Application of PCT/US2021/046582, which claims priority to U.S. Provisional Application No. 63/067,144 filed on Aug. 18, 2020, which is hereby incorporated by reference in its entirety.

STATEMENT REGARDING FEDERALLY SPONSORED RESEARCH OR DEVELOPMENT

Not applicable.

INCORPORATION OF SEQUENCE LISTING

A paper copy of the Sequence Listing and a computer readable form of the Sequence Listing containing the file named "0800528.018501_ST25.txt", which is 6,438,095 bytes in size (as measured in MICROSOFT WINDOWS® EXPLORER), are provided herein and are herein incorporated by reference. This Sequence Listing consists of SEQ ID NOs: 1-6.

BACKGROUND

Prostate cancer (PC) is one of the leading causes of cancer death among men with the American Cancer Society's estimate of 31,620 deaths from prostate cancer for 2019. Chemotherapy and androgen deprivation therapy (ADT) represent the cornerstone treatments. However, these treatments are not specific and have broad off targeting effects at therapeutic dose (TD) leading to significant morbidities. Importantly, chemotherapy and ADT are ineffective against neuroendocrine prostate cancer (NEPC), a deadly PC subtype. In fact, ADT gives rise to treatment emergent NEPC, which rapidly metastasize and kill the patient. The medium survival benefit under current therapies is less than 5 months. The emergence of more potent ADT agents on the market will continue to increase NEPC incidences. In addition, the average cost for treatment over a patient's lifetime is estimated at ~$177,7041. In some cases, active surveillance and follow-up treatments over a period of years significantly increases treatment cost. There is a need for safer, durable, and cost competitive therapy alternatives.

Similar to NEPC, pancreatic cancer (PanC) incidence is on the rise. PanC is predicted to become the second most lethal cancer by 2030. This year alone, it is estimated that ~57,600 people will be diagnosed with PanC in the United States. PanC is largely asymptomatic in the early stages of the diseases. As such, only ~20% of patients are diagnosed early enough to qualify for curative surgery (pancreatectomy). Surgery is costly, causes significant morbidity, and substantially reduces quality of life for these patients. Further, over 75% of these patients will eventually relapse with local or distant tumors, suggesting that patients with seemingly local disease already have undetectable micrometastases, which underscores the inherent systemic nature of the disease. Patients presenting with distant metastatic disease, which accounts for over 70% of patients, are uncurable under the current standard of care. These patients are treated with chemotherapy (e.g. nab-paclitaxel, gemcitabine, FOLFIRINOX, and Irinotecan liposomes) that are considerably toxic and yet, lack durable survival benefit. Most patients quickly develop chemoresistance and die within a year of treatment initiation. There is an urgent clinical need for safe and potent therapeutics to achieve durable clinical benefits for patients.

Agents targeting immune checkpoint molecules (e.g. CTLA-4, PD-1/PDL-1, etc.) generate durable clinical benefits for cancer patients. However, these benefits have not been realized in prostate or pancreatic cancers due to the poor immunogenicity of these cancers.

Efforts to develop cancer-targeted therapeutics include the use of cancer-targeting bacteria to achieve cancer-specific cell killing. However, it has been a challenge to transition these bacteria-based approaches to the clinic due to a lack of a bacteria strain that is both safe and efficacious. Several bacterial strains have been developed, including the *Salmonella enterica* serovar *typhimurium* strain VNP20009, one of the most studied tumor-targeting strains. VNP20009 was first isolated in a genetic screen for hyperinvasion mutants using a library of mutant strains derived from ultraviolet and chemical mutagenesis of strain 14028. Additional targeted genetic mutations were previously introduced in the msb, lipid A, and purl loci to attenuate VNP20009 and generate purine auxotrophy, respectively. The safety and efficacy of VNP20009 were demonstrated in a wide range of preclinical animal cancer models, ultimately leading to clinical trials on metastatic melanoma or renal cell carcinoma patients. VNP20009 showed moderate toxicity but no antitumor effect in the aforementioned clinical studies, presumably because it was rapidly cleared by patients' immune system. These studies have provided significant clinical insights and have underscored the need for cancer-targeting biologics that are not only safe and efficacious, but also likely to translate to the clinic.

SUMMARY

This disclosure is directed to compositions, pharmaceutical compositions, and methods for treating certain conditions using a composition. The composition comprises a biologically pure isolate of the genus *Salmonella* comprising archival strain CRC1674, wherein the isolate further comprises a disruption of at least one gene selected from the group consisting of aroA, rfaH, and thyA and at least one of a chemotherapy agent, an immunotherapy agent, and an androgen receptor antagonist.

Further, the disclosure is directed to a composition comprising an archival *Salmonella enterica* serovar *Typhimurium* strain CRC2631 and at least one of a chemotherapy agent, an immunotherapy agent, and an androgen receptor antagonist.

Additionally, the disclosure describes a pharmaceutical composition comprising the compositions described herein and one or more pharmaceutically acceptable carriers or excipients.

The disclosure further describes methods for treating cancer in a patient in need thereof. Cancers can include solid tumors such as pancreatic cancer. The method comprises administering an effective amount of a biologically pure isolate of the genus *Salmonella* comprising archival strain CRC1674, wherein the isolate further comprises a disruption of at least one gene selected from the group consisting of aroA, rfaH, and thyA, and a chemotherapy agent, an immunotherapy agent, or a chemotherapy agent and an immunotherapy agent.

Also, the disclosure describes methods for treating prostate cancer in a patient in need thereof. The method comprises administering an effective amount of a biologically pure isolate of the genus *Salmonella* comprising archival strain CRC1674, wherein the isolate further comprises a disruption of at least one gene selected from the group consisting of aroA, rfaH, and thyA and a chemotherapy agent, an androgen receptor antagonist, or a chemotherapy agent and androgen receptor antagonist.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1A depicts an optical density conversion equation. Best fit curve equations (OD to viable cells/mL) were derived from CRC2631 independent clonal populations suspended in PBS at three different 600 nm optical densities (OD) after growth for 24 h in liquid culture and viable cells/mL determined by plating dilution series of each culture on plates containing appropriate selective antibiotics (see Example 1) and enumerated after 30 h incubation at 37° C.

FIG. 1B depicts an optical density conversion equation. Best fit curve equations (OD to viable cells/mL) were derived from VNP20009 independent clonal populations suspended in PBS at three different 600 nm optical densities (OD) after growth for 24 h in liquid culture and viable cells/mL determined by plating dilution series of each culture on plates containing appropriate selective antibiotics (see Example 1) and enumerated after 30 h incubation at 37° C.

FIG. 1C depicts an optical density conversion equation. Best fit curve equations (OD to viable cells/mL) were derived from CRC2631$^{iRFP720-cat}$ independent clonal populations suspended in PBS at three different 600 nm optical densities (OD) after growth for 24 h in liquid culture and viable cells/mL determined by plating dilution series of each culture on plates containing appropriate selective antibiotics (see Example 1) and enumerated after 30 h incubation at 37° C.

Figure 3A:
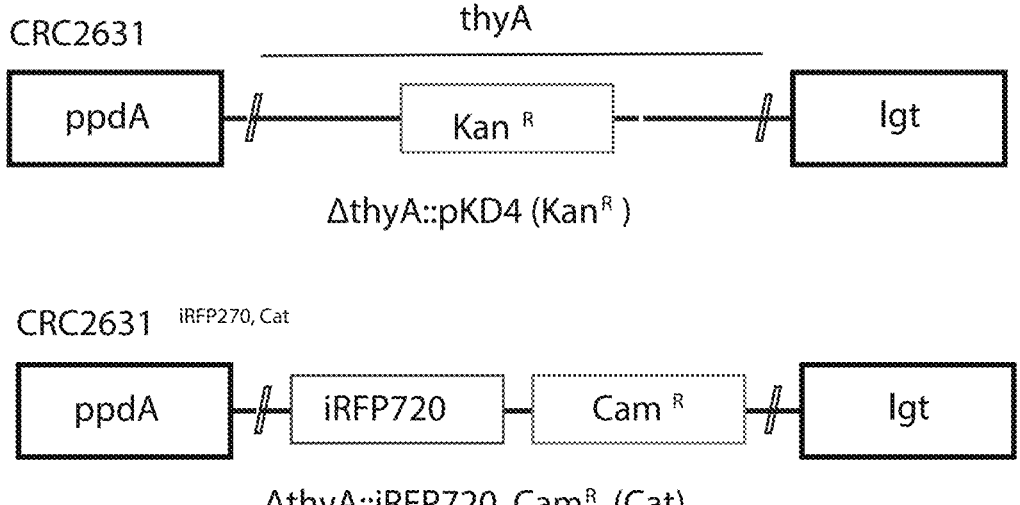
FIG. 3A depicts the re-engineering strategy used to create CRC2631$^{iRFP720-cat}$. The CRC2631 ΔthyA::Kan$^R$ region (top) was replaced with a gene that constitutively expresses iRFP720 and a chloramphenicol (Cam$^R$) (Cat) resistance cassette (bottom) for fluorescent detection in TRAMP models in vivo and selective recovery of CRC2631$^{iRFP720-cat}$ from tissue homogenates in biodistribution assays.
Figure 3B:
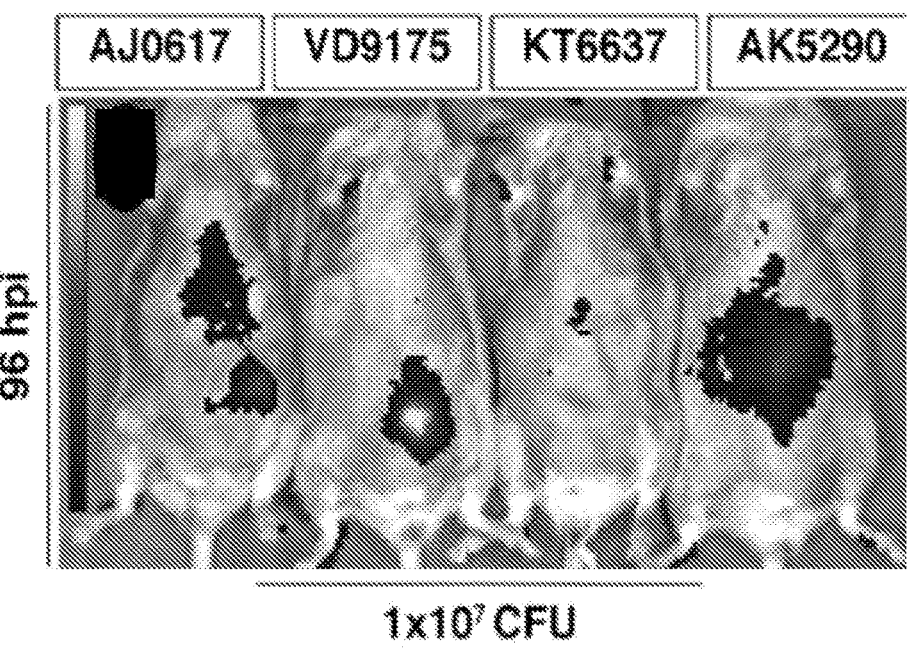
FIG. 3B depicts groups of three (N=3) male B6FVB TRAMP(+) mice (>25_weeks old) intravenously injected with single bolus doses of $1 \times 10^7$ CFU CRC2631$^{iRFP720-cat}$. In vivo fluorescence imaging of live B6FVB TRAMP(+) mice was performed 96 hours post injection to assess persistent tumor targeting capability of CRC2631$^{iRFP720-cat}$. Images were spectrally unmixed against negative controls (AK5290) to detect CRC2631$^{iRFP720-cat}$-associated iRFP720 signal. Dark areas indicate low CRC2631$^{iRFP720-cat}$-associated iRFP720 signal; light areas within dark areas indicate high CRC2631$^{iRFP720-cat}$-associated iRFP720 signal.
Figure 3C:
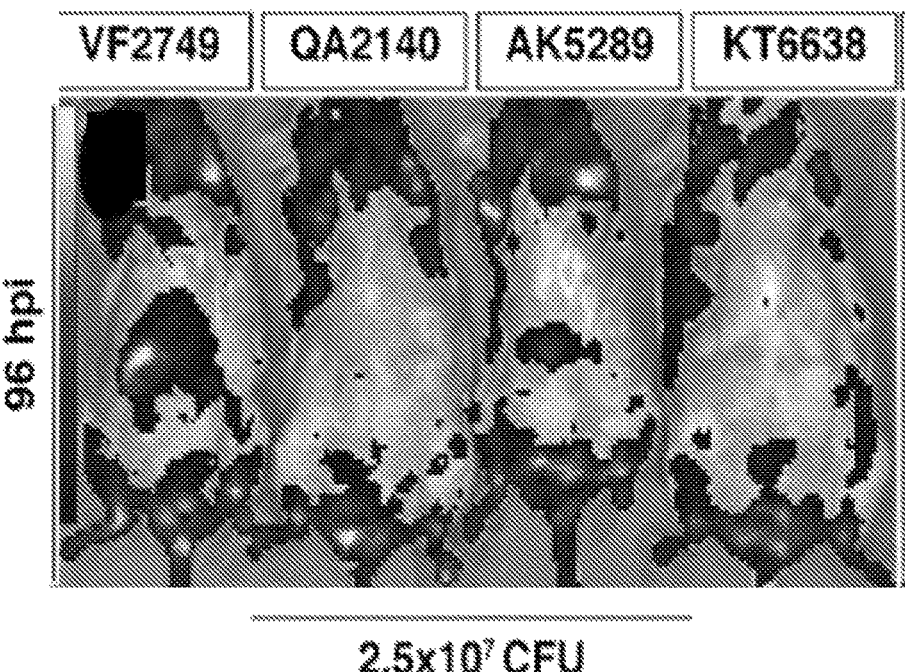
FIG. 3C depicts groups of three (N=3) male B6FVB TRAMP(+) mice (>25_weeks old) intravenously injected with single bolus doses of $2.5 \times 10^7$ CFU CRC2631$^{iRFP720-cat}$ to assay persistent targeting of primary and metastatic tumors at a higher dose. In vivo fluorescent scans of live B6FVB TRAMP(+) mice injected with CRC2631$^{iRFP720-cat}$ 96 hours post injection are shown. Images were spectrally unmixed against negative controls (KT6638) to detect CRC2631$^{iRFP720-cat}$-associated iRFP720 signal. Dark areas indicate low CRC2631$^{iRFP720-cat}$-associated iRFP720 signal; light areas within dark areas indicate high CRC2631$^{iRFP720-cat}$-associated iRFP720 signal.
Figures 3D, 3E:
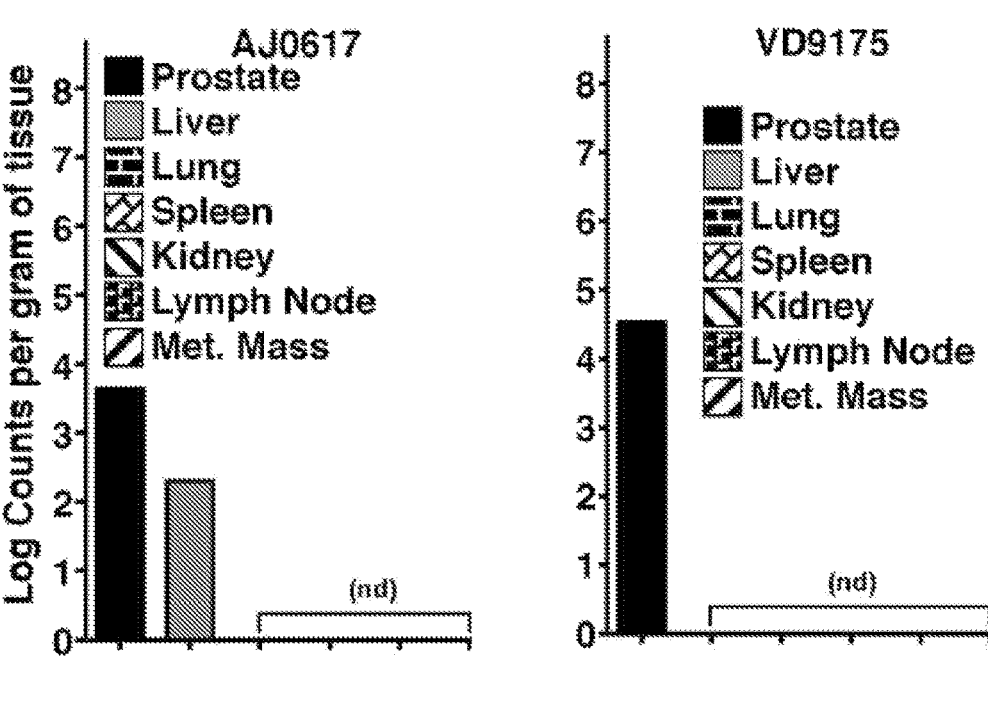
FIG. 3D depicts enumeration in AJ0617 of log CRC2631$^{iRFP720-cat}$ colony counts per gram of tissue at 190 hours post injection in the $1 \times 10^7$ CRC2631$^{iRFP720-cat}$ group. (nd) indicates tissues with no detectable CRC2631$^{iRFP720-cat}$/g tissue counts.

FIG. 3E depicts enumeration in VD9175 of log CRC2631$^{iRFP720-cat}$ colony counts per gram of tissue at 190 hours post injection in the $1 \times 10^7$ CRC2631$^{iRFP720-cat}$ group. (nd) indicates tissues with no detectable CRC2631$^{iRFP720-cat}$/g tissue counts.

Figure 3F:
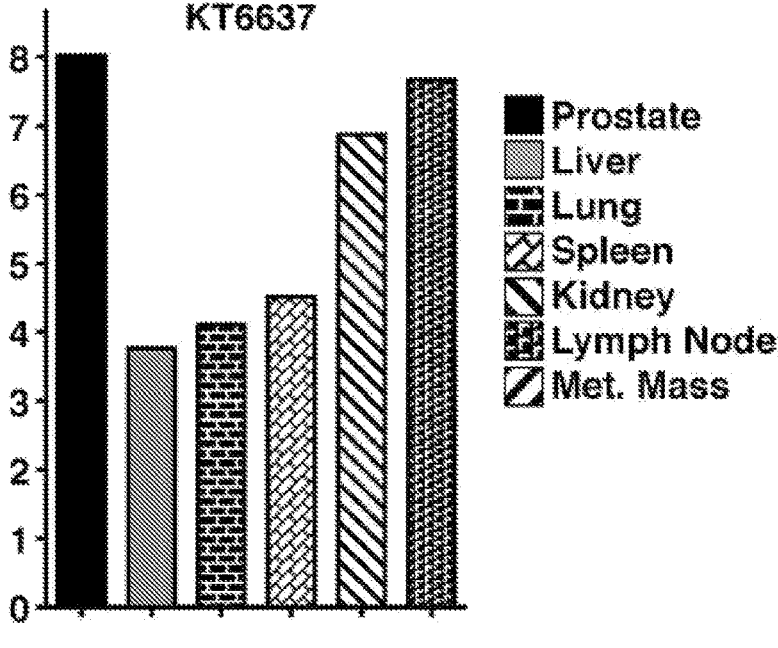

FIG. 3F depicts enumeration in KT6637 of log CRC2631$^{iRFP720-cat}$ colony counts per gram of tissue at 190 hours post injection in the $1 \times 10^7$ CRC2631$^{iRFP720-cat}$ group.

Figure 3G:
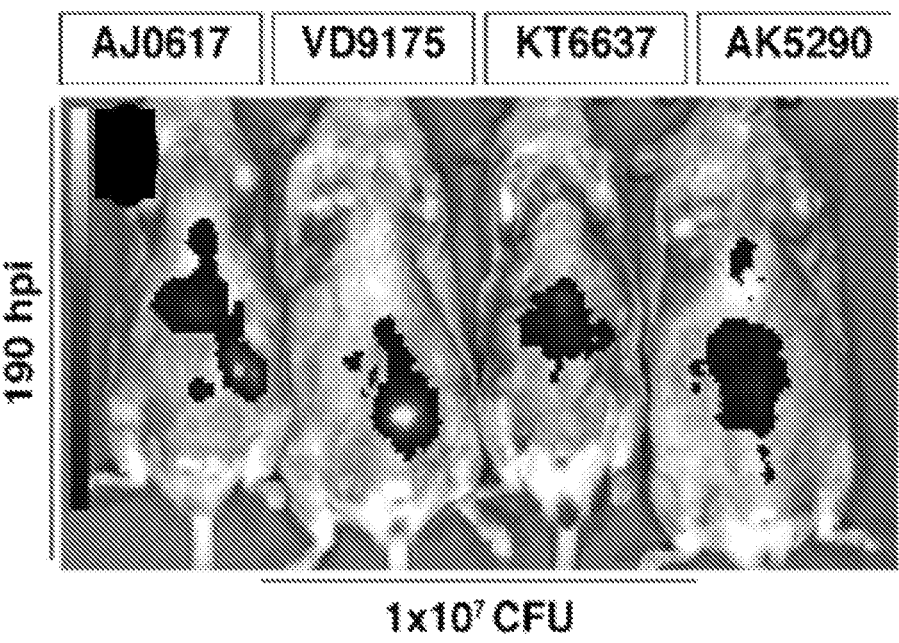

FIG. 3G depicts groups of three (N=3) male B6FVB TRAMP(+) mice (>25_weeks old) intravenously injected with single bolus doses of $1 \times 10^7$ CFU CRC2631$^{iRFP720-cat}$. In vivo fluorescence imaging of live B6FVB TRAMP(+) mice was performed 190 hours post injection to assess persistent tumor targeting capability of CRC2631$^{iRFP720-cat}$. Images were spectrally unmixed against negative controls (AK5290) to detect CRC2631$^{iRFP720-cat}$-associated iRFP720 signal. Dark areas indicate low CRC2631$^{iRFP720-cat}$-associated iRFP720 signal; light areas within dark areas indicate high CRC2631$^{iRFP720-cat}$-associated iRFP720 signal.

Figure 3H:
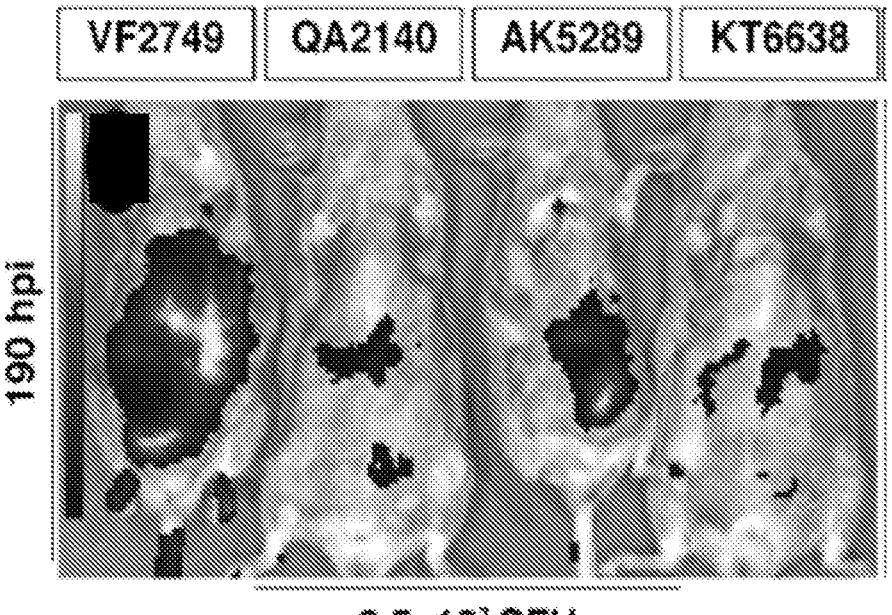

FIG. 3H depicts groups of three (N=3) male B6FVB TRAMP(+) mice (>25_weeks old) intravenously injected with single bolus doses of $2.5 \times 10^7$ CFU CRC2631$^{iRFP720-cat}$ to assay persistent targeting of primary and metastatic tumors at a higher dose. In vivo fluorescent scans of live B6FVB TRAMP(+) mice injected with CRC2631$^{iRFP720-cat}$ 190 hours post injection are shown. Images were spectrally unmixed against negative controls (KT6638) to detect CRC2631$^{iRFP720-cat}$-associated iRFP720 signal. Dark areas indicate low CRC2631$^{iRFP720-cat}$-associated iRFP720 signal; light areas within dark areas indicate high CRC2631$^{iRFP720-cat}$-associated iRFP720 signal.

Figure 3I:
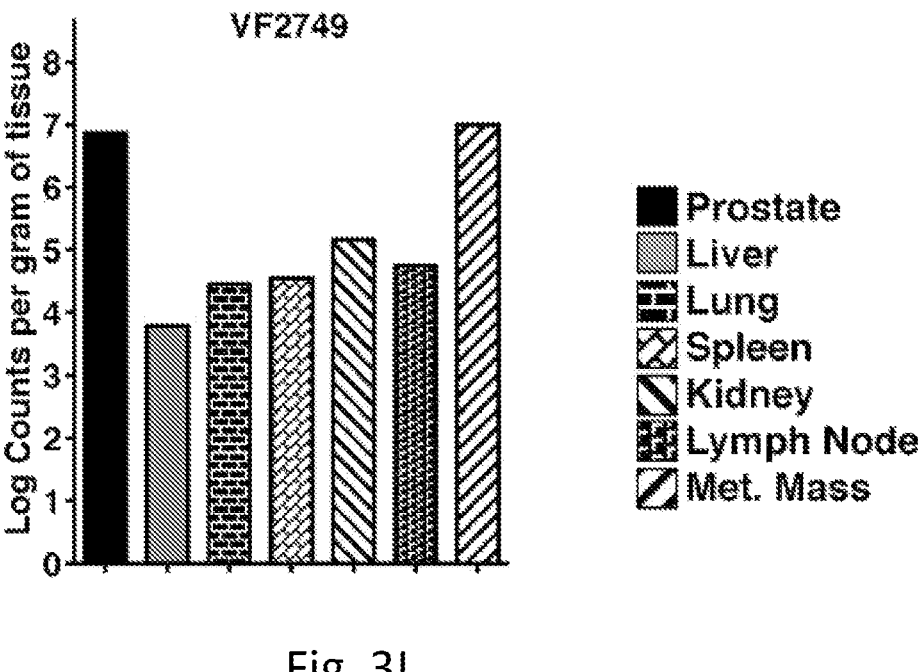

FIG. 3I depicts enumeration in VF2749 of log CRC2631$^{iRFP720-cat}$ colony counts per gram of tissue at 190 hours post injection in the $2.5 \times 10^7$ CRC2631$^{iRFP720-cat}$ group.

Figure 3J:
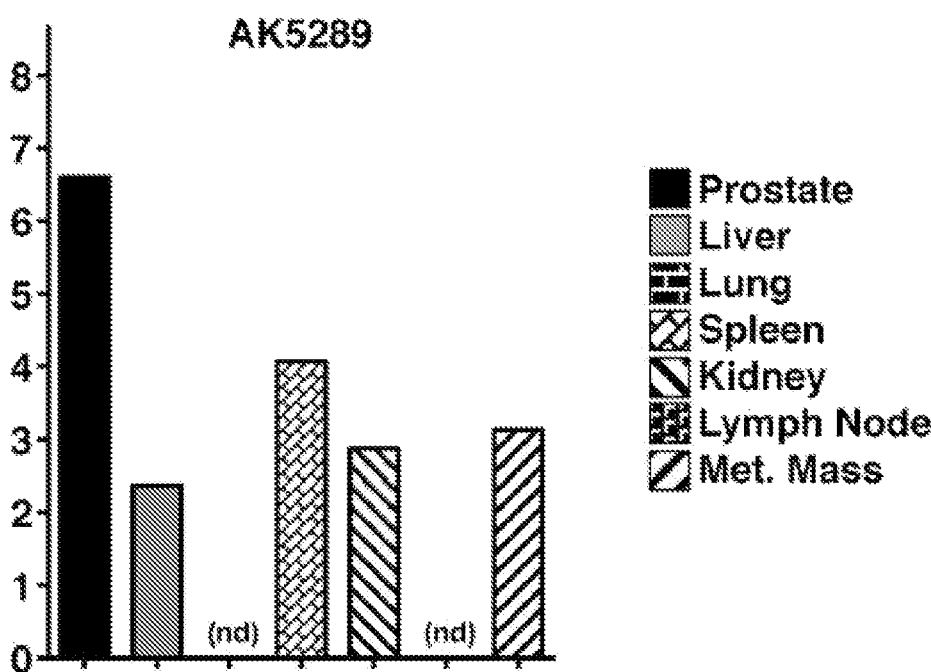

FIG. 3J depicts enumeration in AK5289 of log CRC2631$^{iRFP720-cat}$ colony counts per gram of tissue at 190 hours post injection in the $2.5 \times 10^7$ CRC2631$^{iRFP720-cat}$ group. (nd) indicates tissues with no detectable CRC2631$^{iRFP720-cat}$/g tissue counts.

Figures 3K, 3L, 3M, 3N, 3O, 3P, 3Q, 3R:
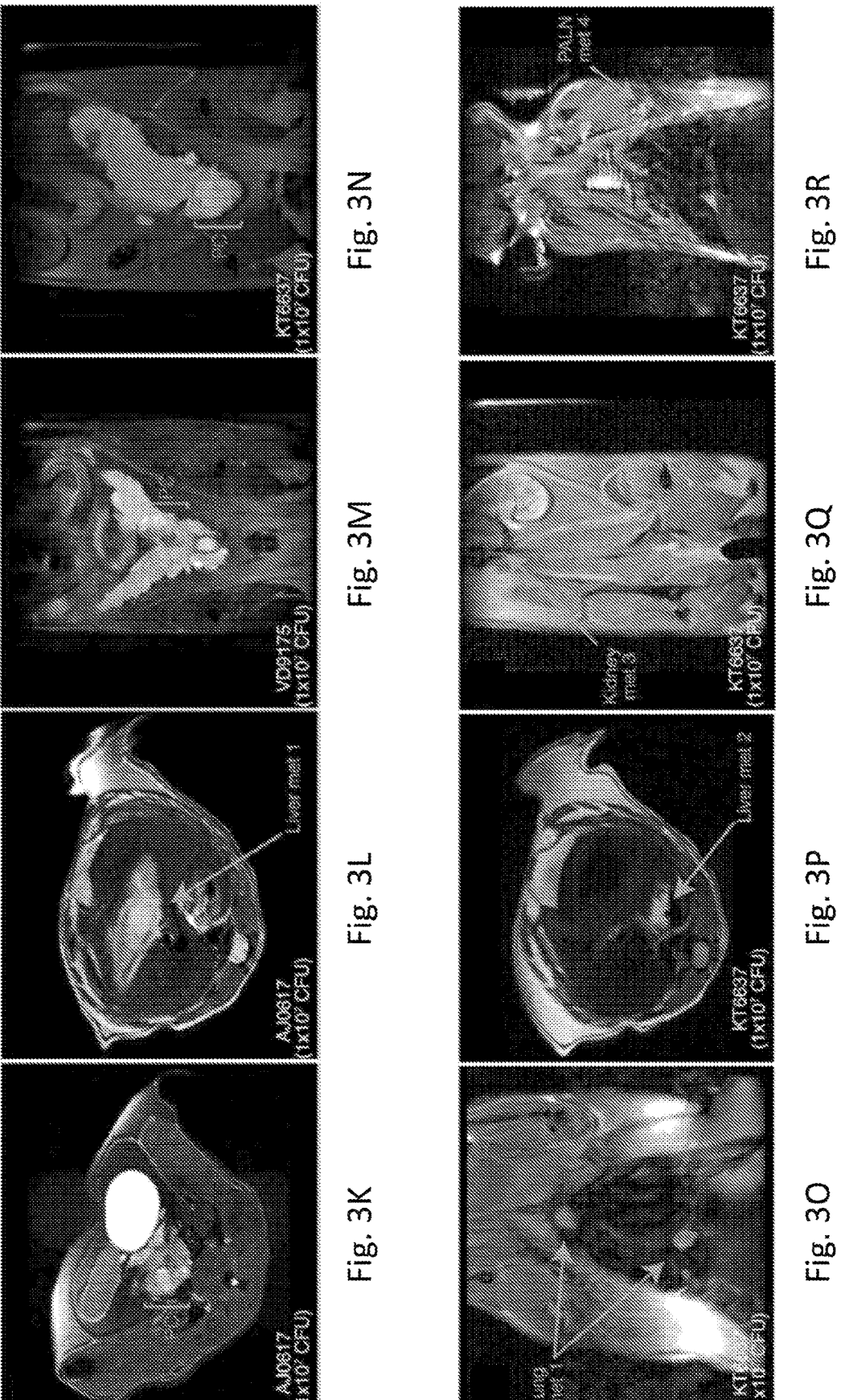

FIG. 3K depicts an MRI scan taken of AJ0617 to confirm primary prostate tumor (PC, brackets) in CRC2631$^{iRFP720-cat}$ colonized tissues identified by fluorescent scans and colony enumeration.

FIG. 3L depicts an MRI scan taken of AJ0617 to confirm metastatic (Met, regions indicated by arrows) tumor targeting tropism in CRC2631$^{iRFP720-cat}$ colonized liver tissue identified by fluorescent scans and colony enumeration.

FIG. 3M depicts an MRI scan taken of VD9175 to confirm primary prostate tumor (PC, brackets) in CRC2631$^{iRFP720-cat}$ colonized tissues identified by fluorescent scans and colony enumeration.

FIG. 3N depicts an MRI scan taken of KT6637 to confirm primary prostate tumor (PC, brackets) in CRC2631$^{iRFP720-cat}$ colonized tissues identified by fluorescent scans and colony enumeration.

FIG. 3O depicts an MRI scan taken of KT6637 to confirm metastatic (Met, regions indicated by arrows) tumor targeting tropism in CRC2631$^{iRFP720-cat}$ colonized lung tissue identified by fluorescent scans and colony enumeration.

FIG. 3P depicts an MRI scan taken of KT6637 to confirm metastatic (Met, regions indicated by arrows) tumor targeting tropism in CRC2631$^{iRFP720-cat}$ colonized liver tissue identified by fluorescent scans and colony enumeration.

FIG. 3Q depicts an MRI scan taken of KT6637 to confirm metastatic (Met, regions indicated by arrows) tumor targeting tropism in CRC2631$^{iRFP720-cat}$ colonized kidney tissue identified by fluorescent scans and colony enumeration.

FIG. 3R depicts an MRI scan taken of KT6637 to confirm metastatic (Met, regions indicated by arrows) tumor targeting tropism in CRC2631$^{iRFP720-cat}$ colonized PALN (proper axillary lymph node) tissue identified by fluorescent scans and colony enumeration.

Figures 3S, 3T, 3U, 3V:
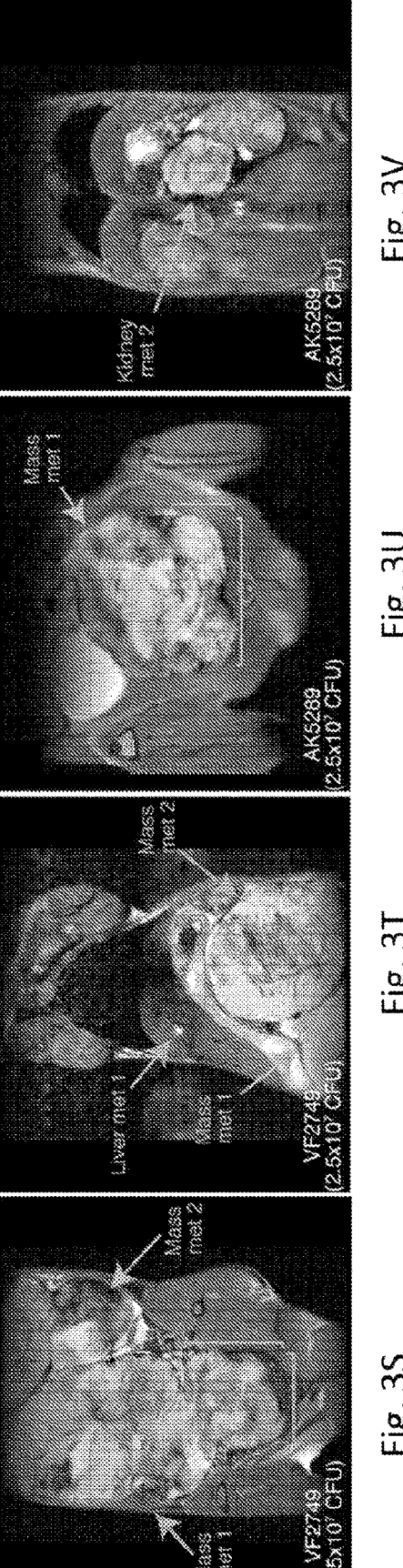

FIG. 3S depicts an MRI scan taken of VF2749 to confirm primary prostate tumor (brackets) and metastatic (Met, regions indicated by arrows) tumor targeting tropism in CRC2631$^{iRFP720-cat}$ colonized tissue identified by fluorescent scans and colony enumeration. Metastatic masses were attached to the right kidney in the upper peritoneal cavity.

FIG. 3T depicts an MRI scan taken of VF2749 to confirm metastatic (Met, regions indicated by arrows) tumor targeting tropism in CRC2631$^{iRFP720-cat}$ colonized tissue identified by fluorescent scans and colony enumeration. A liver metastasis is shown, and metastatic masses were attached to the right kidney in the upper peritoneal cavity.

FIG. 3U depicts an MRI scan taken of AK5289 to confirm primary prostate tumor (brackets) and metastatic (Met, regions indicated by arrows) tumor targeting tropism in CRC2631$^{iRFP720-cat}$ colonized tissue identified by fluorescent scans and colony enumeration. A metastatic mass was adjacent to the primary prostate tumor.

FIG. 3V depicts an MRI scan taken of AK5289 to confirm metastatic (Met, regions indicated by arrows) tumor targeting tropism in CRC2631$^{iRFP720-cat}$ colonized kidney tissue identified by fluorescent scans and colony enumeration.

Figure 4A:
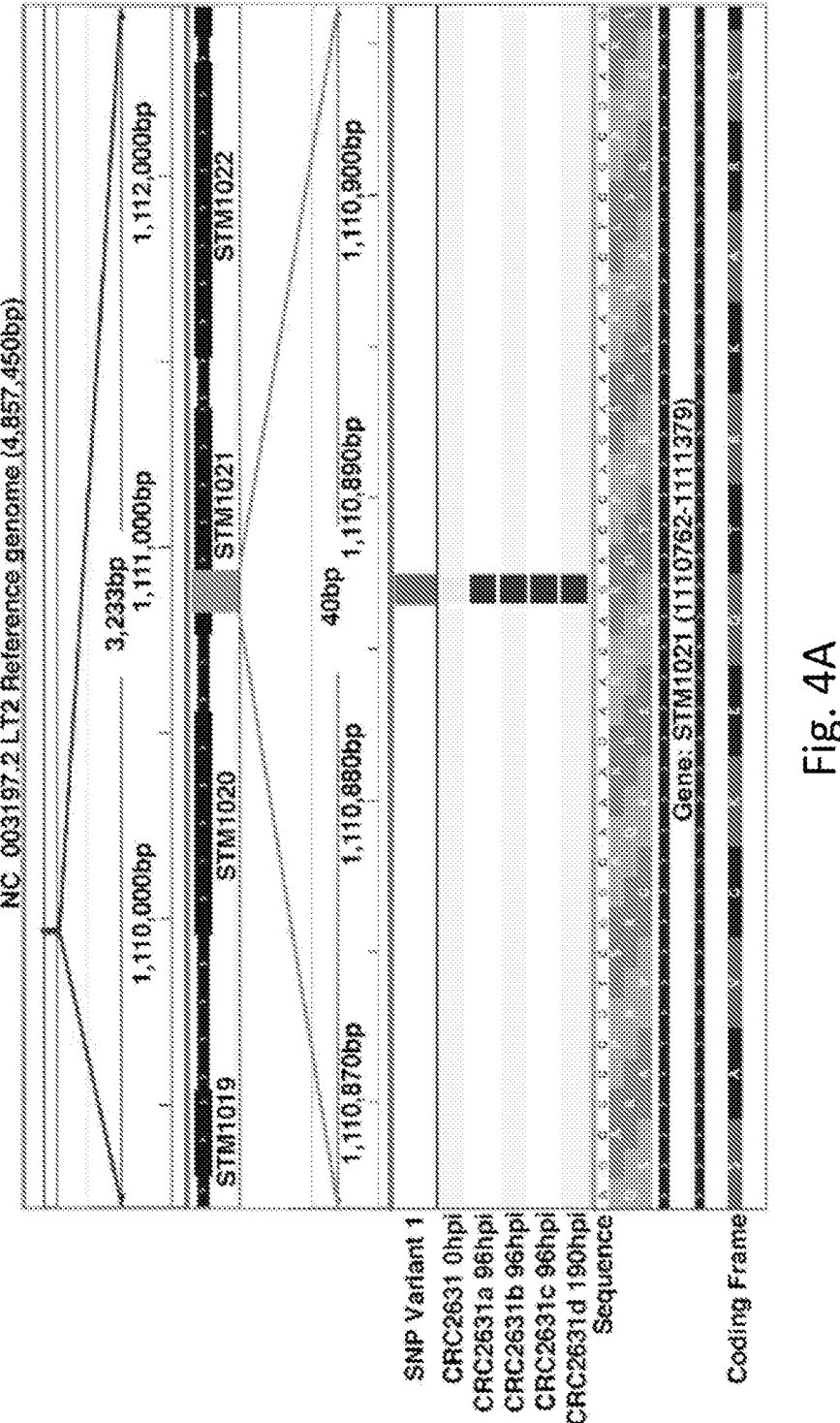

FIG. 4A depicts chromosomal DNA isolated from CRC2631 before injection and after passage through individual B6 TRAMP(+) mouse prostate tumor tissue samples at 96 hours post injection. Genomic DNA libraries were produced for all samples and sequenced using NovaSeq® 2×100 lane kit protocols (Illumina®). Graphical representations of single-nucleotide polymorphism (SNP) variant 1 using Integrative Genomics Viewer (v2.8.0). SNP locations are shown at three genomic resolutions; from top to bottom, the SNP location is indicated as a box at the cytologic overview, followed by increase in the genomic resolution to the local gene region showing labeled gene coding regions and the SNP location as a larger box, and finally followed by showing the SNP location as a box at nucleotide resolution as SNP Variant 1. Below, the SNP location is in light grey if no change was made from the CRC2631 parent, and the SNP location is in black if there was a SNP mutation from the CRC2631 parent.

Figure 4B:
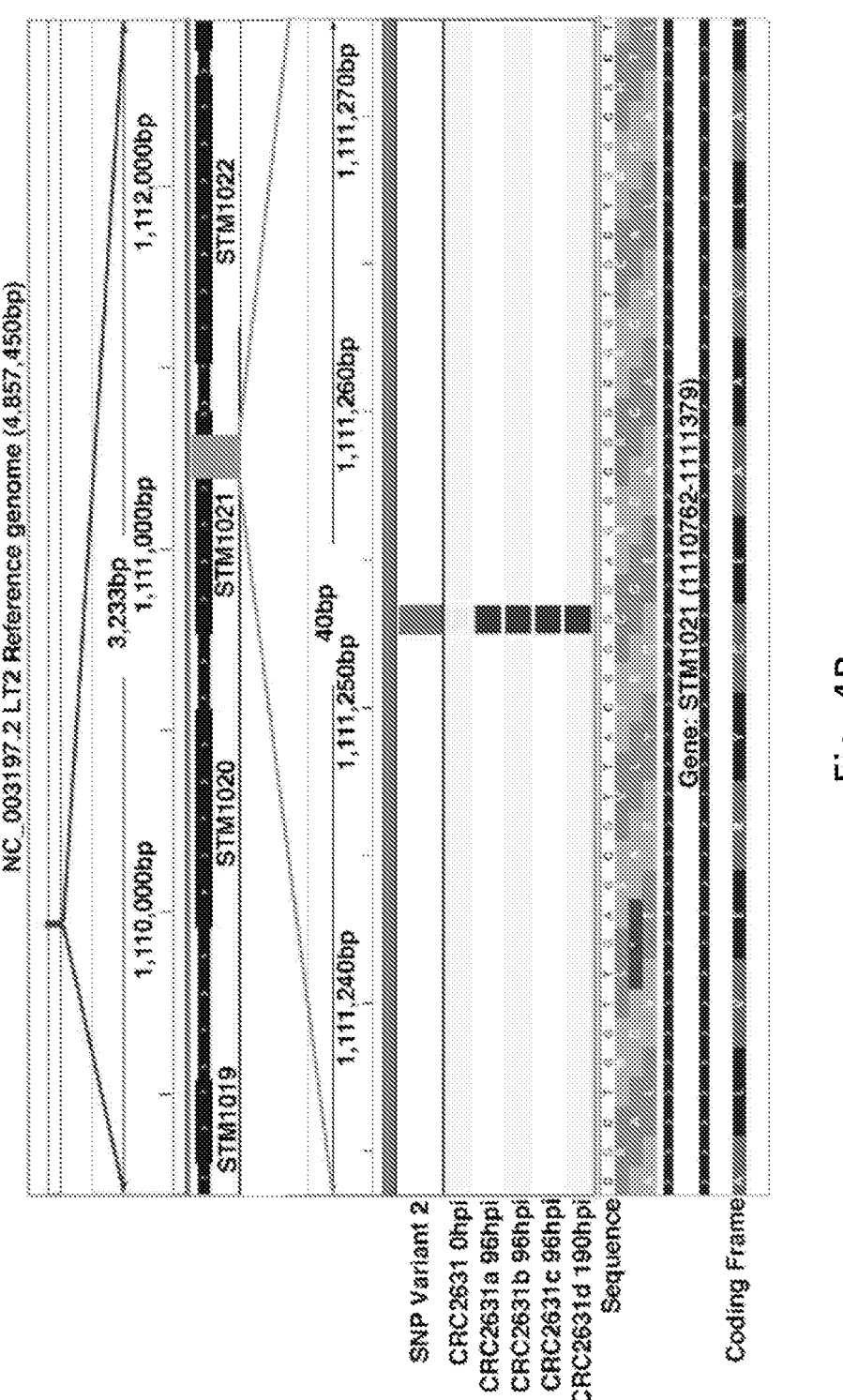

FIG. 4B depicts chromosomal DNA isolated from CRC2631 before injection and after passage through individual B6 TRAMP(+) mouse prostate tumor tissue samples at 96 hours post injection. Genomic DNA libraries were produced for all samples and sequenced using NovaSeq® 2×100 lane kit protocols (Illumina®). Graphical representations of SNP variant 2 using Integrative Genomics Viewer (v2.8.0). SNP locations are shown at three genomic resolutions; from top to bottom, the SNP location is indicated as a box at the cytologic overview, followed by increase in the genomic resolution to the local gene region showing labeled gene coding regions in and the SNP location as a larger box, and finally followed by showing the SNP location as a box at nucleotide resolution as SNP Variant 2. Below, the SNP location is in light grey if no change was made from the CRC2631 parent, and the SNP location is in black if there was a SNP mutation from the CRC2631 parent.

Figure 4C:
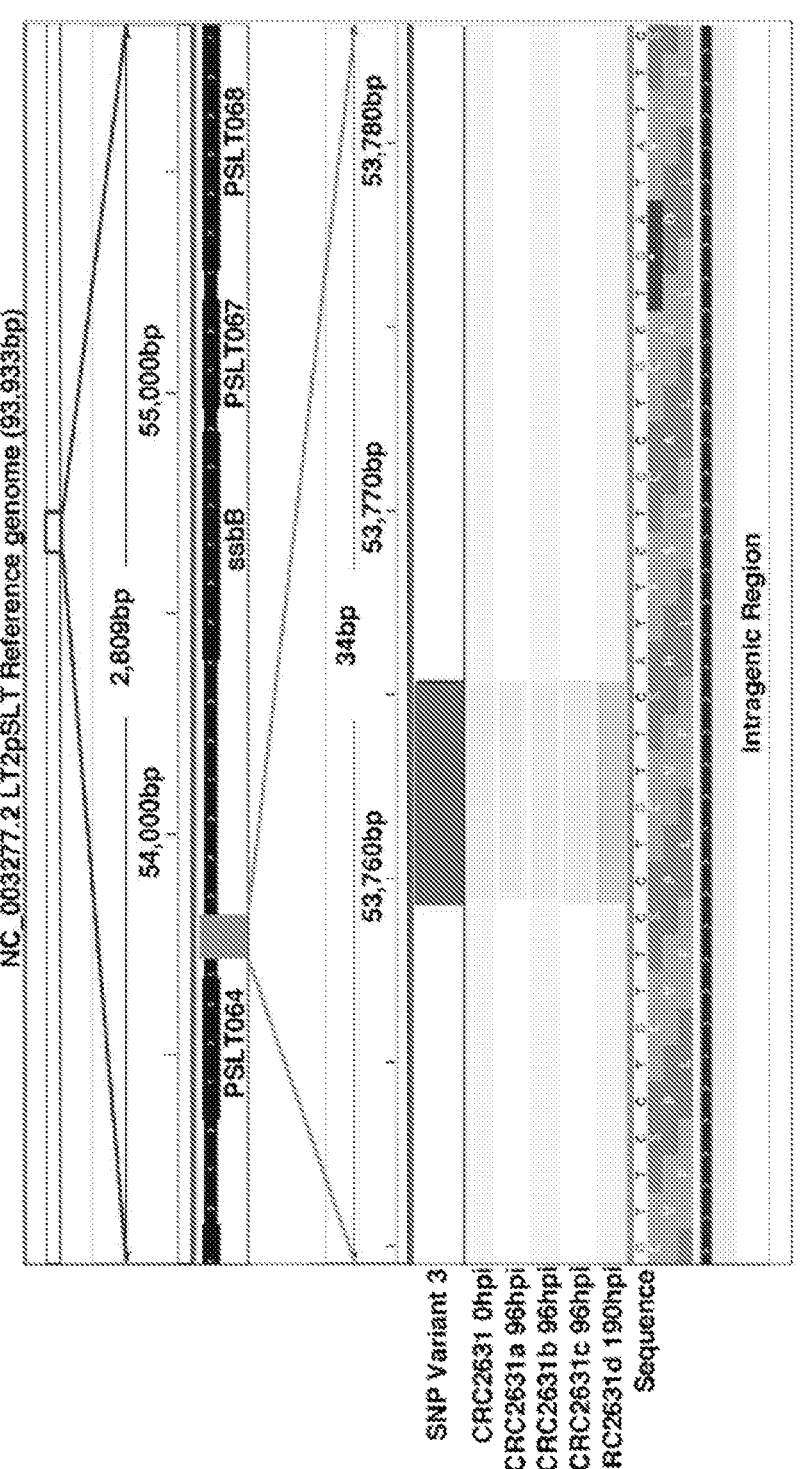

FIG. 4C depicts chromosomal DNA isolated from CRC2631 before injection and after passage through individual B6 TRAMP(+) mouse prostate tumor tissue samples at 190 hours post injection. Genomic DNA libraries were produced for all samples and sequenced using NovaSeq® 2×100 lane kit protocols (Illumina®). Graphical representations of SNP variant 3 using Integrative Genomics Viewer (v2.8.0). SNP locations are shown at three genomic resolutions; from top to bottom, the SNP location is indicated as a box at the cytologic overview, followed by increase in the genomic resolution to the local gene region showing labeled gene coding regions in and the SNP location as a larger box, and finally followed by showing the SNP location as a large rectangle at nucleotide resolution as SNP Variant 3. Below, the SNP location is in light grey if no change was made from the CRC2631 parent, and the lowest SNP location in dark grey indicates a deletion of 6 bp repeat in CRC2631 that reverts CRC2631d to original LT2 sequence.

Figure 4D:
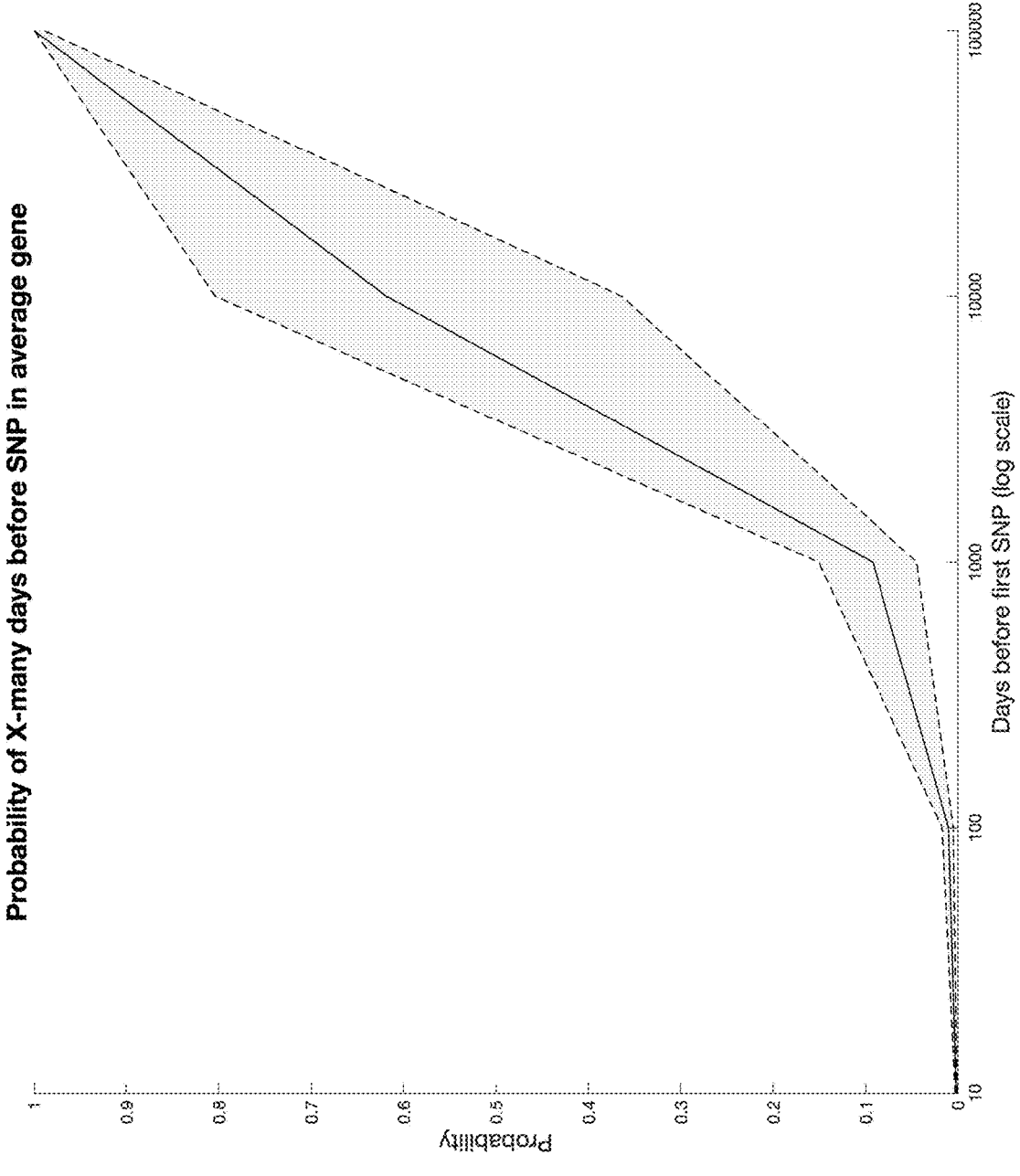

FIG. 4D depicts SNP prediction modeling that displays, on a logarithmic scale, the probability of an average gene in CRC2631 accumulating a first SNP after a given number of days in the tumor environment. These models predict that the risk of an average gene accumulating a first SNP after 10, 100, 1000, 10000 and 100000 days to be: 0.0015, 0.01, 0.0921, 0.6181, and 0.9999 respectively.

Figure 5A:
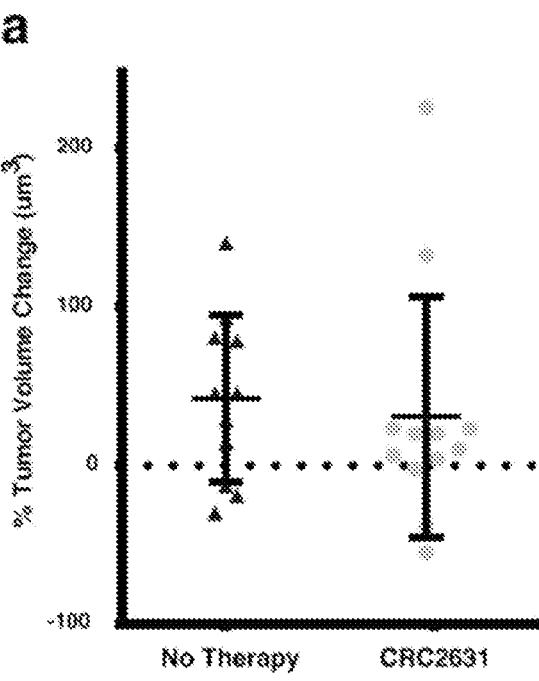

FIG. 5A depicts percentage change of ventral prostate tumor volume in 8-10-week-old B6FVB TRAMP(+) (N=12) male mice measured using MRI 5-7 days before and 21 days after starting four intravenous (IV) tail injections at three day intervals of 200 ul PBS (No therapy, left) or 2.5×10$^7$ CRC2631 (right).

Figure 5B:
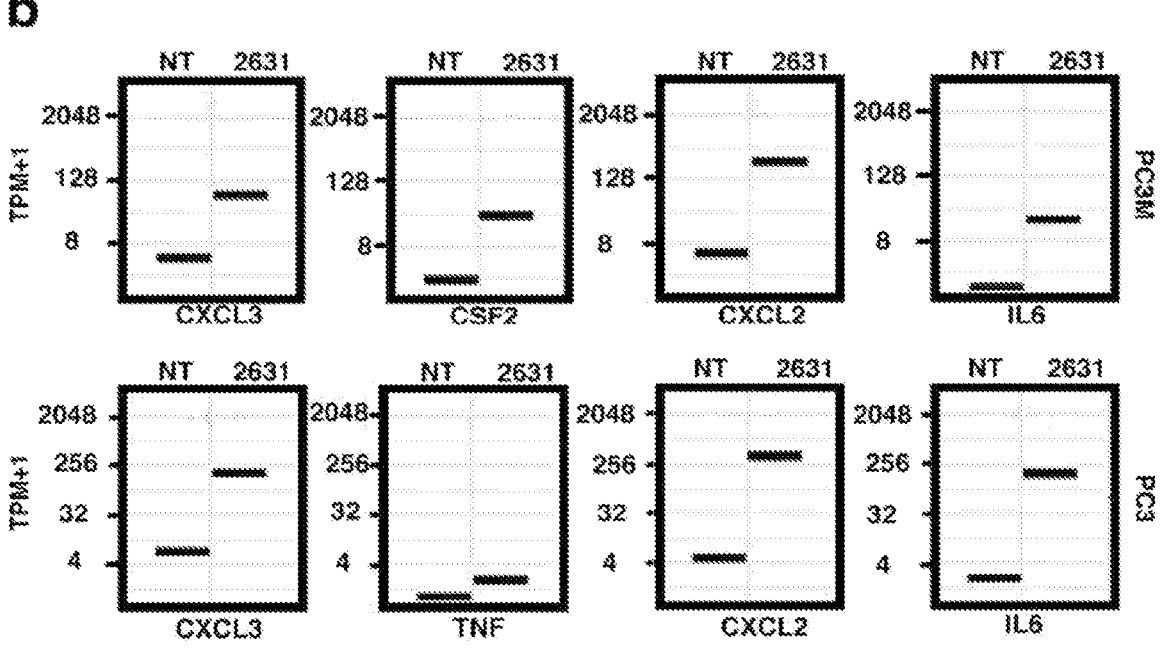

FIG. 5B depicts a box plot showing the expression of immune cytokines and chemokines in PC3M and PC3 human prostate cancer cell lines in response to CRC2631 treatment (N=3). TPM indicates gene transcripts per million. NT indicates No Treatment. 2631 indicates CRC2631 treated cells.

Figure 5C:
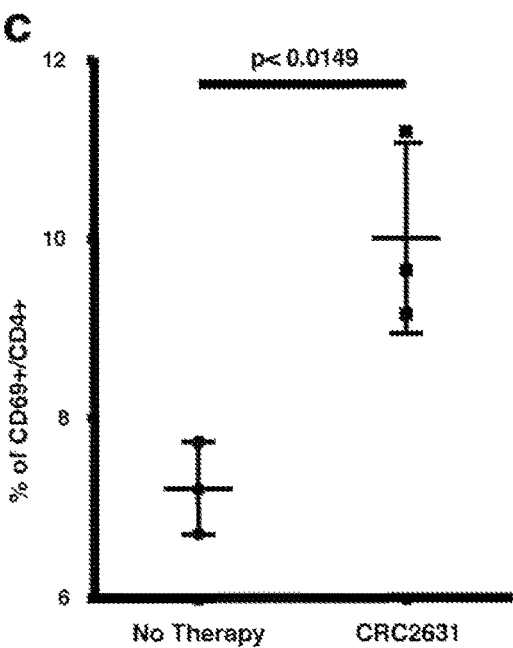

FIG. 5C depicts flow cytometric TILs profiling of metastasized lymph nodes extracted from PBS (no therapy) or CRC2631-treated B6FVB TRAMP(+) model group (N=3) to identify change in % of CD69+/CD4+fraction of cell population between no therapy and CRC2631-treated group. Student's t test analyses measured significance.

Figure 5D:
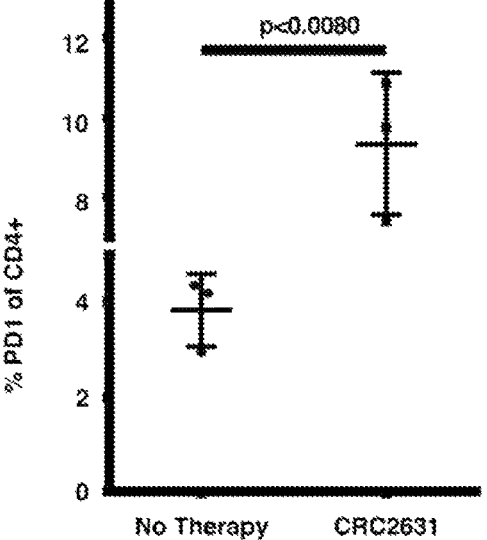

FIG. 5D depicts flow cytometric TILs profiling of metastasized lymph nodes extracted from PBS (no therapy) or CRC2631-treated B6FVB TRAMP(+) model group (N=3) to identify % PD1 expressing cells of CD4+ cell population. Student's t test analyses measured significance.

Figure 5E:
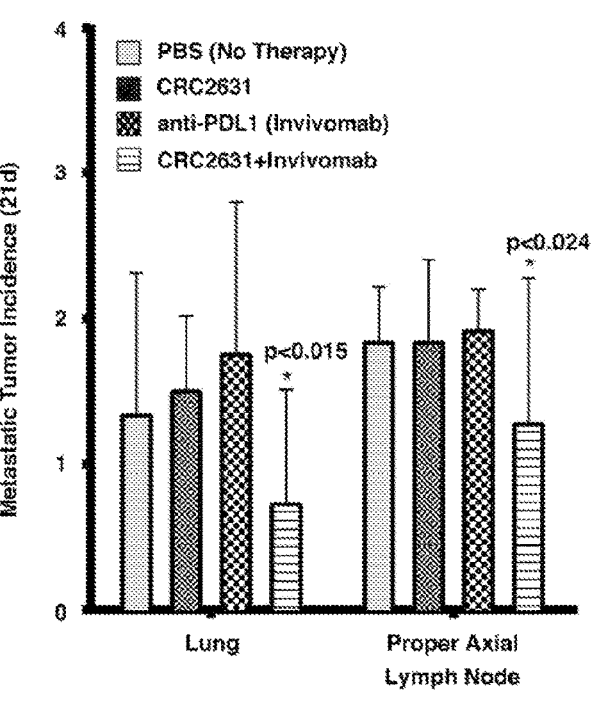

FIG. 5E depicts a comparison of metastasis incidence in lymph nodes and lung across treatment groups. Groups (N=12) of male B6FVB TRAMP(+) mice (8-10 weeks old) were IV injected with either PBS, 2.5×10$^7$ CRC2631, 0.5 mg of anti-mouse PDL1 antibody (Invivomab®), or CRC2631 and Invivomab® combination every three days for a total of four infusions. Post-treatment lung and proper axial lymph node MRI images taken 21 days after start of therapy were used to count and compare metastasis incidence across groups which were compared against PBS (control) and to determine significance using Student's t test.

Figure 5F:
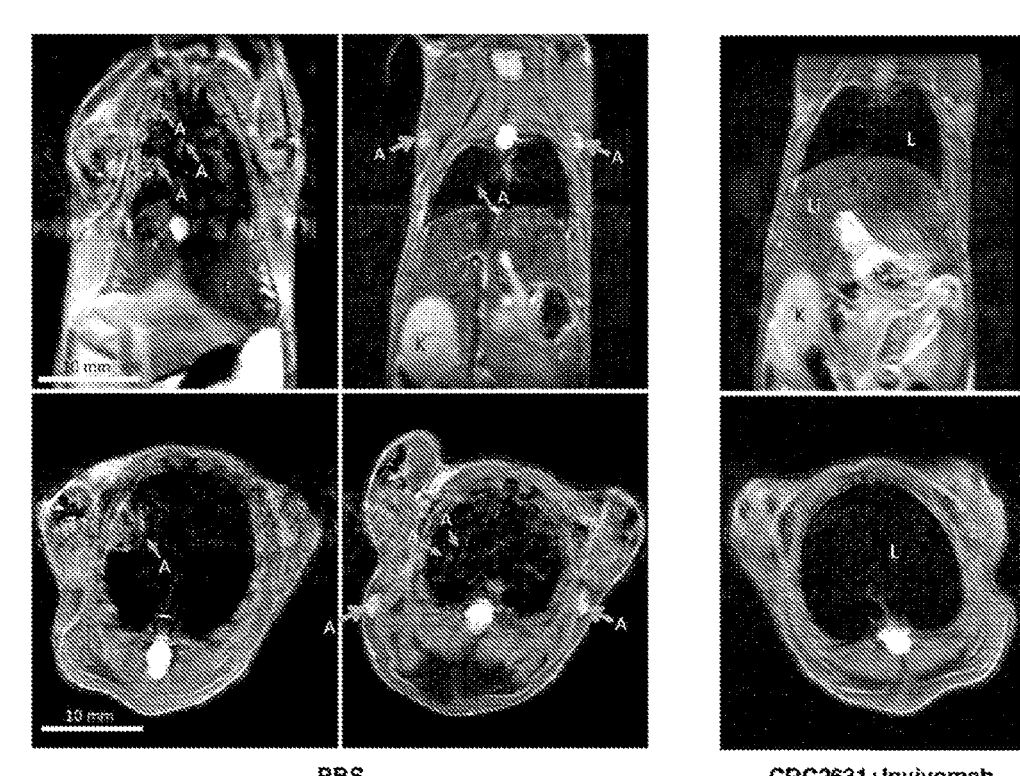

FIG. 5F depicts a comparison of metastasis incidence in lymph nodes and lung across treatment groups. Representative in vivo MRI images of TRAMP mouse model treated with PBS (control) or CRC2631 and Invivomab® combination. Control group showed more extensive lung tumors and proper axial lymph node metastases. The CRC2631-

Invivomab® combination therapy decreased the incidence of lung tumors and proper axial lymph node metastases. "A" indicates lung or lymph node metastasis. "L" indicates lungs, "Li" indicates liver, and "K" indicates kidney.

Figure 6:
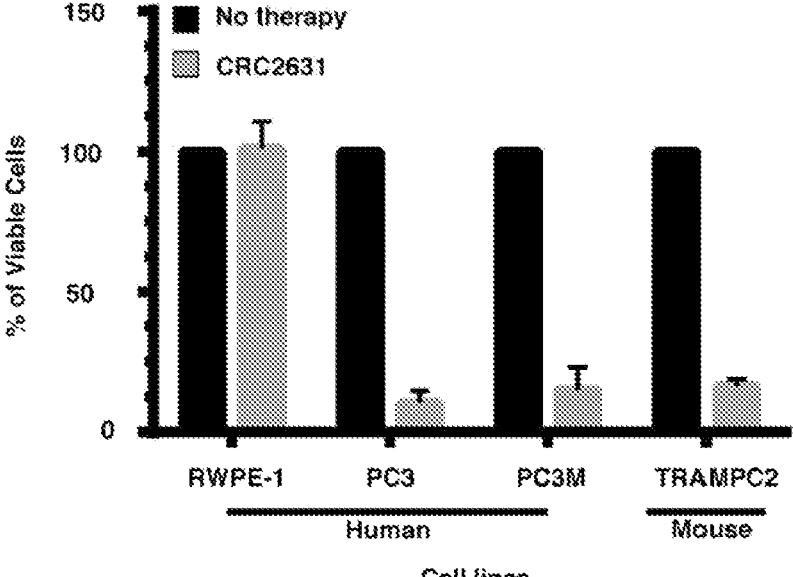

FIG. 6 depicts how CRC2631 specifically targets human and mouse prostate cancer cells. Human benign prostate (RWPE-1), prostate cancer and murine cancer cells ($10^4$) were treated with $10^4$ CFU of CRC2631 for 4 h at 37° C. and then washed. Cell viability was assessed using an MTT assay. Results represent the mean±SD of three trials performed in triplicates.

Figure 7A:
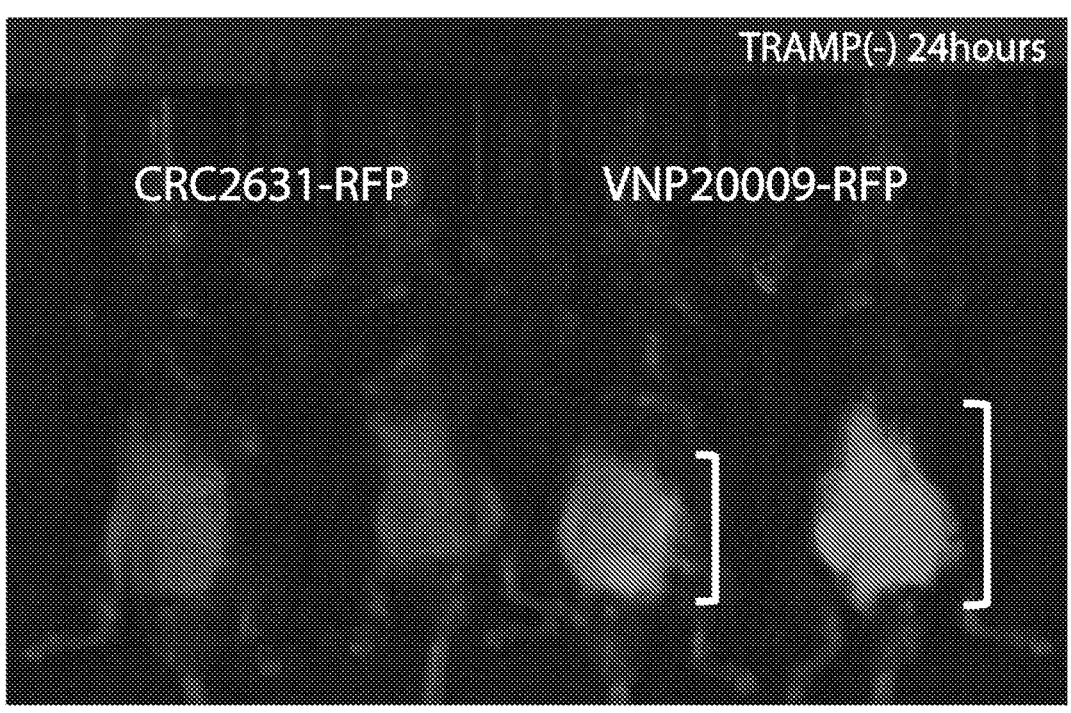

FIG. 7A depicts qualitative localization and persistence of CRC2631 and VNP20009 expressing mCherry red fluorescent protein (RFP) in B6 TRAMP(–) mice without primary prostate tumors. $1×10^6$ of each strain was administered interperitoneally and in vivo fluorescence scanning to detect mCherry RFP was performed at 24 hours post injection (hpi). Staining shows CRC2631- or VNP20009-associated unmixed mCherry signal (bracketed) or tissue autofluorescence. In contrast to the unspecific VNP20009 mCherry signal spread throughout the mouse abdomen, CRC2631 mCherry does not persist after 24 hours in B6 TRAMP(–) mice without primary prostate tumors.

Figure 7B:
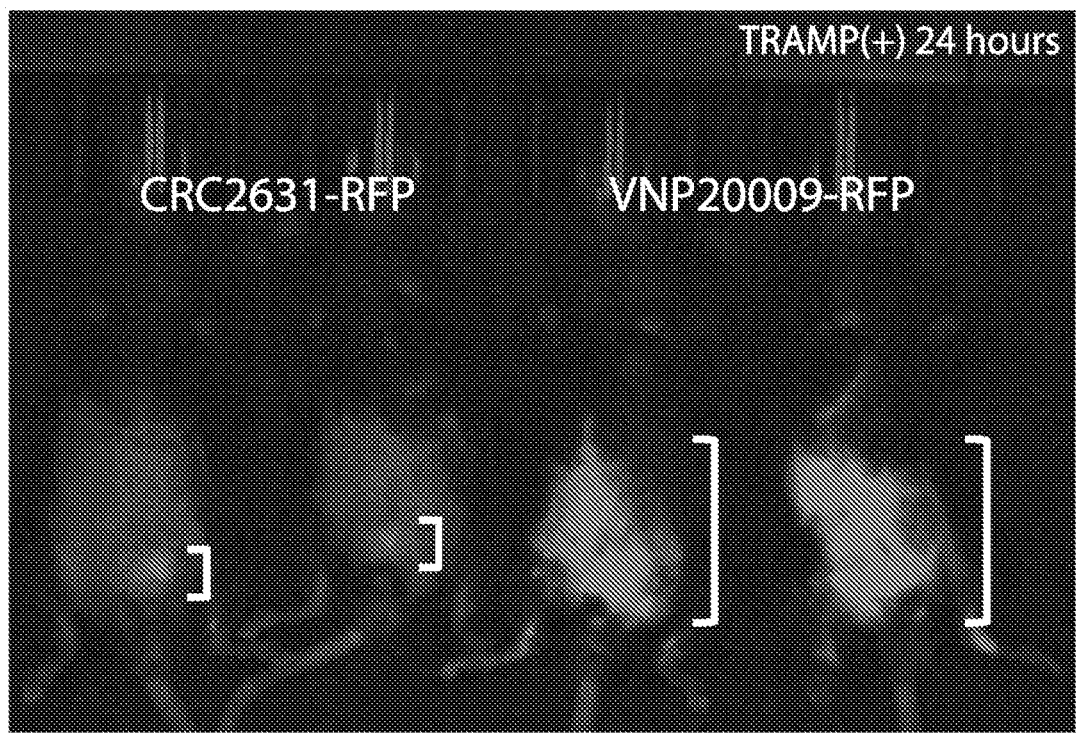

FIG. 7B depicts qualitative localization and persistence of CRC2631 and VNP20009 expressing mCherry red fluorescent protein (RFP) in B6 TRAMP(+) mice bearing primary prostate tumors. $1×10^6$ of each strain was administered interperitoneally and in vivo fluorescence scanning to detect mCherry RFP was performed at 24 hours post injection (hpi). Staining shows CRC2631- or VNP20009-associated unmixed mCherry signal (bracketed) or tissue autofluorescence. In contrast to the VNP20009 mCherry signal spread throughout the mouse abdomen, the CRC2631 mCherry signal is concentrated at the prostate. CRC2631 successfully colonizes the primary prostate tumor at 24 hpi in B6 TRAMP(+) mice.

Figure 7C:
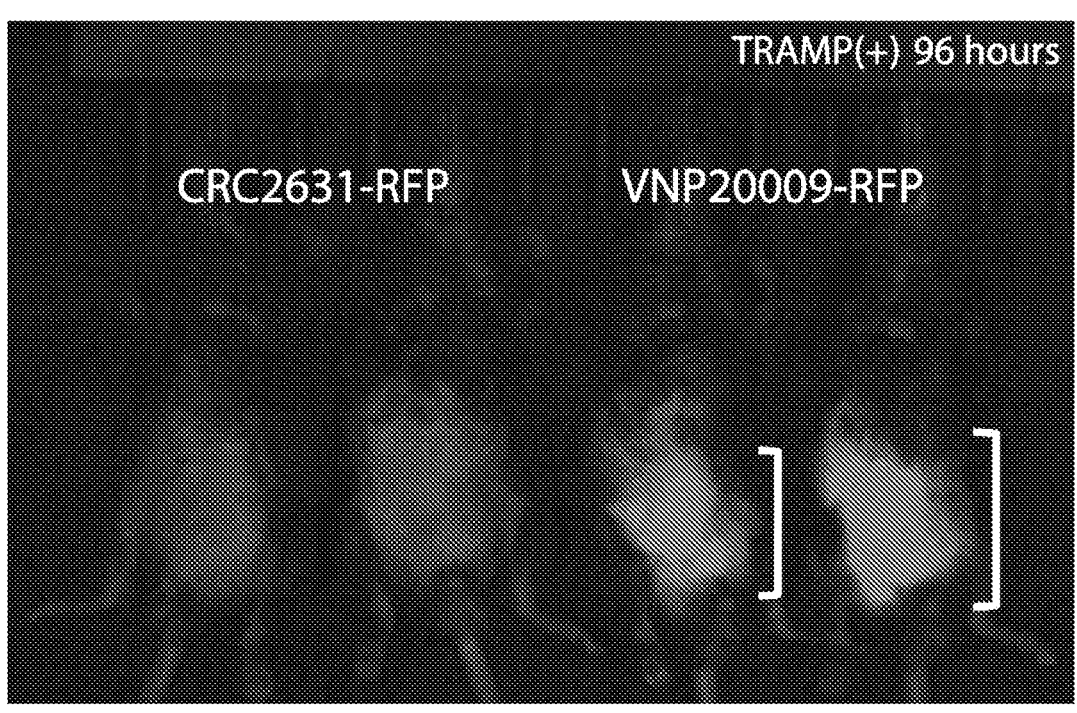

FIG. 7C depicts qualitative localization and persistence of CRC2631 and VNP20009 expressing mCherry red fluorescent protein (RFP) in B6 TRAMP(+) mice bearing primary prostate tumors. $1×10^6$ of each strain was administered interperitoneally and in vivo fluorescence scanning to detect mCherry RFP was performed at 96 hours post injection (hpi). Staining shows CRC2631- or VNP20009-associated unmixed mCherry signal (bracketed) or tissue autofluorescence. At 96 hpi, VNP20009 mCherry signal is spread throughout the mouse abdomen. CRC2631 mCherry signal becomes undetectable at 96 hpi.

Figure 7D:
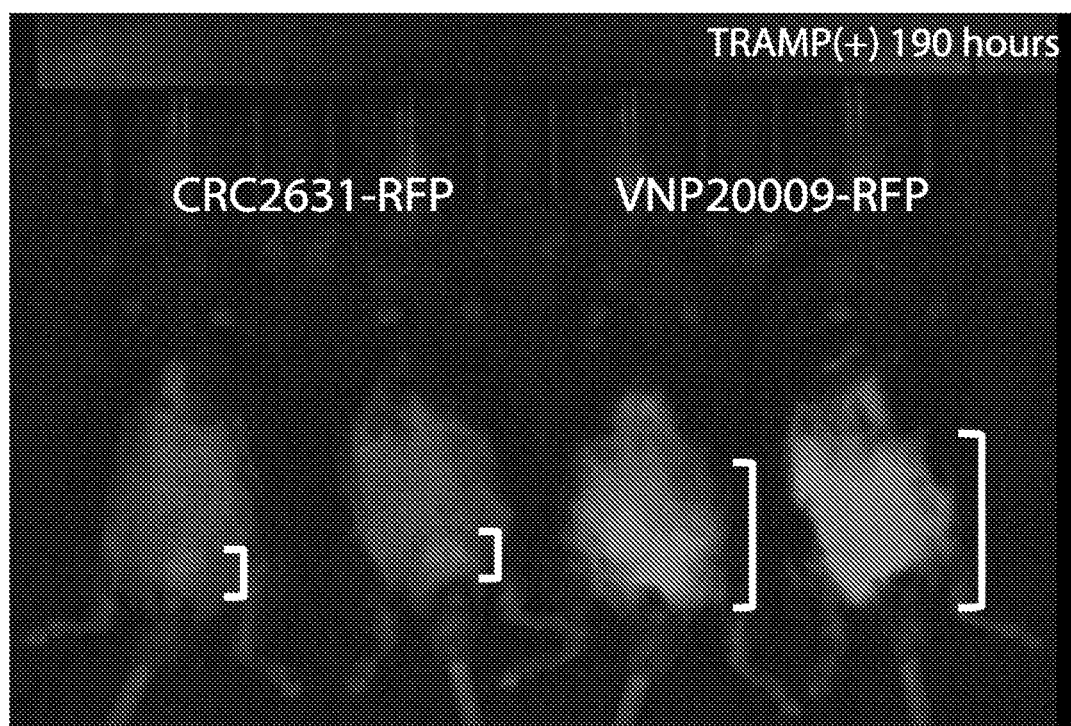

FIG. 7D depicts qualitative localization and persistence of CRC2631 and VNP20009 expressing mCherry red fluorescent protein (RFP) in B6 TRAMP(+) mice bearing primary prostate tumors. $1×10^6$ of each strain was administered interperitoneally and in vivo fluorescence scanning to detect mCherry RFP was performed at 190 hours post injection (hpi). Staining shows CRC2631- or VNP20009-associated unmixed mCherry signal (bracketed) or tissue autofluorescence. At 190 hpi, VNP20009 mCherry signal is spread throughout the mouse abdomen. CRC2631 mCherry signal re-emerges in the prostate tissue area at 190 hpi (brackets), demonstrating persistence in the B6 TRAMP(+) primary prostate tumor model.

Figure 8:
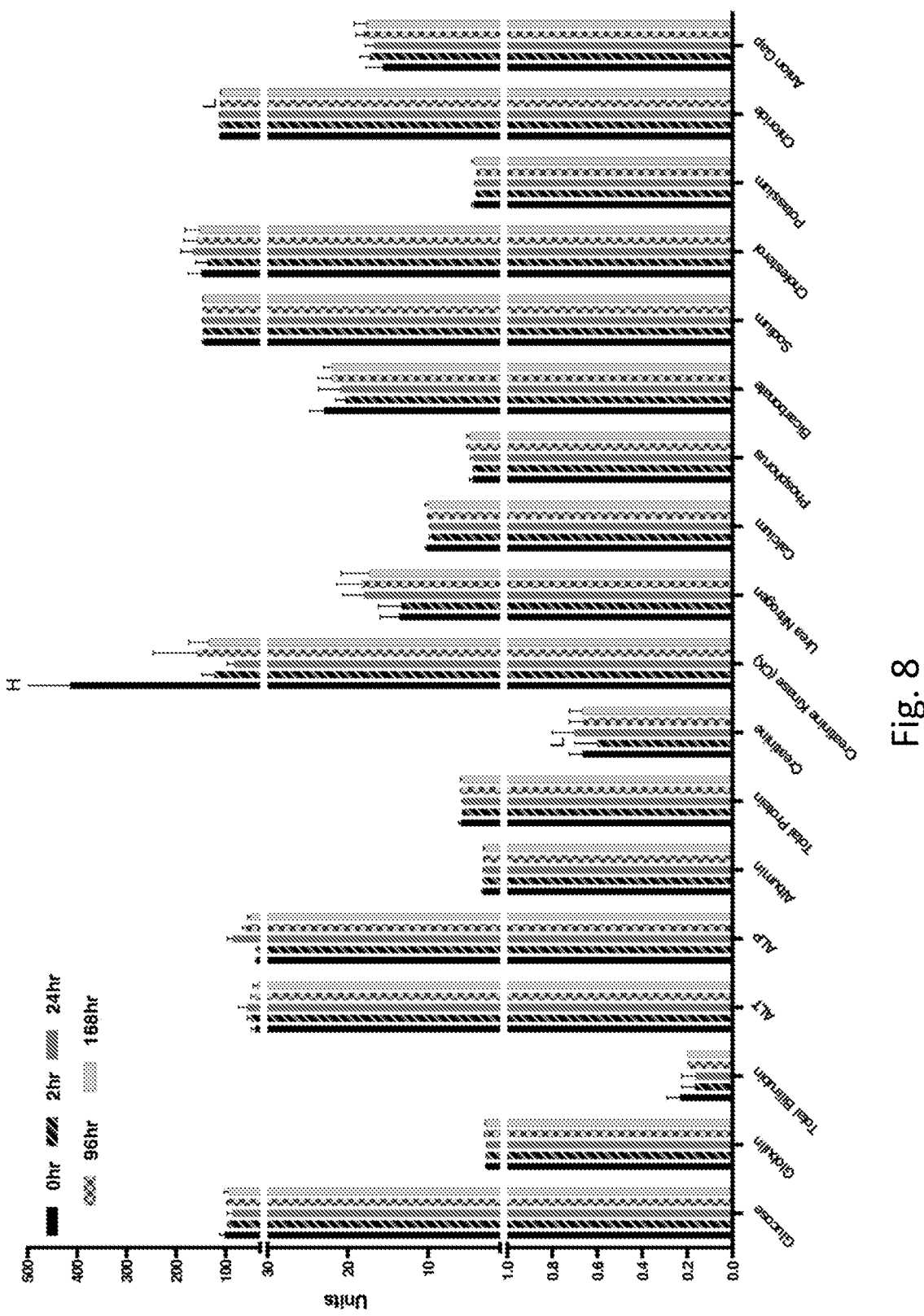

FIG. 8 depicts a toxicological assessment of CRC2631 in canine models. Three 13-month-old male beagles were administered $4×10^6$ CRC2631 intravenously, and plasma samples were collected at 0, 2, 24, 96, and 168 h time points. All animals tolerated CRC2631 injections. The chart shows the mean levels of plasma chemistry components in the three dogs to identify significant pathologies in organ tissue or metabolic function. All panels that included mean results outside of calibrated normal ranges (L=Low, H=High) are shown. Mean levels of creatinine below normal range at two hours post CRC2631 injection were not significantly different from initial levels (p<0.374). One dog exhibited high levels of creatinine kinase (CK) before injection of CRC2631, but CK levels were within normal range from 2-168 hours post injection and mean CK level changes from pre-injection to post injection were not significantly different at 2 h (p<0.372), 24 h (p<0.316), 96 h (p<0.436), or 168 h (p<0.389). Mean chloride levels at 96 hpi were below normal range but this was not significantly different from initial chloride levels (p<0.230). Each category on the x-axis shows from left to right columns for 0 hr, 2 hr, 24 hr, 96 hr, and 168 hr. Chemistry panels indicate no significant pathologies in organ tissue or metabolic function as a result of intravenous CRC2631 injections into dogs.

Figure 9A:
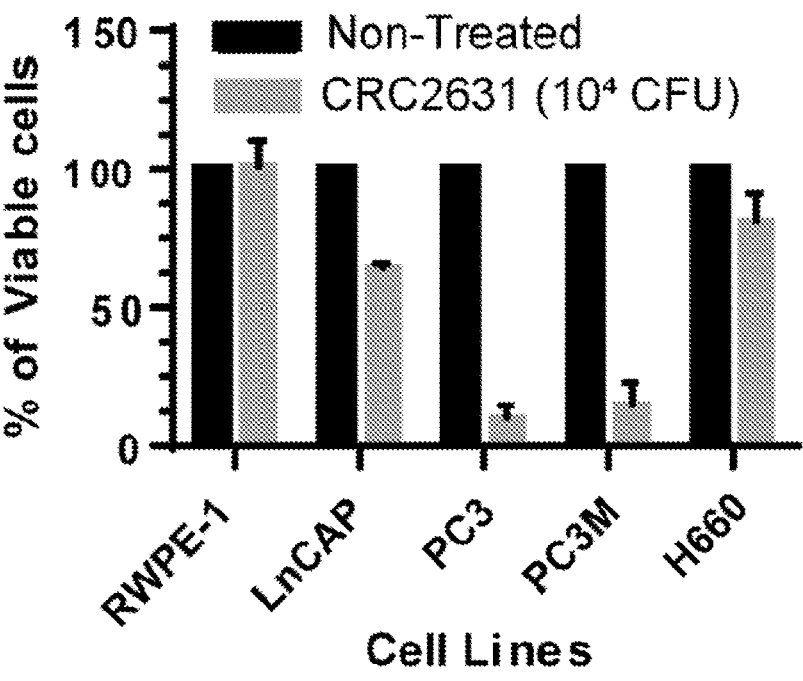

FIG. 9A depicts specificity of CRC2631 towards prostate cancer cells. Human benign prostate (RWPE-1) and prostate cancer (LnCAP, PC3, PC3M, H660) ($10^4$) cells were treated with $10^4$ CFU of CRC2631 for 4 h. Cell were then washed and cell viability was assessed using MTT assay. Results represent the mean±SD of three trials performed in triplicates.

Figure 9B:
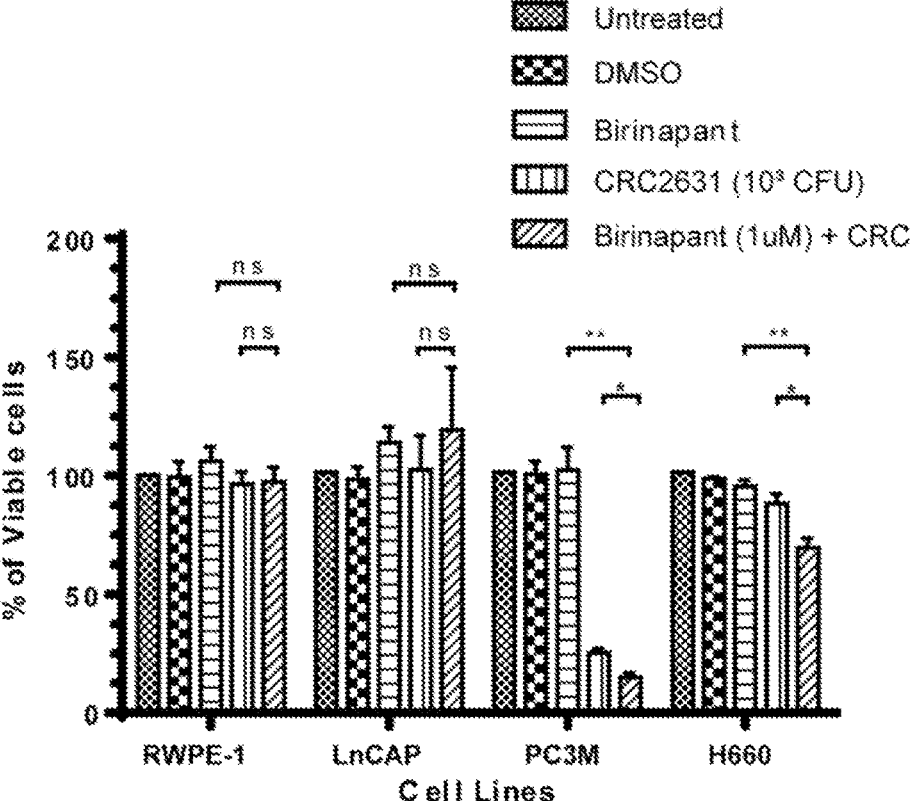

FIG. 9B depicts how CRC2631 in combination with birinapant kills prostate cancer and NEPC cells better than either treatment individually. Benign prostate (RWPE-1), prostate cancer (LnCAP, PC3M) and NEPC (H660) cells were treated with CRC2631 ($10^3$ CFU) and IAP antagonist, Birinapant (1 μM) either alone or in combination for 5 h. After washes, cell viability was measured by MTT assay. Results represent the mean±SD of three trials performed in triplicate (*, p<0.05; **, p<0.005, ns=not significant; Student's t-test).

Figure 9C:
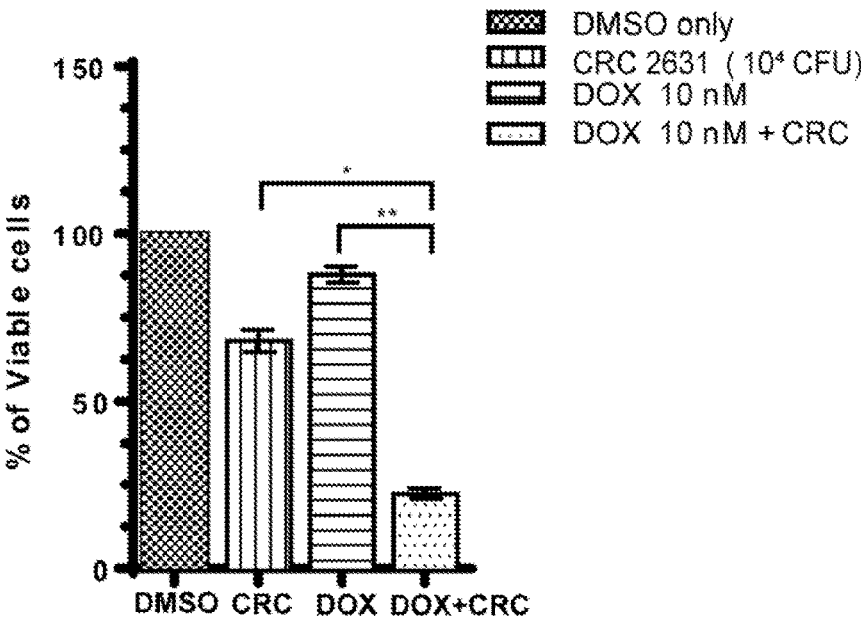

FIG. 9C depicts how CRC2631 in combination with standard chemotherapy treatment kills NEPC cells better than either individual treatment. NEPC (H660) cells ($10^3$) were treated with 10 nM of docetaxel (DOX) for 72 h. Media was replaced with fresh media containing CRC2631 ($10^4$ CFU) and cells were treated for 5 h. Cells were then washed and cell viability was measured using MTT assay. Results represent the mean±SD of three trials performed in triplicate (*, p<0.05; **, p<0.005; Student's t-test).

Figure 9D:
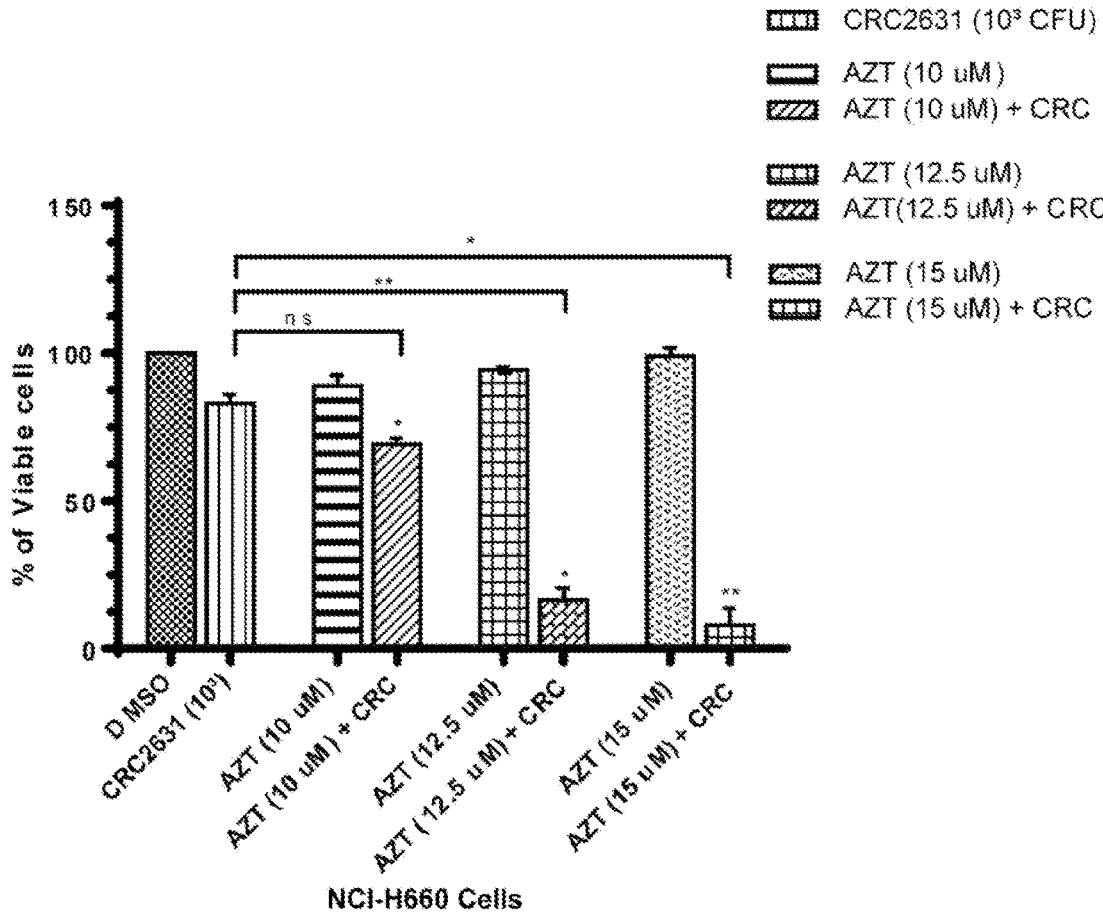

FIG. 9D depicts how CRC2631 in combination with standard androgen deprivation therapy kills NEPC cells better than either individual treatment. NEPC (H660) cells ($10^3$) were treated with 10 μM, 12.5 uM, or 15 uM enzalutamide (AZT) for 72 h. Media was replaced with fresh media containing CRC2631 ($10^3$ CFU) and cells were treated for 5 h. Cells were then washed and cell viability was measured using MTT assay. Results represent the mean±SD of three trials performed in triplicate (*, p<0.005; **, p<0.0005; Student's t-test)].

Figure 10A:
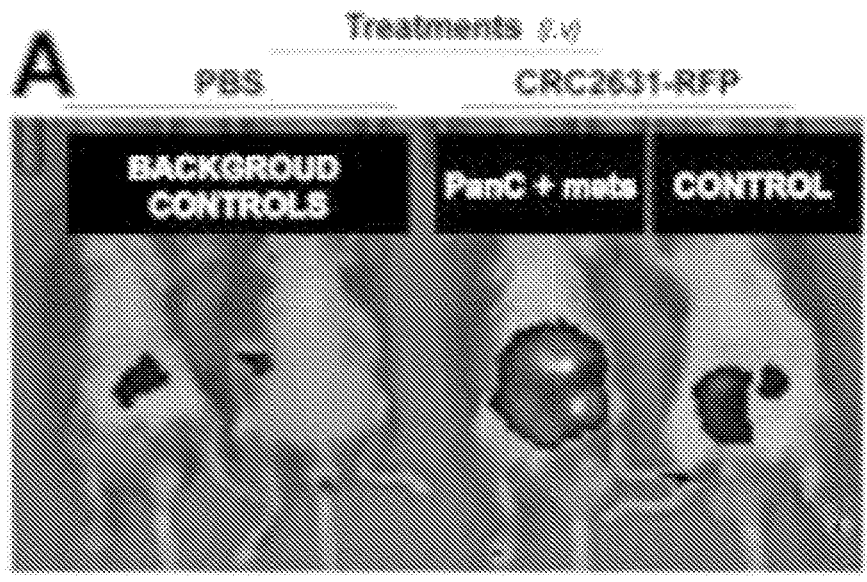

FIG. 10A depicts the tumor targeting capability of CRC2631$^{iRFP720-Cat}$ against pancreatic cancer in a mouse xenograft model. Groups (N=15) of tumor free (BL6) animals or animals carrying metastatic pancreatic cancer (B6Panc02H7) were treated intravenously with saline control (PBS) or iRFP-labeled CRC2631. In vivo fluorescence imaging was performed 4 days following treatment to assess the CRC2631 biodistribution. Dark areas indicate low CRC2631$^{iRFP720-cat}$-associated iRFP720 signal. Light areas within dark areas indicate high CRC2631$^{iRFP720-cat}$-associated iRFP720 signal, indicative of high CRC2631 load.

Figure 10B:
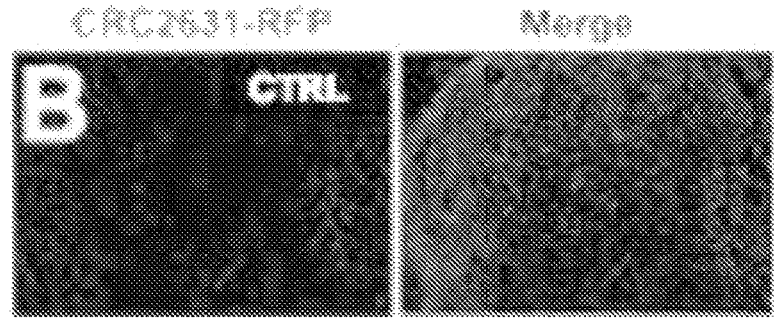

FIG. 10B depicts CRC2631$^{iRFP720-cat}$ imaging in pancreatic cryosectioned tissue sections obtained from tumor-free controls. CRC2631$^{iRFP720-cat}$ fluorescence is shown in the left panel, and this fluorescence is shown in a merge with DNA staining in the right panel.

Figure 10C:
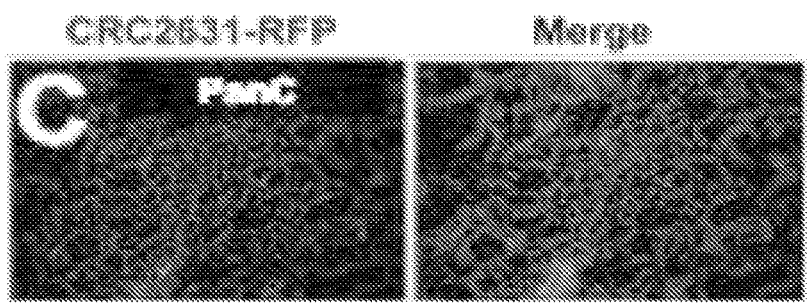

FIG. 10C depicts tumor tissue-specific enrichment of $CRC2631^{iRFP720\text{-}cat}$ in pancreatic cryosectioned tissue sections obtained from tumor-bearing animals. $CRC2631^{iRFP720\text{-}cat}$ fluorescence is shown in the left panel, and this fluorescence is shown in a merge with DNA staining in the right panel.

Figures 10D, 10E:
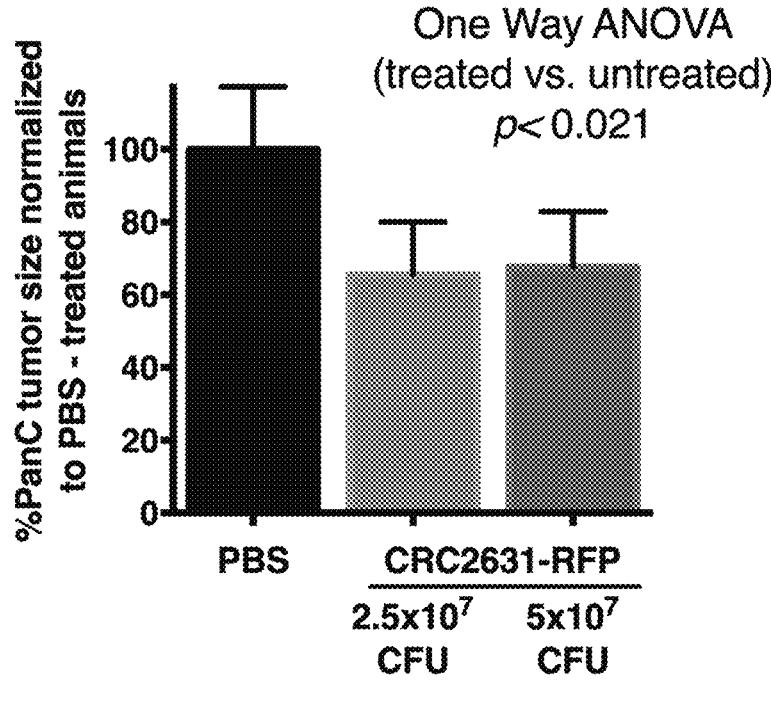

FIG. 10D depicts that PanC-targeted $CRC2631^{iRFP720\text{-}cat}$ notably reduces PanC tumor size. Tumors were harvested from PBS (control) or CRC2631-treated animals and weighed to determine the effect of CRC2631 on tumor size. Weight values were normalized to PBS control groups to establish treatment-induced percent change in tumor weight. P-values were derived from one-way ANOVA t-test.

FIG. 10E depicts that PanC-targeted $CRC2631^{iRFP720\text{-}cat}$ extends animal life at the $5\times10^7$ CFU dose. Kaplan Meyer survival analyses show the overall survival of B6PanC02H7 animals (N=6/group) treated with saline (PBS-no therapy control, dotted line), $2.5\times10^7$ CFU of CRC2631 (dashed line), or $5\times10^7$ CFU of CRC2631 (dashed and dotted line).

Figure 11:
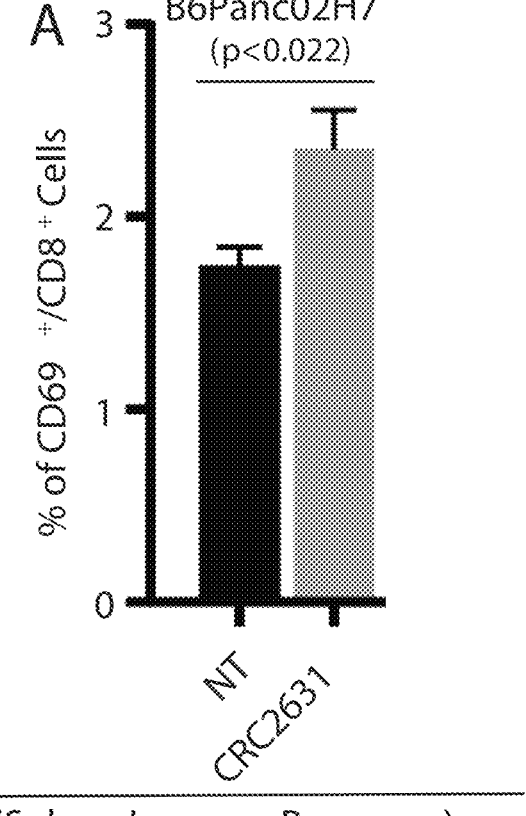

FIG. 11 depicts spleen immune response as the percentage of $CD69^+/CD8^+$ cells for no treatment (NT) control B6Panc02H7 mice and $CRC2631^{iRFP720\text{-}cat}$ treated (CRC2631) B6Panc02H7 mice. It shows that tumor-localized $CRC2631^{iRFP720\text{-}cat}$ activates anti-tumor $CD8^+$ immune cells in the spleen.

DETAILED DESCRIPTION

Conventional chemotherapies are not cancer-specific and as a result generate significant morbidities. Several toxicity-mitigating strategies have previously been proposed, including the use of genetically attenuated bacteria that specifically colonize tumor tissues to deliver therapeutics. However, the lack of bacterial cancer targeting (BCT) strains that are objectively safe continues to limit the clinical utility of these technologies. This is partly because preclinical tumor-targeting and safety evaluations have relied on moderate cancer models in immune suppressed animals. The most studied BCT strain, VNP20009, safely colonized tumors in immune-suppressed animal models but failed to generate a therapeutic signal in human patients, presumably because of rapid immune clearance by the host. The present disclosure describes the toxicological, tumor-targeting, and therapeutic profiles of CRC2631 in a syngeneic mouse model of aggressive prostate cancer (TRAMP). It is shown that CRC2631 is a safe and genetically stable biologic that persistently colonizes tumors, including metastases. Furthermore, the present disclosure also describes how CRC2631 can be used in combination with conventional chemotherapies, immunotherapies, and androgen receptor antagonist therapies to kill cancer cells better than any of the individual treatments.

The present application also discloses the toxicological, tumor-targeting, and efficacy profiles of *Salmonella enterica* serovar *Typhimurium* CRC2631 in a syngeneic and autochthonous TRAMP model of aggressive prostate cancer when used with immune checkpoint inhibitors to trigger anti-tumor immune activity, reducing tumor burden, and improving survival.

The present disclosure also describes how CRC2631 targets and blocks the growth of tumors in a mouse model of pancreatic cancer (B6Panc02H7) and causes an increase in the spleen immune response. This led to life extension in these mice.

CRC2631 was derived from a parent strain (CRC1674) that was isolated in a genetic screen for mutants that selectively kill breast and prostate cancer cells in vitro using the Demerec collection. This collection consists of mutant strains that arose naturally under nutrient-limiting conditions for over four decades, generating a wealth of genetically diverse and potentially attenuated strains. CRC2631 is a biologically pure *Salmonella typhimurium* strain that contains defined naturally occurring genetic alterations, in addition to targeted disruptions of the aroA, thyA, and rfaH genes to improve the strain's tumor-targeting capability and in vivo tolerability. The rfaH deletion disrupts lipopolysaccharide biosynthesis, while the aroA and thyA deletions introduced auxotrophy for aromatic amino acids and thymine.

The TRAMP (Transgenic Adenocarcinoma of Mouse Prostate) model recapitulates some of the key genetic aspects of human prostate cancer. An androgen-dependent promoter drives the expression of simian virus 40 (SV40) large and small T antigens specifically in the mouse prostate epithelium. This leads to the inhibition of p53 and Rb, causing prostatic carcinomas by eight weeks of age. Similar to prostate cancers in men, these murine carcinomas disseminate throughout visceral organs, differentiate into neuroendocrine prostate cancer (NEPC), and ultimately kill the host. While the molecular underpinnings that drive the conversion of carcinomas into NEPC are not well understood, NEPC is associated with loss of the tumor suppressors Rb and p53 in human prostate cancer.

In vitro, CRC2631 selectively colonized cancer cells of diverse histological origins, including breast and prostate cancer cells. Systemic delivery (intravenous or intraperitoneal administration) of CRC2631 in a prostate cancer mouse model (TRAMP) showed tumor-targeted CRC2631 localization. Importantly, CRC2631 triggered the expression and secretion of C-X-C chemokines and cytokines in vitro and in vivo. Congruent with this, CRC2631 elevated the frequency of activated CD4+ cells (CD69+/CD4+) tumor infiltrating lymphocytes (TILs) in prostate tumors and lymph node metastases.

The present disclosure shows that CRC2631 safely and persistently targeted tumor lesions, including metastases. Tumor-targeted CRC2631 induced anti-tumor immune activity and concordantly reduced metastasis burden in the setting of checkpoint blockade. CRC2631 preferentially colonized primary and metastatic tumors in the TRAMP animals. Furthermore, combining checkpoint blockade with CRC2631 extended animal life in TRAMP animals.

Longitudinal genome sequencing data from tumor-passaged CRC2631 revealed minimal genomic evolution. This indicated that CRC2631 is a genetically stable biologic that safely targets tumors.

CRC2631 advantageously destroys human NEPC cells when combined with chemotherapy or ADT in vitro. This therapeutic advantage in combination offers the possibility to generate durable clinical benefits using each agent at subtoxic levels, potentially minimizing treatment-related morbidities. This approach will also broaden the access of chemotherapy and ADT to the NEPC patients market. Therefore, combined with its capacity to kill NEPC cells in chemotherapy or ADT combination treatment settings, CRC2631 as a therapy can promote durable clinical benefits in cancer immunotherapy strategies in a safe and cost competitive manner.

Comparing the toxicity and tumor-targeting profiles of CRC2631 against those of VNP20009 showed that VNP20009 generates more toxicity than CRC2631 and poorly targets tumor tissues in immune-competent TRAMP animals (FIG. 7B-FIG. 7D). Consistent with these observations and in contrast to earlier findings from nude animals, VNP20009 also showed significant toxicity and poor tumor targeting capabilities in an immune-competent mouse model of mammary carcinoma.

CRC2631 partly owes its tolerability and enhanced tumor-targeting characteristics to its unique genomic evolution. CRC2631 was isolated from a collection of naturally occurring mutant strains that arose after maintaining the *Salmonella* LT2 in nutrient-limiting conditions for over four decades. This long-term selection generated a diverse array of genetic alterations while removing the selective pressure to maintain factors that are required for bacterial virulence in a human host. In addition, CRC2631 has disruptions to aroA, rfaH, and thyA genes, which cause deficiencies in lipid polysaccharide biosynthesis (leading to even less toxicity) and auxotrophy for aromatic amino acids and thymine (favoring CRC2631 growth specifically in metabolically rich environments such as cancers). These properties not only augment its tumor targeting but also limit its toxicity. Consistently, CRC2631 was specifically enriched in tumor tissues and did not cause overt toxicity (Table 2A and Table 2B). Additional support for CRC2631 safety and preferential colonization of tumor tissues comes from the findings that CRC2631 is well tolerated in healthy dogs. Serial blood analyses revealed relatively normal organ function (FIG. 8).

In addition to the preferential growth in cancers, other mechanisms likely contribute to CRC2631 tumor tropism. It has previously been shown that *Salmonella* requires wild type serine, aspartate, and ribose chemoreceptors as well as flagellar motility for active targeting of colon carcinoma cylindroids in vitro. Additionally, CRC2631 was screened against a library of human cell surface glycoproteins to identify specific cell surface molecules required for CRC2631-host interaction. CRC2631 was found to bind 10- to >400-fold more efficiently to mannose-linked terminal disaccharide glycoproteins, which are commonly found on cancer cells. This suggests that cancer-specific surface molecules promote the selective entry of CRC2631 into cancer cells.

Longitudinal genome analyses of tumor-passaged CRC2631 showed that CRC2631 remains genetically stable within the tumor microenvironment. At the $2.5 \times 10^7$ CFU dose, mutation rate modeling estimates a 0.15% probability that an average gene within CRC2631 will acquire a mutation inside the host within ten days of treatment. An average gene within CRC2631 would require 100,000 days inside the host to reach the absolute certainty that it will acquire a SNP, which is well beyond the time window of any therapy. A limitation of the modeling approach is that it makes predictions for an average gene within CRC2631 and does not take into account base pair level information for individual genes. It is contemplated that extending the model to this level would require larger samples over deep time points. These modeling data allow one to rationally assign risk levels for specific dosing regimens in other pre-clinical models or in human patients.

Potent CRC2631-based combination treatments were also developed that generate advantageous cell killing effects on treatment resistant prostate cancer cells. Importantly, CRC2631 reduced metastasis incidence in the setting of checkpoint blockade. This is significant because metastasis is the main cause of cancer-associated deaths and no effective immunotherapies against prostate cancer currently exist.

CRC2631 was also demonstrated to have therapeutic effects in the treatment of pancreatic cancer. CRC2631 targeted mouse pancreatic tumors, caused a reduction in tumor size and increase in the mouse spleen immune response, and ultimately led to an extension in lifespan.

Collectively, these findings indicate that CRC2631 is a genetically stable biologic that safely targets tumors, including metastases, in immune-competent hosts.

The present disclosure is directed to a composition comprising a biologically pure isolate of the genus *Salmonella* comprising archival strain CRC1674, wherein the isolate further comprises a disruption of at least one gene selected from the group consisting of aroA, rfaH, and thyA and at least one of a chemotherapy agent, an immunotherapy agent, and an androgen receptor antagonist.

The at least one gene can comprise aroA, rfaH, and thyA.

The disruption can be a deletion of all, parts, or a part of the genomic sequence of aroA, rfaH, thyA, or a combination thereof. The disruption can be via any method of disrupting bacterial genes known in the art, including lambda red recombination and TN10 cassette insertion. The disruption can cause a reduction in bacterial toxicity to humans. The disruption can block completion of bacterial synthetic pathways. The bacterial synthetic pathways can be for the synthetic aromatic amino acids, folic acid, lipopolysaccharide, and nucleic acids. The isolate can further comprise a disruption in one or more other genes that decrease bacteria toxicity to humans including disrupting bacterial synthetic pathways.

The isolate is a genetically stable biologic. This indicates it is not expected to accumulate mutations during the timescales it is used for treatments (i.e. days).

Furthermore, the isolate is tumor-targeting; the isolate preferentially colonizes tumors and tumor metastases compared to normal body tissues.

This isolate can comprise archival *Salmonella enterica* serovar *Typhimurium* strain CRC2631 (Patent Deposit #PTA-126791). The isolate can also comprise derivatives of CRC2631, which are isolates of CRC2631 that have at least one genetic difference from CRC2631 but retain at least 99.9%, at least 99%, or at least 95% sequence identity to strain CRC2631.

The present disclosure is further directed to a method for treating cancer in a patient in need thereof, the method comprising administering an effective amount of a biologically pure isolate of the genus *Salmonella* comprising archival strain CRC1674, wherein the isolate further comprises a disruption of at least one gene selected from the group consisting of aroA, rfaH, and thyA, and a chemotherapy agent, an immunotherapy agent, or a chemotherapy agent and an immunotherapy agent.

More specifically, the present disclosure is directed to a method for treating prostate cancer in a patient in need thereof, the method comprising administering an effective amount of a biologically pure isolate of the genus *Salmonella* comprising archival strain CRC1674, wherein the isolate further comprises a disruption of at least one gene selected from the group consisting of aroA, rfaH, and thyA and a chemotherapy agent, an androgen receptor antagonist, or a chemotherapy agent and an androgen receptor antagonist.

CRC2631 in combination with the chemotherapy agent, immunotherapy agent, androgen receptor antagonist, or combination thereof kills cancer cells more efficiently than CRC2631, chemotherapy agent, immunotherapy agent, or androgen receptor antagonist alone.

For the above methods, the cancer can comprise a primary or metastatic tumor. The metastatic tumor can occur in or on the liver, lymph nodes, kidney, lung, prostate, or adjacent to the primary tumor. The cancer in a patient in need thereof can be a solid cancer (e.g. prostate cancer, pancreatic cancer, breast cancer, etc.). The cancer can preferably be neuroendocrine prostate cancer or pancreatic cancer.

For the above methods, the patient can be a mammal, preferably a human.

For the above methods, the effective amount of the isolate used as a bolus treatment can be at or below the clinically determined maximum tolerated dose.

The chemotherapy agent of the above compositions and methods can comprise birinipant, cabazitaxel, docetaxel, paclitaxel, mitoxantrone, carboplatin, vinorelbine, oftamoxifen, raloxifene, anastrozole, exemestane letrozole, imatanib, cyclophosphamide, lovastatin, minosine, gemcitabine, cytarabine, 5-fluorouracil, methotrexate, gosereline, vincristine, vinblastine, nocodazole, teniposide, etoposide, epithilone, vinorelbine, captothecin, daunorubicin, actinomycin D, mitoxantrone, acridine, doxorubicin, epirubicin, or idarubicin. The chemotherapy agent preferably comprises birinipant, docetaxel, paclitaxel, mitoxantrone, carboplatin, vinorelbine, cabazitaxel, or a combination thereof. The chemotherapy agent preferably comprises docetaxel, birinipant, or a combination thereof.

The immunotherapy agent can in the above compositions and methods comprise an immune checkpoint inhibitor, including Atezolizumab, Avelumab, Durvalumab, Pembrolizumab, Nivolumab, Invivomab®, Ipilimumab, or a combination thereof. The immunotherapy agent can preferably comprise Invivomab®.

The androgen receptor antagonist in the above compositions and methods can comprise bicalutamide, flutamide, enzalutamide, abiraterone, or a combination thereof. The androgen receptor antagonist can preferably comprise enzalutamide.

DEPOSIT INFORMATION

U.S. Pat. No. 8,282,919 is incorporated herein by reference for its description of the CRC2631 microorganism.

The biologically pure isolate of the genus *Salmonella* comprising archival strain CRC1674, wherein the isolate further comprises a disruption of aroA, rfaH, and thyA, is known herein as CRC2631. Strain CRC2631 was deposited on Jul. 21, 2020 at the ATCC® Patent Depository at 10801 University Boulevard, Manassas, Virginia 20110 USA under Patent Deposit #PTA-126791.

U.S. Pat. No. 8,282,919 describes how an inoculum of *S. typhimurium* strain CRC1674 was placed in a sealed glass stab jar containing solid Luria-Bertani (LB) agar in April of 1967. On Jan. 19, 1999, a plug of the agar stab was extracted and grown in LB broth. The mutations found after this archival storage are described in the literature and known in the art and include a G168T mutation of rpoS (RNA-polymerase sigma factor), partial suppression of the hisD2550 auxotrophic mutation in the parent strain, deletion of ten genes located in the membrane region of the microorganism, and substantial changes in one-hundred eighty-two genes amounting to 4.4% of the genome. Strain CRC2631 was produced to reduce archival strain CRC1674 toxicity and make a strain more amenable to human cancer therapies. CRC1674 was produced by disrupting the aroA gene via high-transducing phage P22HT inserting a Tn10 cassette. The TN10 cassette and its use in disrupting bacterial genes is known in the art. The rfaH and thyA genes were deleted via lambda red recombination. Lambda red recombination and its efficient recombination between short homologous sequences are known in the art. aroA is involved in the synthetic pathways relating to aromatic amino acids and folic acid. rfaH is involved in lipopolysaccharide (LPS) synthesis. thyA is involved in the production of nucleic acid precursors.

Primers used complementary to the thyA gene of *S. typhimurium* are provided as SEQ ID NOs: 1-2. Primers used complementary to the rfaH gene of *S. typhimurium* are provided as SEQ ID NOs: 3-4.

The genomic sequence of CRC2631 is provided as SEQ ID NO: 5, and the associated stable pSLT plasmid sequence is provided as SEQ ID NO: 6.

Formulations

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers. Pharmaceutically acceptable excipients for use in the compositions of the present invention are selected based upon a number of factors including the particular compound used, and its concentration, stability and intended bioavailability; the subject, its age, size and general condition; and the route of administration.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP® 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. Routes of administration include, but are not limited to, oral, parenteral (e.g., intravenous, intra-arterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration. For example, the agents of use with the current disclosure can be formulated by known methods for administration to a subject using several routes including: parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

The pharmaceutical compositions can be formulated, for example, for oral administration. The pharmaceutical compositions can be formulated as tablets, dispersible powders, pills, capsules, gel-caps, granules, solutions, suspensions, emulsions, syrups, elixirs, troches, lozenges, or any other dosage form that can be administered orally. Pharmaceutical compositions can include one or more pharmaceutically acceptable excipients. Suitable excipients for solid dosage forms include sugars, starches, and other conventional substances including lactose, talc, sucrose, gelatin, carboxymethylcellulose, agar, mannitol, sorbitol, calcium phosphate, calcium carbonate, sodium carbonate, kaolin, alginic acid, acacia, corn starch, potato starch, sodium saccharin, magnesium carbonate, microcrystalline cellulose, colloidal silicon dioxide, croscarmellose sodium, talc, magnesium stearate, and stearic acid. Further, such solid dosage forms can be uncoated or can be coated to delay disintegration and absorption.

The pharmaceutical compositions can also be formulated for parenteral administration, e.g., formulated for injection via intravenous, intra-arterial, subcutaneous, rectal, subcutaneous, intramuscular, intraorbital, intracapsular, intraspinal, intraperitoneal, or intrasternal routes. Dosage forms suitable for parenteral administration include solutions, suspensions, dispersions, emulsions or any other dosage form that can be administered parenterally.

Pharmaceutically acceptable excipients are identified, for example, in The Handbook of Pharmaceutical Excipients, (American Pharmaceutical Association, Washington, D.C., and The Pharmaceutical Society of Great Britain, London, England, 1968). Additional excipients can be included in the pharmaceutical compositions of the invention for a variety of purposes. These excipients can impart properties which enhance retention of the compound at the site of administration, protect the stability of the composition, control the pH, facilitate processing of the compound into pharmaceutical compositions, and so on. Other excipients include, for example, fillers or diluents, surface active, wetting or emulsifying agents, preservatives, agents for adjusting pH or buffering agents, thickeners, colorants, dyes, flow aids, non-volatile silicones, adhesives, bulking agents, flavorings, sweeteners, adsorbents, binders, disintegrating agents, lubricants, coating agents, and antioxidants.

Compounds described herein can be prepared as a salt. "Salt" as used herein refers to pharmaceutically acceptable salts of the compounds described herein which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66:1-19 (1977). Examples of pharmaceutically acceptable salts include, but are not limited to, nontoxic acid addition salts which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

In other embodiments, the compounds may be prepared as "prodrugs" in a pharmaceutically acceptable composition/formulation. As used herein, the term "prodrug" refers to a derivative of a compound that can hydrolyze, oxidize, or otherwise react under biological conditions (in vitro or in vivo) to provide a compound as described herein. Prodrugs may only become active upon some reaction under biological conditions, but they may have activity in their unreacted forms. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs and their uses are well known in the art (see, e.g., Berge, et al. 1977 J. Pharm. Sci. 66:1-19). Prodrugs can typically be prepared using well-known methods, such as those described in Burger's Medicinal Chemistry and Drug Discovery (1995, Manfred E. Wolff ed., 5thed. 172-178, 931-932).

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" can include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

Unless defined otherwise, all technical and scientific terms used herein have the same meaning as commonly understood by one of ordinary skill in the art to which the disclosure belongs.

EXAMPLES

The following examples are given for purely illustrative and non-limiting purposes of the present invention.

Example 1. Materials and Methods

The following materials and methods were used in all other examples.

Growth of Bacterial Cultures

Table 1 shown below includes a list of bacteria used in these experiments. Isolated colonies of bacteria were grown from −80° C. stock aliquots frozen in 25% glycerol (Fisher Scientific®) on solid or liquid LB media (Fisher Scientific®) containing 200 µg/ml thymine (Arcos Pharmaceuticals) and selective antibiotics [50 µg/mL kanamycin (Sigma®), 50 µg/mL ampicillin (Sigma®), or 20 µg/mL chloramphenicol (Gold Biotechnology®)] as required. Bacteria grown on solid media was incubated for 24-30 h at 37° C. before use. Liquid media cultures were incubated in 50 mL sterile tubes for 20-24 h in a 37° C., 220 rpm dry shaking incubator. Strains grown for injection were washed with sterile phosphate buffered saline (PBS) (Rocky Mountain Biologicals) and concentration adjusted for injection (FIG. 1A, FIG. 1B, and FIG. 1C) and for in vitro cell viability assays.

TABLE 1

| Bacterial strains, mouse models, and cell lines. | |
| --- | --- |
| Genotype | |
| Bacteria | |
| LT2 | Wild-type *Salmonella enterica* serovar Typhimurium strain. |
| CRC1674 | Derived from LT2 strains, hisD2550rpoS. Archived in room temperature agar stab 1958, recovered November 1998. |
| CRC2631 | CRC1674 aroA551::Tn10(Tet$^R$)ΔrfaHΔthyA::pKD4(Kan$^R$) |
| CRC2636 | CRC2631 pRSET-mCherry |
| VNP20009 | *Salmonella enterica* serovar Typhimurium 14028 (YS72 hyperinvasive, xyl-)Δpurl ΔmsbB |
| CRC2631$^{iRFP720\text{-}cat}$ | CRC 1674 aroA::Tn10(Tet$^R$)ΔrfaHΔthyA::P$_{tac}$-iRFP720cat(Cam$^R$) |
| Mouse | |
| C57 TRAMP | C57BL/6-Tg(TRAMP)8247Ng/J (Jax Laboratories) |
| C57 × FvB Tramp | C57BL/6-Tg(TRAMP)8247Ng/J (Jax Laboratories) × FvBNHsd (Envigo) |
| Cell Lines | |
| PC3 | Human prostate cancer cells; derived from metastatic site: bone |
| PC3M | PC3 variant with increased metastatic frequency |
| RWPE1 | Human epithelial prostate cells |
| TRAMP-C2 | Mouse epithelial prostate adenocarcinoma cells |

Cell Lines and Cell Culture Conditions

The cell lines used in these experiments are listed in Table 1. All cell lines were obtained from ATCC® (Manassas, VA). The RWPE-1 cell line was maintained in Keratinocyte Serum Free Medium (K-SFM) media (Gibco®); PC3 cells were grown in Ham's F-12K Medium (Gibco®) supplemented with Fetal Bovine Serum to a final concentration of 10%; and PC3M cells were maintained in RPMI 1640 (Cytiva®) supplemented with 10% FBS, 1 mM sodium pyruvate, 1× non-essential amino acids and 2 mM L-Glutamine. TRAMP-C2 cells were grown according to ATCC® guidelines. All cells were maintained at 37° C. with 5% CO$_2$.

Construction of CRC2631iRFP720-cat

The standard Datsenko and Wanner recombination protocol (Datsenko, K. A. and B. L. Wanner (2000). "One-step inactivation of chromosomal genes in *Escherichia coli* K-12 using PCR products." *Proc Natl Acad Sci USA* 97(12): 6640-6645.) was used to engineer the ΔthyA::Ptac-iRFP720 cat (Cam$^R$) insert into CRC2631, replacing the Kan$^R$ gene cassette at the ΔthyA::pKD4 (Kan$^R$) deletion site to create CRC2631$^{iRFP720\text{-}cat}$ (FIG. 3A). A 50 bp of flanking homology upstream and downstream of the region internal to the CRC2631 ΔthyA::pKD4 (Kan$^R$) insertion was engineered using a megaprimer primer construct to replace the Kan$^R$ gene cassette with a wild-type Ptac promoter, the iRFP720 gene from pBAD/HisB-iRFP720 (Addgene®), and the wild-type cat (Cam$^R$) gene from pRE112. An overnight liquid culture of CRC2631pKD46 was grown in 10 mL of LB+200 µg/ml thymine, 50 µg/mL ampicillin and 50 µg/mL kanamycin at 30° C., 220 rpm dry shaking incubator. A 0.25 mL overnight CRC2631pKD46 culture (1% inoculum) was subcultured into 25 mL LB+200 µg/ml thymine, 50 µg/mL ampicillin, 50 µg/mL kanamycin and 100 mM L-arabinose (Sigma®) media and grown in sterile 50 mL tubes on a 30° C., 220 rpm dry shaking incubator. After 10 h, cells were recovered by 10 min centrifugation at 4000 rpm and washed 4 times in 1 mL cold sterile water, then resuspended in 75 µl sterile 10% glycerol. Using a 0.2 cm electroporation gap cuvette (Fisher Scientific®) 1 μg of insert DNA was electroporated (2.5 kV) (Electroporator 2510, Eppendorf®) into the 10% glycerol CRC2631pKD46 cell suspension. One mL of LB+200 μg/ml thymine was added to the cuvette and the cells were allowed to recover at 37° C. for three hours. The cells were centrifuged at 13.2 k rpm for 1 min, the supernatant discarded, and resuspended in 500 μl LB+200 μg/ml thymine, then spread on selective plates containing LB+200 μg/ml thymine and 7.5 μg/mL chloramphenicol. These plates were incubated for 24 h at 37° C. to recover $Cam^R$ $Kan^S$ transformants. The temperature-sensitive pKD46 helper plasmid was lost by overnight growth at 42° C., growth of 20-200 isolated colonies on LB+200 μg/ml thymine+20 μg/mL chloramphenicol plates, and confirmation of the target $Cam^R$, $Kan^S$, $Amp^S$ antibiotic resistance profile using replica plating. The resulting $Cam^R$, $Kan^S$, $Amp^S$ ΔthyA::Ptac-iRFP720 cat ($Cam^R$) insertion $CRC2631^{iRFP720-cat}$ construct was confirmed by PCR analysis and fluorescence microscopy.

Fluorescence Microscopy of $CRC2631^{iRFP720-cat}$ $CRC2631^{iRFP720-cat}$ was grown for 24 h at 37° C., 220 rpm in LB +200 μg/mL thymine+20 μg/mL chloramphenicol, washed in one volume of PBS, fixed in one volume of PBS+4% paraformaldehyde, washed in one volume PBS, mounted under a glass coverslip at a 1:1 ratio in Vectashield+DAPI (Vector Laboratories) stain, cured in the dark at room temperature for 2 h, sealed, then observed on a Zeiss® Axiovert® 200M fluorescent microscope using a 63× objective with 1.4 NA. A Hamamatsu® Orca-ER monochrome charge-coupled device (CCD) camera was used to take 900 ms Cy5 filter+24 ms DAPI filter exposures, which were pseudocolored and overlaid to confirm fluorescent detection.

Mice

The mouse genotypes used in these experiments are listed in Table 1. Transgenic Adenocarcinoma of Mouse Prostate (TRAMP) mice of pure C57BL/6-Tg(TRAMP) 8247Ng/J (B6) (Jax Laboratories) or hybrid C57BL/6-Tg(TRAMP) 8247Ng/JxFvBNHsd (Envigo) (B6FVB) background were genotyped at 21-28 days of age to distinguish between heterozygous TRAMP(+) animals positive for the PB-Tag SV40 oncogene and TRAMP(−) animals negative for the PB-Tag SV40 oncogene as previously described. B6 and B6FVB TRAMP mice were allowed to grow to 8-31 weeks of age before use in studies. Food [LabDiet®5001 (Lab-Diet®) or AIN-93M (Research Diets®)] and water were provided ab libitum. Animals were observed and weighed on a daily basis during all studies. All animal studies were conducted in accordance with the principles and procedures outlined in the National Institutes of Health Guide for the Care and Use of Animals under the University of Missouri Animal Care and Use Committee supervision (MU IACUC protocols #8602 and #9501).

MRI Imaging

All mice used in toxicity studies were imaged on a Bruker AVANCE III MRI platform. This system has the capability of achieving a 50 μm resolution for imaging tumor models. Mice were anesthetized using 3% isoflurane; anesthesia was maintained with 0.5-2% isoflurane to keep breathing rate at 30 bpm during which axial and coronal scans of the mouse body were performed. Images were taken using Para Vision® 6 software (Bruker BioSpin Inc). Prostate tumor volumes were measured using Imaris® software (Bitplane) to normalize injection groups for an average range of primary tumor burden and to measure therapeutic response to treatment.

Toxicological Studies

All B6FVB TRAMP(+) mice used in toxicity studies were scanned using a Bruker® AVANCE III MRI platform as described above to confirm tumor burden. Mouse tumor burdens were graded by size using the Imaris® software package. Mice were randomly assigned to study groups ensuring that each group had a representative range of tumor burden. Mice groups were injected interperitoneally with up to 5×10^7 CRC2631 or VNP20009 or sterile PBS carrier volume (100-500 μl) or intravenously (tail vein) with 2.5× 10^7 CRC2631 in 200 μl PBS four to fourteen times with a weekly or three-day interval between doses until study completion or until loss of 50% of the group, after which tumor burden was determined using MRI scans and the mice subsequently evaluated for life extension.

Cytokine Assays

Whole blood samples were taken from B6FVB TRAMP (+) mice via saphenous vein draw into capillary tubes containing EDTA anticoagulant (Ram Scientific) 2 h before and 2 h after CRC2631 or VNP20009 injections to measure the innate CRC2631 and VNP20009 inflammatory cytokine response. Blood was placed on ice, and plasma immediately extracted from the whole blood by centrifugation for 10 min at 1000×g in a 4° C. centrifuge followed by transfer of the supernatant to a new Eppendorf® tube. Platelets were removed from the supernatant by centrifugation for 15 min at 2000×g in a 4° C. centrifuge. The resulting plasma supernatant was transferred to a sterile Eppendorf® tube and stored at −80° C. until the cytokines were measured using a Milliplex® xMAP® Mouse High Sensitivity TCell Magnetic Bead Panel kit MHSTCMAG-70K (Millipore®) following the kit protocol on a Luminex 200 system with Xponent® (v2.7). Data analysis was performed using Analyst (Millipore®).

In Vivo Fluorescent Imaging

All mice were fed a defined AIN-93M Mature Rodent diet (Research Diets®) for a minimum of seven days to minimize feed-related autofluorescence in the gastrointestinal system (Inoue, Y., K. Izawa, S. Kiryu, A. Tojo and K. Ohtomo (2008). "Diet and abdominal autofluorescence detected by in vivo fluorescence imaging of living mice." Mol Imaging 7 (1): 21-27.). B6 or B6FVB TRAMP(+) animals were injected either intraperitoneally with 1×10^6 CRC2631 pRSTmCherry or VNP20009 pRSTmCherry, or injected intravenously (tail vein injection) with 1×10^7 or 2.5×10^7 $CRC2631^{iRFP720-cat}$. Fluorescent imaging was performed using a Xenogen IVIS 200 in vivo fluorescence system (Perkin Elmer®) and analyzed using Living Image software (v4.7.3). iRFP720 expression spectral unmixing was performed as previously described to detect $CRC2631^{iRFP720-cat}$ associated iRFP720 in vivo (Shcherbakova, D. M. and V. V. Verkhusha (2013). "Near-infrared fluorescent proteins for multicolor in vivo imaging." Nat Methods 10 (8): 751-754.). Images containing mCherry RFP (FIG. 7A-FIG. 7D) were spectrally unmixed to distinguish the CRC2631 or VNP20009-associated signal in vivo using mCherry spectral unmixing settings in the Living Image software.

Biodistribution Analysis

B6FVB TRAMP(+) mice were injected intravenously (tail vein injections) with 200 μl sterile PBS containing 1.0×10^7 or 2.5×10^7 $CRC2631^{iRFP720-cat}$. Mice were humanely euthanized 190 hours post injection. Whole blood, lung, liver, spleen, kidneys, prostate, and proper axial lymph nodes as well as any discrete metastatic tumor masses were collected, weighed, and kept on ice. Whole blood samples were immediately diluted ¹⁄₁₀ in 25% glycerol and PBS and stored at −80° C. Tissue samples were homogenized in 3 mL sterile PBS for 20 seconds on ice using a TissueRuptor® homogenizer (Qiagen®) with sterile tips, mixed with 3 mL of sterile 50% glycerol, and stored at −80° C. All tissue samples were later thawed, passed through 40 μm sterile filters (BD) and immediately diluted, spotted in triplicate on selective LB+200 μg/ml thymine +20 μg/mL chloramphenicol plates, incubated at 37° C. and enumerated after 24 h following the Miles and Misra method (Hedges, A. J. (2002). "Estimating the precision of serial dilutions and viable bacterial counts." *Int J Food Microbiol* 76(3): 207-214.).

Histopathological Analyses

Histopathological analyses were performed on samples obtained at necropsy from 33-week-old male B6FVB TRAMP(+) mice (four treated with CRC2631, four untreated) to examine the effects of CRC2631 administration on tissues. The four 31-week-old treated mice were given four intraperitoneal injections of 2.5×10⁷ CRC2631 at three-day intervals, and the untreated mice were given 200 μl sterile PBS intraperitoneal injections. Animals were euthanized at the study endpoint (end of week 33) by CO₂ asphyxiation and subsequent exsanguination. The prostate, associated tumor masses, seminal vesicles, urinary bladder, kidneys, adrenal glands, spleen, liver, lung, heart, thymus and lymph nodes that were either visibly enlarged, indicated as having metastatic foci by MRI, or taken in conjunction with other prescribed tissues were collected and immediately fixed in 10% buffered formalin (Fisher Scientific®), paraffin embedded, sectioned (5 μm thick sections), mounted on glass slides and stained with hematoxylin and eosin for histopathologic examinations by light microscopy.

Flow Cytometric Analysis of Infiltrating Lymphocytes

Metastasized lymph nodes were homogenized, and cells were isolated. Immune cell phenotypes were determined via flow cytometry with a FACSAria (BD Biosciences) using the following antibodies: anti-mouse CD3 FITC, anti-mouse CD4 PE, anti-mouse CD8 PerCP/Cyanine 5.5, anti-mouse CD69 APC, and anti-mouse PD1 BV421. All antibodies were purchased from Biolegend®.

RNA Isolation and RNAseq

Prostate cells, benign (RWPE-1) and cancer (PC3 and PC3M) at 80% confluency, were treated with 10⁴ CFU of CRC2631 for 1.5 h at 37° C. and 5% CO₂. Total RNA was isolated from CRC2631-treated and non-treated samples using the RNeasy® Plus kit (Qiagen) as per the manufacturer's protocol. Integrity of RNA was checked on an agarose gel. Libraries were prepared using the TruSeq® RNA Sample Preparation Kit (Illumina®) according to the protocols recommended by the manufacturer, and each library was paired-end sequenced (2×75 bp) by using the NextSeq® High Output Flow Cell—SE75 platform at the University of Missouri DNA Core. Three biological replicates were performed for each sample.

CRC2631-PDL1 Blockade Treatment

To control for tumor burden, 9-12-week-old TRAMP animals were imaged and sorted into four groups (N=12/group). Animals were intravenously infused with PBS, 2.5× 10⁷ CFU of CRC2631, or 0.5 mg Invivomab® (murine anti-PDL1 antibodies; BXCELL, #BE0101) alone or in combination with 2.5×10⁷ CFU of CRC2631. Animals received one injection every three days for a total of four doses. To evaluate the effect of the therapy on tumor size, animals were MRI scanned 21 days after the completion of treatment. These MRI images were used to compare tumor sizes between groups and to determine metastatic incidences in lymph nodes and lungs.

Canine Studies

Four 13-month-old male beagles were administered one dose of 4×10⁶ CRC2631 by intravenous injection. Plasma, saliva, and fecal samples taken pre-administration (0 h) and at 2, 24, 96, and 168 h after CRC2631 administration. A small animal Maxi Panel, which covers glucose (mg/dL), urea nitrogen (mg/dL), creatinine (mg/dL), sodium (mEq/L), potassium (mEq/L), chloride (mEq/L), bicarbonate (mEq/L), anion gap (mEq/L), albumin (g/dL), total protein (g/dL), globulin (g/dL), calcium (mg/dL), phosphorus (mg/dL), cholesterol (mg/dL), total bilirubin (mg/dL), ALT (U/L), ALP (U/L), and CK (U/L), was performed and analyzed by the MU Veterinary Medical Diagnostic Laboratory (Columbia, MO).

Genome Sequencing and Analysis

CRC2631 was grown in a dry shaker in 10 mL of liquid LB +200 μg/ml thymine+50 μg/mL kanamycin for 24 hours at 37° C., 220 rpm. The overnight culture was split. One volume was used for extraction of chromosomal DNA using the standard Wizard genomic DNA prep kit (Promega®) protocol (CRC2631). The other volume was suspended in sterile PBS for intravenous tail injection of 2.5×10⁷ CRC2361 into groups of 11-15-week-old B6 TRAMP mice that were euthanized for tissue collection at 96 or 190 h post CRC2631 injection. Following biodistribution analysis protocols, isolated colonies of CRC2631 were identified after plating prostate tumor tissue homogenates on selective LB+200 μg/ml thymine+50 μg/mL kanamycin plates 24 h at 37° C. These colonies were grown in 10 mL of liquid LB+200 μg/ml thymine+50 μg/mL kanamycin media for 24 h at 37° C., 220 rpm. Four representative TRAMP prostate tumor-passaged overnight cultures from individual mice were used for extraction of chromosomal DNA, as described above (CRC2631a-d). Parental and prostate tumor-passaged chromosomal genomic DNA were sequenced following the standard Next Generation Sequencing NovaSeq® 2×100 protocol (Illumina®) and aligned against the parental LT2 and associated stable pSLT reference sequences (NCBI: NC_003197.2, NC_003277.2) using breSeq (v0.53.1), free-Bayes (v1.3.2), and TIDDIT (v2.10.0) to identify SNP mutations and structural variations present in the tumor-passaged strains (CRC2631a-d) but not in the CRC2631 injection strain. Integrative Genomics Viewer (v.2.8.0) was used to create graphical representations of SNP mutations and structural variations in all sequenced strains.

Mathematical Modeling

The occurrence of a SNP within a 96 h time span was modeled as a Bernouli random variable for each gene within the CRC2631 genome. SNP occurrences across genes were assumed to be independent of one another but not necessarily identically distributed. By Le Cam's theorem, the total number of mutations within CRC2631 within a 96 h time span, denoted X, will be approximately distributed as a Poisson random variable, i.e., X~Poisson(λ). Following a Bayesian approach, λ~Gamma(α,β), with α=1 and β=1, which represents a relatively uninformative prior over the rate parameter λ. For this model, the SNP counts from the three successful CRC2631 strains at 96 h, i.e., three occurrences of two SNPs were used. Thus, the posterior distribution of the rate parameter is λ~Gamma(7,4), with a posterior mean of 1.75 and corresponding 95% credible interval of [0.82, 2.96]. A rate value of 1.75 corresponds to an average gene SNP probability of p̂=0.00038 (for 4548 total genes); likewise, p̂=0.00018 and p̂=0.00065 for the upper and lower bounds of the corresponding 95% credible interval. Under a geometric distribution, these rate probabilities yield an expected value of 10391 days before a SNP in an average gene ($\hat{p}$=0.00038), likewise 22145 days ($\hat{p}$=0.00018) and 6141 days ($\hat{p}$=0.00065).

Cell Viability Assay

Prostate cells ($10^4$ per well) in their respective media were seeded in 96-well plates. The cells were allowed to adhere and recover for approximately 18 h after which they were treated with $10^4$ CFU of CRC2631 for 4 h. At the completion of treatment, media were replaced with gentamycin (40 µg/mL)-containing media for 1 h to eliminate extracellular bacteria. Cells were then washed twice with 1×PBS and cell viability was measured using the MTT Cell Proliferation Assay (ATCC® 30-1010K), as per the manufacturer's recommendation.

Statistical Analyses

All statistical analyses (Student's t test comparisons, ANOVA of mean weight differences over time) were performed using GraphPad Prism® software (v6.0 h).

Example 2. Evaluation of CRC2631 Toxicity

Figure 2B:
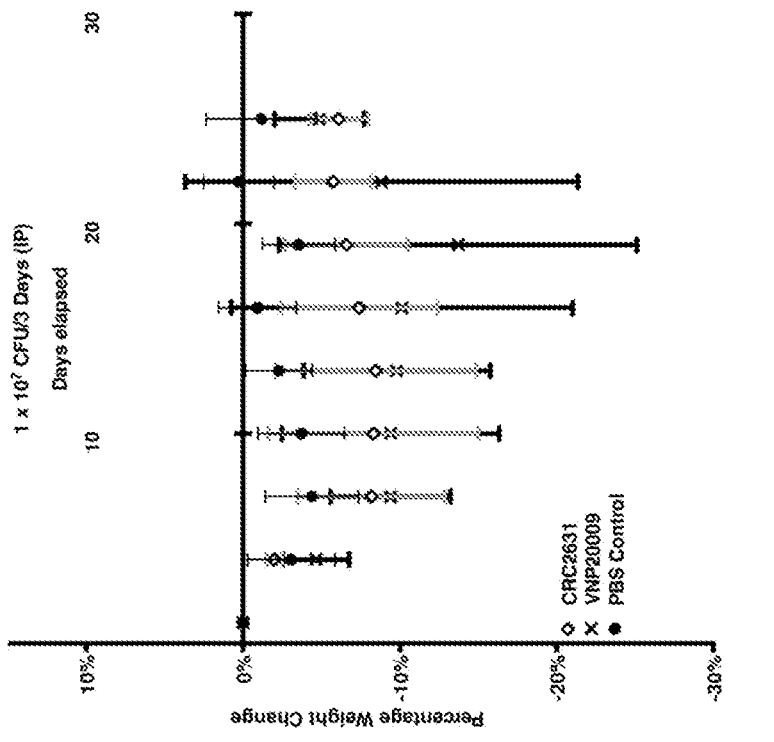
FIG. 2B depicts a comparative toxicological assessment of CRC2631 and VNP20009 using mean group weight change after administration of CRC2631 or VNP20009 intraperitoneal (IP) or intravenous (IV) injections into tumor-bearing B6FVB TRAMP(+) prostate cancer models. All B6FVB TRAMP(+) model tumor burdens were measured by MRI and mice groups sorted to normalize primary tumor volume size ranges for each dosage group before administration. Mean weight change of B6FVB TRAMP(+) mice (N=6) IP injected with 1×10⁷ CFU CRC2631, VNP20009, or equal volume PBS dosage every three days for 25 days or until LD50 was reached is shown.
Figure 2A:
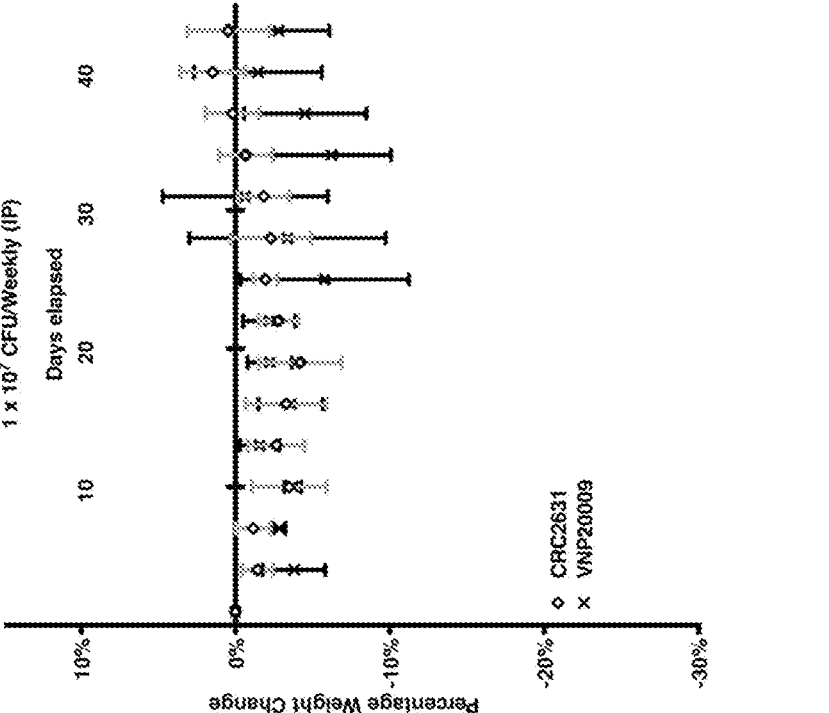
FIG. 2A depicts a comparative toxicological assessment of CRC2631 and VNP20009 using mean group weight change after administration of CRC2631 or VNP20009 intraperitoneal (IP) or intravenous (IV) injections into tumor-bearing B6FVB TRAMP(+) prostate cancer models. All B6FVB TRAMP(+) (Transgenic Adenocarcinoma of Mouse Prostate) model tumor burdens were measured by MRI and mice groups sorted to normalize primary tumor volume size ranges for each dosage group before administration. Mean weight change of B6FVB TRAMP(+) mice (N=4) injected with 1×10⁷ CRC2631 or VNP20009 IP dosage every week for five weeks is shown.
Figure 2C:
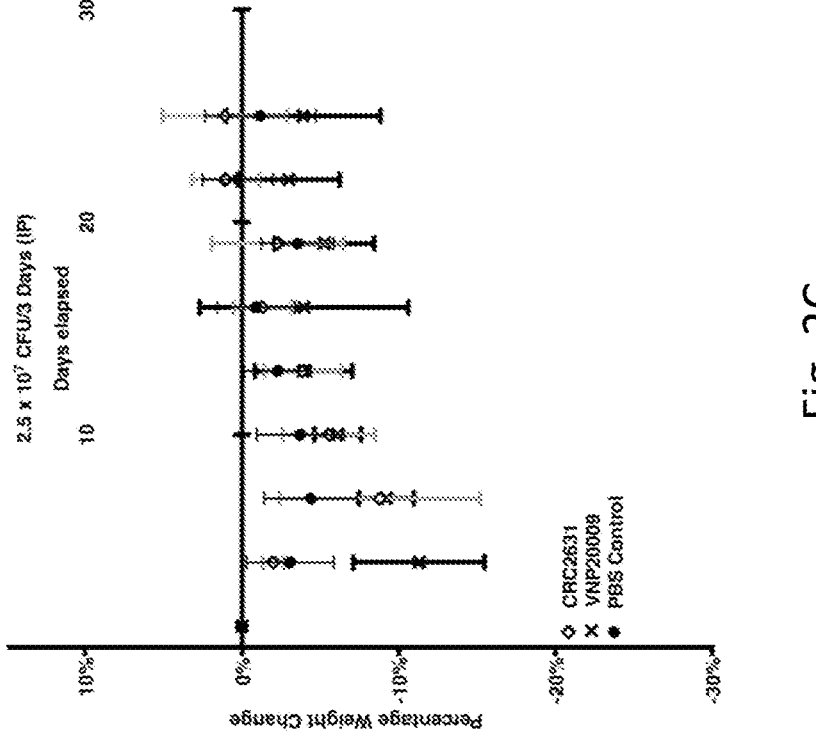
FIG. 2C depicts a comparative toxicological assessment of CRC2631 and VNP20009 using mean group weight change after administration of CRC2631 or VNP20009 intraperitoneal (IP) or intravenous (IV) injections into tumor-bearing B6FVB TRAMP(+) prostate cancer models. All B6FVB TRAMP(+) model tumor burdens were measured by MRI and mice groups sorted to normalize primary tumor volume size ranges for each dosage group before administration. Mean weight change of B6FVB TRAMP(+) mice (N=6) IP injected with 2.5×10⁷ CFU CRC2631, VNP20009, or equal volume PBS dosage every three days for 25 days or until LD50 was reached is shown.
Figure 2E:
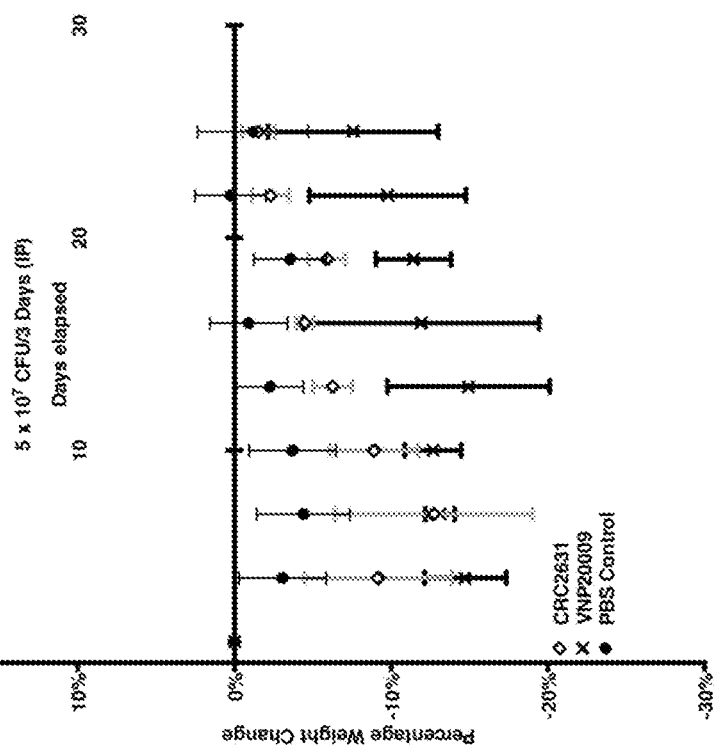
FIG. 2E depicts a comparative toxicological assessment of CRC2631 and VNP20009 using mean group weight change after administration of CRC2631 or VNP20009 intraperitoneal (IP) or intravenous (IV) injections into tumor-bearing B6FVB TRAMP(+) prostate cancer models. All B6FVB TRAMP(+) model tumor burdens were measured by MRI and mice groups sorted to normalize primary tumor volume size ranges for each dosage group before administration. Mean weight change of B6FVB TRAMP(+) mice (N=6) IP injected with 5×10⁷ CFU CRC2631, VNP20009, or equal volume PBS dosage every three days for 25 days or until LD50 was reached is shown.
Figure 2D:
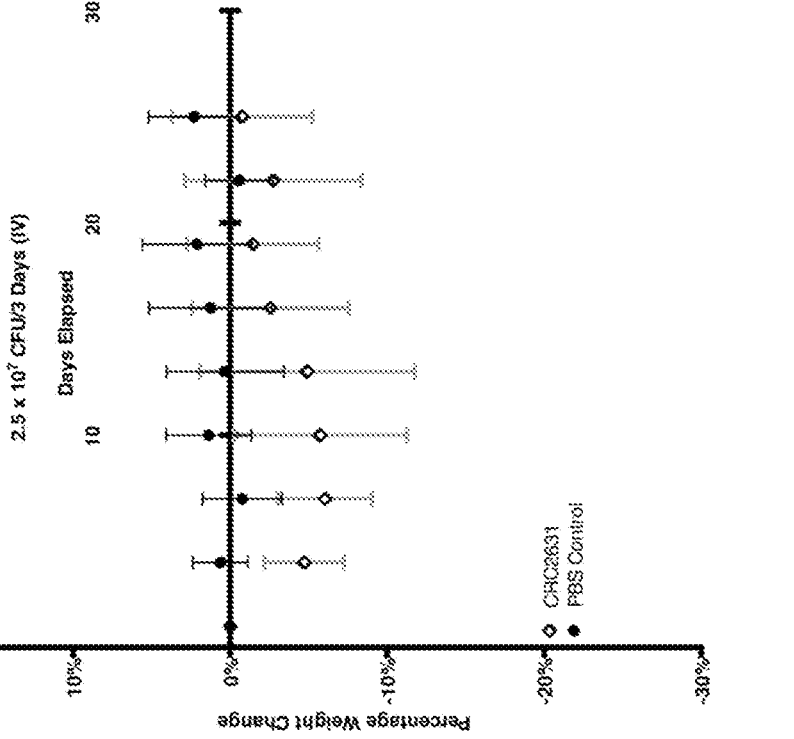
FIG. 2D depicts a comparative toxicological assessment of CRC2631 and VNP20009 using mean group weight change after administration of CRC2631 or VNP20009 intraperitoneal (IP) or intravenous (IV) injections into tumor-bearing B6FVB TRAMP(+) prostate cancer models. All B6FVB TRAMP(+) model tumor burdens were measured by MRI and mice groups sorted to normalize primary tumor volume size ranges for each dosage group before administration. Mean weight change of B6FVB TRAMP(+) mice (N=12) IV (tail vein administration) injected with four 2.5×10⁷ CFU CRC2631 or equal volume PBS dosage every three days for 25 days is shown.
Figure 2F:
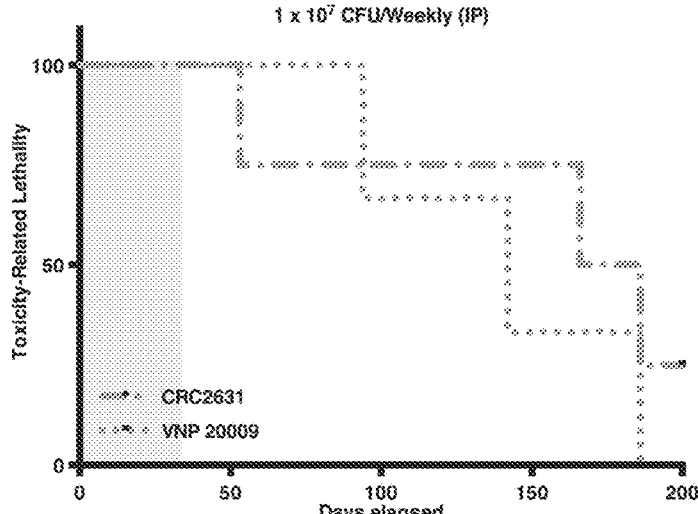
FIG. 2F depicts a comparative toxicological assessment of CRC2631 and VNP20009 using toxicity-related lethality after administration of CRC2631 or VNP20009 intraperitoneal (IP) or intravenous (IV) injections into tumor-bearing B6FVB TRAMP(+) prostate cancer models. All B6FVB TRAMP(+) model tumor burdens were measured by MRI and mice groups sorted to normalize primary tumor volume size ranges for each dosage group before administration. Toxicological measure of survival over 200 days of B6FVB TRAMP(+) mice (N=4) IP injected with 1×10⁷ CRC2631 or VNP20009 every week for five weeks is shown. Dosage time period is shaded in gray.
Figure 2G:
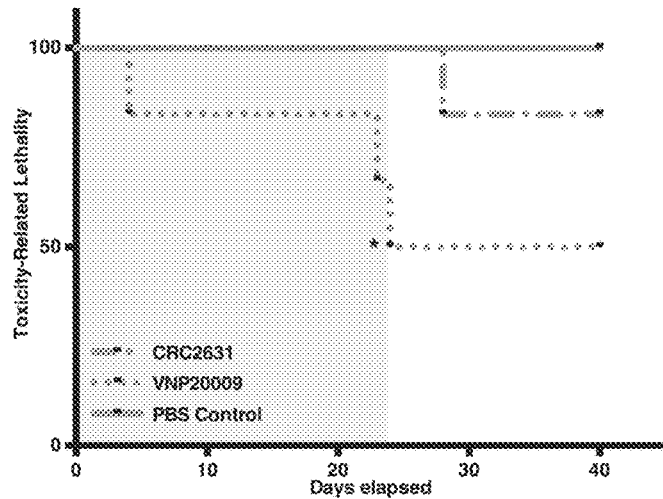
FIG. 2G depicts a comparative toxicological assessment of CRC2631 and VNP20009 using toxicity-related lethality after administration of CRC2631 or VNP20009 intraperitoneal (IP) or intravenous (IV) injections into tumor-bearing B6FVB TRAMP(+) prostate cancer models. All B6FVB TRAMP(+) model tumor burdens were measured by MRI and mice groups sorted to normalize primary tumor volume size ranges for each dosage group before administration. Toxicological measures of survival over 40 days of B6FVB TRAMP(+) mice (N=6) IP injected with 1×10⁷ CRC2631, VNP20009, or equal volume PBS dosage every three days for 42 days or until LD50 was reached is shown. Dosage time period is shaded in gray.
Figure 2H:
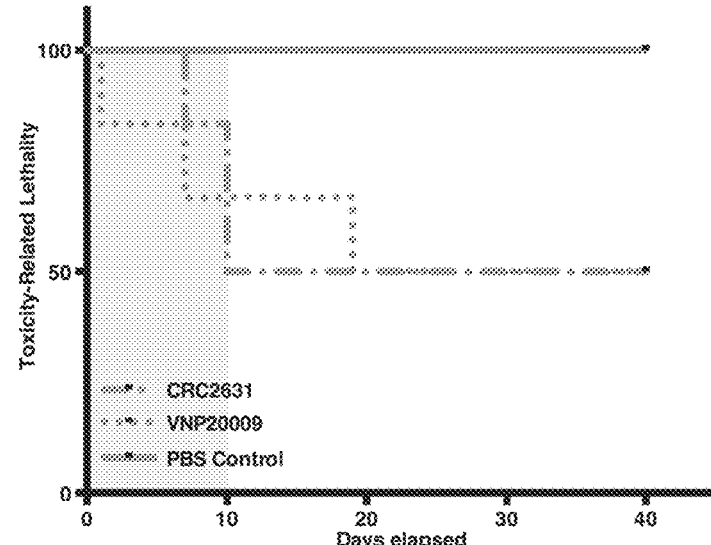
FIG. 2H depicts a comparative toxicological assessment of CRC2631 and VNP20009 using toxicity-related lethality after administration of CRC2631 or VNP20009 intraperitoneal (IP) or intravenous (IV) injections into tumor-bearing B6FVB TRAMP(+) prostate cancer models. All B6FVB TRAMP(+) model tumor burdens were measured by MRI and mice groups sorted to normalize primary tumor volume size ranges for each dosage group before administration. Toxicological measures of survival over 40 days of B6FVB TRAMP(+) mice (N=6) IP injected with $5 \times 10^7$ CRC2631, VNP20009, or equal volume PBS dosage every three days for 42 days or until LD50 was reached (*compassionate euthanasia of mouse with >20% weight loss) is shown. Dosage time period is shaded in gray.

VNP20009 is considered as the safety benchmark in bacterial cancer therapy development because it has been safely administered in human cancer patients. To determine the safety profile of CRC2631 and VNP20009 comparative toxicological studies were performed in TRAMP (Transgenic Adenocarcinoma of Mouse Prostate) animals. Treatment-related weight loss and lethality as toxicity measures were focused on. To control for tumor burden, groups of fourteen-week-old B6FVB TRAMP(+) mice were scanned by magnetic resonance imaging (MRI) and assigned either to the CRC2631 (N=4) or the VNP20009 (N=4) group. Animals received four weekly injections of $10^7$ CFU of CRC2631 or VNP20009 intraperitoneally (IP) (see Example 1, FIG. 1A-FIG. 1C), and animal weight was monitored daily for four weeks. CRC2631 and VNP20009 had comparable effects on animal weight loss within the first two weeks of the study. During the last two weeks of the study, however, VNP20009-treated animals progressively lost more weight compared to CRC2631-treated animals (FIG. 2A; p<0.0001, 3.50±1.77% versus 0.11±1.45% weight loss for VNP20009 and CRC2631, respectively). Consistent with CRC2631 being less toxic than VNP20009, the median survival time was 142 days for VNP20009 compared to 186 days for CRC2631 (FIG. 2F). To more rigorously determine the toxicity of CRC2631 and derive its maximum tolerated dose (MTD), the dosing regimen was escalated to $10^7$ or $2.5 \times 10^7$ or $5 \times 10^7$ CFU administered every 3 days, instead of weekly, until 50% group lethality (LD50) was reached. B6FVB TRAMP(+) groups were treated IP or intravenously with a vehicle control (a sterile phosphate buffered saline, PBS) or $10^7$ or $2.5 \times 10^7$ or $5 \times 10^7$ CFU of CRC2631 or VNP20009. Compared to VNP20009, CRC2631 caused less weight loss across all dosage groups over the injection period. The average weight loss percentages for animals treated with $10^7$, $2.5 \times 10^7$, and $5 \times 10^7$ CFU CRC2631 were 7.20±2.45, 3.35±3.58, and 6.69±3.88, respectively. In contrast, VNP20009-treated animals exhibited an average weight loss of 8.99±2.56, 6.13±3.15, and 11.68±2.70 at the corresponding dose levels (FIG. 2B, p<0.0085; FIG. 2C, p<0.0001; FIG. 2D, p<0.0001; FIG. 2E, p<0.0139). Congruent with this, no lethality was observed in the CRC2631 group at the time the VNP20009-treated animals reached LD50 at the $10^7$ CFU/3 day dosage interval level (FIG. 2G). In addition, the VNP20009 group experienced lethality after the first treatment at the $5 \times 10^7$ CFU/3 day dose level, whereas the counterpart CRC2631 group exhibited no lethality until the third treatment when it precipitously reached LD50 (FIG. 2H). This established the MTD at two doses of $5 \times 10^7$ CFU administered three days apart.

To minimize animal stress and thus the likelihood of animal lethality during the study, all the remaining studies were performed below MTD levels (i.e., at $10^7$ CFU or $2.5 \times 10^7$ CFU per animal).

Figure 2J:
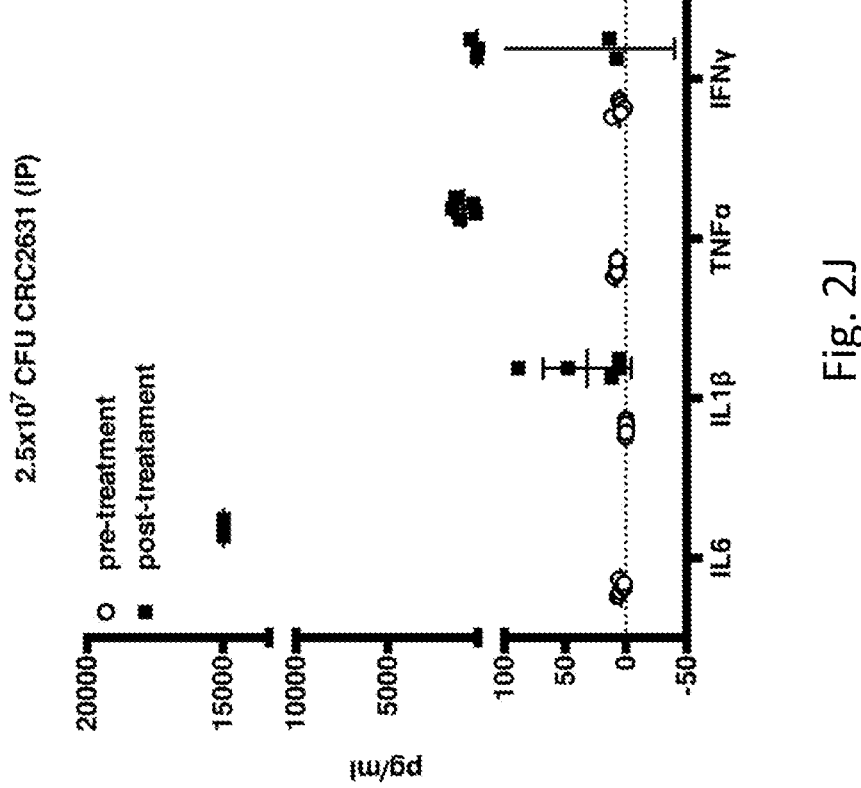
FIG. 2J depicts a comparative toxicological assessment of CRC2631 and VNP20009 using cytokine response after administration of CRC2631 or VNP20009 intraperitoneal (IP) or intravenous (IV) injections into tumor-bearing B6FVB TRAMP(+) prostate cancer models. All B6FVB TRAMP(+) model tumor burdens were measured by MRI and mice groups sorted to normalize primary tumor volume size ranges for each dosage group before administration. Inflammatory cytokine (IL-6, IL-1B, TNFα, INFγ) immune response levels in B6FVB TRAMP(+) mice (N=5) plasma two hours before and two hours after first IP injection of $2.5 \times 10^7$ CRC2631 are shown.
Figure 2I:
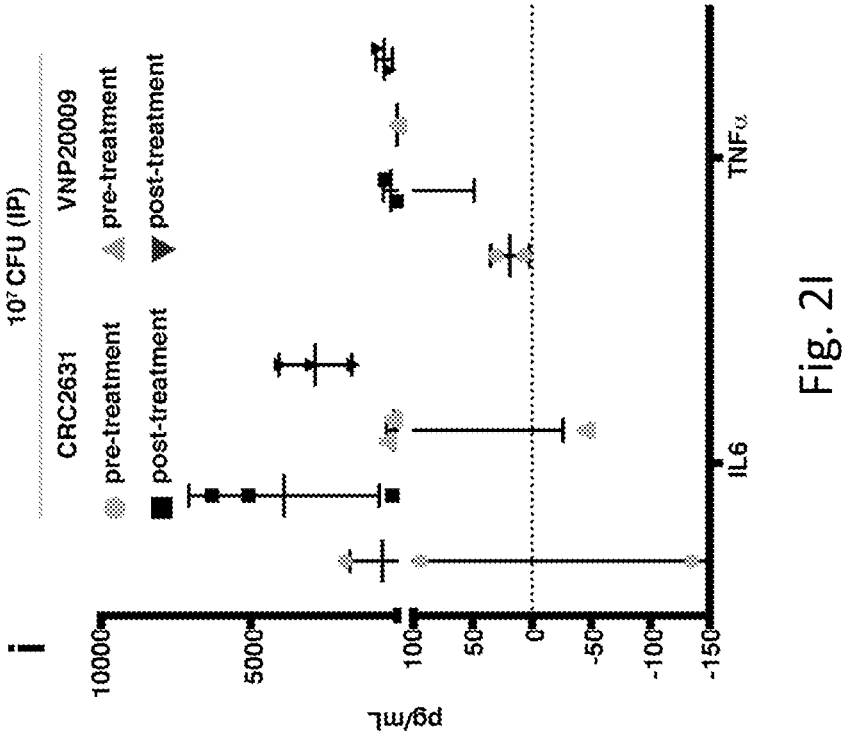
FIG. 2I depicts a comparative toxicological assessment of CRC2631 and VNP20009 using cytokine response after administration of CRC2631 or VNP20009 intraperitoneal (IP) or intravenous (IV) injections into tumor-bearing B6FVB TRAMP(+) prostate cancer models. All B6FVB TRAMP(+) model tumor burdens were measured by MRI and mice groups sorted to normalize primary tumor volume size ranges for each dosage group before administration. Inflammatory cytokine (IL-6, TNFα) immune response levels in B6FVB TRAMP(+) mice (N=3) plasma two hours before and two hours after first IP injection of $1 \times 10^7$ CRC2631 or VNP20009 are shown.

The next focus was whether the tolerability of CRC2631 was due to poor immunogenicity, and it was not. CRC2631 and VNP20009 treatments triggered comparable cytokine responses in TRAMP B6FVB mice (FIG. 2I-FIG. 2J).

Bacteria are cleared out of the blood circulation via the liver. VNP20009 causes significant liver toxicity. Thus, the impact of CRC2631 on the liver was established using histopathological approaches. Two groups of 31-week-old B6FVB mice (N=4) were treated IP with 4 doses of $2.5 \times 10^7$ CRC2631 or 200 µl PBS (control) at three-day intervals. Liver histological sections were prepared eleven days after treatment initiation (i.e., in 33-week-old animals) and stained with hematoxylin and eosin (H&E). Examination of H&E stained sections by a veterinary pathologist revealed normal hepatic architecture in treated and non-treated mice (Table 2A and Table 2B). Findings not related to CRC2631 administration and interpreted as insignificant included mild, multifocal inflammatory cell (mononuclear and less commonly granulocyte) infiltrates without associated alterations of adjacent hepatocytes. One mouse in the untreated group had sub-massive coagulative necrosis and congestion of the caudate liver lobe, but this was interpreted to be an incidental lesion and not attributable to treatment group. These analyses were extended to lungs, kidneys, and lymph nodes, and no CRC2631-related tissue anomalies were found (Table 2A and Table 2B). Thus, it was concluded that CRC2361 does not cause liver disease and, more broadly, it does not destroy non-targeted host tissues. Table 2A and Table 2B are shown below for ease of reference. They show a histopathological analysis of non-targeted tissues in CRC2631 administered B6FVB TRAMP(+) mice. Histopathological analysis was performed on samples obtained at necropsy from groups (N=4) of 33-week-old B6FVB TRAMP(+) males to examine the effects of CRC2631 administration on non-targeted tissues. Groups were injected intraperitoneally with PBS (no treatment; Table 2A) control or $2.5 \times 10^7$ CRC2631 (treatment; Table 2B) to examine the effects of CRC2631 administration on non-targeted tissues. Kidneys, liver, lung, and lymph node tissues were collected, mounted on glass slides and stained with hematoxylin and eosin (H&E) for histopathologic examinations by light microscopy.

TABLE 2A

| No Treatment Group: B6FVP TRAMP Mice, Four Doses PBS (3 Day Intervals) | | |
|---|---|---|
| Tissue | Gross Observations | H&E Stain Observations |
| Animal ID: AF5963 | | |
| Right kidney | | Mild peripelvic and perivascular mononuclear cell infiltrate |
| Right renal lymph node | Mildly enlarged | Moderate central necrosis and infiltration by cancer cells (50% visible tissue necrosis in section) |
| Liver (caudate lobes) | Dark red | 80% of tissue has parenchymal necrosis (largely sparing portal triads), marked congestion |

TABLE 2A-continued

| No Treatment Group: B6FVP TRAMP Mice, Four Doses PBS (3 Day Intervals) | | |
|---|---|---|
| Tissue | Gross Observations | H&E Stain Observations |
| Liver | | Mild, multifocal mononuclear cell infiltrate, granulocytic cell infiltrates |
| Left kidney | | Several peripelvic foci of cancer cells |
| Left renal lymph node | Mildly enlarged | Cancer cell infiltration, marked central necrosis (70% visible tissue necrosis in section) |
| Left lumbar aortic lymph node | Moderately enlarged | Cancer cell infiltration |
| Lungs | | Several small cancer foci |
| Animal ID: KQ2130 | | |
| Left kidney | | Mild focal peripelvic mononuclear cell infiltrate |
| Liver | | Very mild multifocal mononuclear cell infiltrate |
| Lungs | | Large focus of cancer cells adherent to large vessel endothelium |

TABLE 2A-continued

| No Treatment Group: B6FVP TRAMP Mice, Four Doses PBS (3 Day Intervals) | | |
|---|---|---|
| Tissue | Gross Observations | H&E Stain Observations |
| Animal ID: PV3912 | | |
| Right kidney | | Focus of peripelvic mononuclear cells |
| Liver | | Rare mononuclear cell infiltrate |
| Left kidney | | Moderate peripelvic mononuclear cellular infiltrate |
| Animal ID: AF5965 | | |
| Right kidney | | Mild to moderate perivascular and peripelvic mononuclear cell infiltrate |
| Lumbar aortic or iliac lymph node | Moderately enlarged | Infiltration by cancer cells (10% visible tissue necrosis in section) |
| Liver | | Mild mononuclear cell infiltrate |
| Left kidney | | Mild peripelvic mononuclear cell infiltrate |

TABLE 2B

| Treatment Group: B6FVB TRAMP Mice, Four Doses $2.5 \times 10^7$ CRC2631 (3 Day Intervals) | | |
|---|---|---|
| Tissue | Gross Observations | H&E Stain Observations |
| Animal ID: FK8038 | | |
| Right kidney | | Mild multifocal peripelvic and perivascular mononuclear cell infiltrates |
| Left kidney | | Mild multifocal peripelvic and perivascular mononuclear cell infiltrates |
| Mesenteric lymph node | Mildly enlarged | Mild hyperplasia |
| Liver | | Mild multifocal granulopoesis, mild multifocal mononuclear cell infiltrate |
| Lungs | | Several foci of cancer cells |
| Animal ID: PV3915 | | |
| Right kidney | | Several foci of cancer cells near pelvis and perivascular, moderate hydronephrosis, mild peripelvic mononuclear cell infiltrate |
| Right renal lymph node | Markedly enlarged | Cancer cells, 10% of visible tissue necrosis in section |
| Liver | Cellular material/fibrin, necrotic debris between liver and GI tract. Possible reactive mesothelial cells. | Moderate multifocal mononuclear cell infiltrate, mild multifocal granulocytic cell infiltrates, mild multifocal granulopoesis |
| Animal ID: FK8027 | | |
| Left kidney | | Multifocal mononuclear cell infiltrate near pelvis |
| Right axillary or accessory lymph node | Markedly enlarged | Cellular infiltrate appears to be 100% cancer cells (5% visible tissue necrosis in section) |
| Right renal lymph node | Mildly enlarged | Cellular infiltrate (100% cancer cells) |

TABLE 2B-continued

| | Treatment Group: B6FVB TRAMP Mice, Four Doses 2.5 × 10^7 CRC2631 (3 Day Intervals) | |
|---|---|---|
| Tissue | Gross Observations | H&E Stain Observations |
| Liver | | Mild multifocal granulopoesis, mild multifocal mononuclear cell infiltrate/granulocytic cell infiltrates |
| Cranial mediastinal lymph node | Moderately enlarged | Mild to moderate hyperplasia, possible focus of cancer cells |
| Lung | | Focus of cancer cells |
| | Animal ID: KQ2133 | |
| Subiliac lymph node | Moderately enlarged | Moderate hyperplasia |
| Right kidney | | Mild focal peripelvic cellular infiltrate |
| Liver | | Mild to moderate multifocal perivascular and periportal cellular infiltrate, mild multifocal mononuclear cell infiltrate/granulocytic cell infiltrates |
| Lungs | | No significant lesions; cancer in bronchiolar epithelium. |

Example 3. CRC2631 Preferentially Colonizes Primary Tumors and Metastases

Next, it was sought to determine the in vivo tumor-targeting capability of CRC2631 in TRAMP animals.

First, a strategy was devised that not only permitted longitudinal detection of CRC2631 in live-treated animals using fluorescence imaging but also made it possible to selectively isolate CRC2631 from harvested organs for quantitative bio-distribution assays.

The fluorescence reporter iRFP720 and a chloramphenicol resistance cassette were introduced into CRC2631, generating CRC2631$^{iRFP720-cat}$. The kanamycin resistance cassette inserted into the ΔthyA deletion site was replaced with a gene fusion that constitutively expresses the iRFP720 fluorescent protein (Shcherbakova, D. M. and V. V. Verkhusha (2013). "Near-infrared fluorescent proteins for multicolor in vivo imaging." Nat Methods 10 (8): 751-754.) and the cat chloramphenicol resistance cassette (FIG. 3A). In comparison to CRC2631, CRC2631$^{iRFP720-cat}$ produced visible iRFP720 fluorescence signal and grew in chloramphenicol media, making it suitable for in vivo tumor-targeting studies.

Two groups (N=3) of B6FVB TRAMP(+) animals were scanned by MRI to establish tumor burden. All of the B6FVB TRAMP(+) animals exhibited prostate tumors and metastases to various visceral organs (FIG. 3K-FIG. 3V); one animal had several metastatic masses in the peritoneal cavity (FIG. 3S-FIG. 3T). To determine CRC2631$^{iRFP720-cat}$ tumor-targeting capabilities, these animals received IV injections of 10^7 or 2.5×10^7 CFU of CRC2631$^{iRFP720-cat}$. One additional B6FVB mouse was included in each dose group (AK5290 and KT6638 for the 10^7 and 2.5×10^7 CFU groups, respectively) as a fluorescence background control.

First RC2631$^{iRFP720-cat}$ bio-distribution was determined at 96 hours and 190 hours post injection (hpi) by detecting the iRFP signal of CRC2631$^{iRFP720-cat}$ at the indicated time-points using the fluorescence in vivo imaging system (IVIS). In both dosage groups, iRFP signals were detected above background in two of the three animals treated with CRC2631$^{iRFP720-cat}$. High intensity iRFP foci were detected in the prostate and peritoneal cavity regions at 96 hpi (FIG. 3B-FIG. 3C). These signals coincided with the positions of primary and metastatic legions in from MRI images and persisted for over three days (190 hpi) (FIG. 3G-FIG. 3H), suggesting that CRC2631$^{iRFP720-cat}$ preferentially colonized tumor tissues.

To confirm this, CRC2631$^{iRFP720-cat}$ load was determined in tumor tissues (prostate and bulk metastases), blood, lung, lymph nodes, liver, spleen, and kidneys harvested from the 190 hpi animals above (detection thresholds for the aforementioned tissues were 6.58×10^1, 1×10^3, 6.73×10^3, 4.86× 10^4, 2.63×10^2, 9.69×10^3, and 4.70×10^2 CRC2631$^{iRFP720-cat}$ counts per gram tissue, respectively). The indicated tissues were harvested and their respective counts of CRC2631$^{iRFP720-cat}$ per gram of tissue were determined under chloramphenicol selection (see Example 1).

Detectable CRC2631$^{iRFP720-cat}$ was enriched in the prostate at the 10^7 and 2.5×10^7 CFU dosing levels (FIG. 3D-FIG. 3F, FIG. 3I-FIG. 3J). Two out of three animals in the 10^7 CFU group had detectable colonies only from the prostate and liver tissues. One animal in the 2.5×10^7 CFU group (i.e., QA2140) did not yield any colony in the analyzed tissues; however, the remaining two animals (VF2749 and AK5289) showed higher colony counts in the prostate and bulk metastases compared to the remaining tissues (FIG. 3I-FIG. 3J). No detectable CRC2631$^{iRFP720-cat}$ counts were present in whole blood. Comparing bacterial load in the liver versus in tumor tissues provides a measure of tumor-targeted bacterial colonization. The prostate to liver ratio of CRC2631$^{iRFP720-cat}$ counts ranged from 20:1 to 18000:1 and 1220:1 to 1690:1 in the 10^7 CFU and 2.5×10^7 CFU treated animals, respectively (FIG. 3D-FIG. 3F, FIG. 3I-FIG. 3J). Two (VF2749 and AK5289) of the three animals in the 2.5×10^7 CFU dose group exhibited several prominent metastases (FIG. 3S-FIG. 3U) and the metastases to liver CRC2631$^{iRFP720-cat}$ count ratio ranged from 1640:1 to 2990:1 (FIG. 3I-FIG. 3J). Taken together, these data indicate that CRC2631$^{iRFP720-cat}$ targets primary tumors and metastases.

Example 4. CRC2631 is Genetically Stable Inside the Host

The genetic alterations that attenuate CRC2631 and contribute to its tumor-targeting capability are permanently integrated in its genome. This reduces the likelihood that CRC2631 will regain toxicity and/or lose its tumor targeting capability due to de novo mutations inside the host environment; however, it remained a possibility. To determine the genetic stability of CRC2631 inside the host, longitudinal whole genome sequencing and short nucleotide polymorphism (SNP) analyses of CRC2631 were performed prior to treatment and tumor-passaged CRC2631 in B6 TRAMP(+) mice. Animals (N=4) were treated intravenously with CRC2631 ($2.5 \times 10^7$ CFU), and then CRC2631 was isolated from prostate tissues harvested at 96 or 190 hpi. Three isolates were recovered from the 96 hpi (CRC2631a-c), and one isolate was recovered from the 190 hpi (CRC2631d) prostate tissues (Table 3). Genomic DNA libraries were produced for all samples and sequenced using NovaSeq® 2×100 lane kit protocols (Illumina®). SNPs identified in reads assembled and mapped against the CRC2631 parental LT2 (NCBI: NC_003197.2) and associated stable pSLT plasmid (NCBI: NC_003277.2) sequences using breSeq (v0.53.1), freeBayes (v1.3.2) and TIDDIT (v2.10.0) to identify SNP mutations and structural variations present in the tumor-passaged strains (CRC2631a-d) but not in the CRC2631 injection strain. "0/0" indicates no mutation in daughter strain compared to CRC2631 injection strain; "0/1" indicates a SNP mutation in daughter strain compared to CRC2631 injection strain; "1/1" indicates a SNP mutation in CRC2631 daughter strain that reverts back to the original LT2 sequence compared to CRC2631 injection strain. Table 3 indicating mutations is shown below for reference.

(CCTGTT) in an intragenic region between pSLT064 and ssbB of the LT2-associated plasmid (pSLT) (FIG. 4C).

The observed low SNP frequency in tissue-passaged CRC2631 over an ~8 day period suggested that CRC2631 is genetically stable within the host. To evaluate the robustness of CRC2631 genetic stability, the time it would take for CRC2631 to experience a SNP in any gene of interest was first estimated. The LT2 lineage of the CRC2631 genome (including the stably associated pSLT plasmid) consisted of ~4951383 base pairs organized in ~4548 predicted gene coding sequences. The average size of the gene coding sequences is 943.89 bp (McClelland, M., K. E. Sanderson, et al. (2001). "Complete genome sequence of *Salmonella enterica* serovar *Typhimurium* LT2." *Nature* 413 (6858): 852-856.). Considering the observed SNP frequency rate (51.83±7.67 hours/SNP), it would take ~9375 days for CRC2631 to acquire a SNP in any specific gene by chance. In a complementary approach, the risk probabilities of such an event over time was modeled (see Example 1). This model predicted that the probability of an average gene accumulating a first SNP after 10, 100, 1000, 10000 and 100000 days to be: 0.0015, 0.01, 0.0921, 0.6181, and 0.9999, respectively (FIG. 4D). The probability that CRC2631 will gain 0, 1, 2, 3, 4, and 5 mutations four days after treatment is predicted to be 0.21, 0.29, 0.23, 0.14, 0.07, and 0.03, respectively. Thus, CRC2631 is a stable tumor-targeting biologic.

Example 5. CRC2631 Reduces Metastatic Incidence in Combination with Immunotherapies Like Checkpoint Blockade Therapies The observations that CRC2631 stably colonized tumors, including metastases, prompted exploration of the possibil-

TABLE 3

| Reference Genome | SNP Position (Gene) | (96hpi) CRC2631a | (96hpi) CRC2631b | (96hpi) CRC2631c | (190hpi) CRC2631d |
|---|---|---|---|---|---|
| NC_0031972 | 1110887 (STM1021) | 0/1 | 0/1 | 0/1 | 0/1 |
| NC_0031972 | 1111253 (STM1021) | 0/1 | 0/1 | 0/1 | 0/1 |
| NC_0032772 | 53704 (intragenic) | 0/0 | 0/0 | 0/0 | 1/1 |

DNA was isolated and Illumina® Next Generation Sequencing (NGS) was performed on 0 hpi CRC2631 (prior to treatment) and all tumor-passaged isolates to identify SNP mutations occurring in the host environment. Comparisons of the 96 hpi or 190 hpi versus the 0 hpi sequences identified a total of two and three SNPs at 96 hpi and 190 hpi, respectively. The three 190 hpi SNPs include the same two SNPs identified at 96 hpi. To map these SNPs to specific genes, genome information from the *Salmonella enterica* serovar *Typhimurium* LT2 strain (GenBank®: AE006468.2) and its associated pSLT plasmid (GenBank®: AE006471.2) was annotated. There is no annotated genome information currently available for CRC2631, and CRC2631 is a direct derivative of LT2. With the exception of one SNP that mapped to an intergenic region, all of the remaining variants represented synonymous SNPs. The two 96 hpi SNPs mapped to two distinct positions in the STM1021 locus, which is similar to the Gifsy-2 lysogenic bacteriophage region (ninG) in the LT2 genome (FIG. 4A-FIG. 4B). The unique 190 hpi SNP consisted of a six base-pairs deletion ity that CRC2631 reduces tumor burden in TRAMP animals. The inventors previously reported that low doses of CRC2631 ($10^7$ CFU administered weekly) modestly reduced prostate tumor size in TRAMP animals (Kazmierczak, R. A., B. Gentry, T. Mumm, H. Schatten and A. Eisenstark (2016). "*Salmonella* Bacterial Monotherapy Reduces Autochthonous Prostate Tumor Burden in the TRAMP Mouse Model." *PLOS One* 11(8): e0160926.). The first line of inquiry was whether CRC2631 generates a more robust therapeutic response at a higher CRC2631 dose. Pre- and post-treatment MRI images were used to compare tumor size in response to therapy. Groups (N=12) of 8-10-week-old B6FVB TRAMP(+) animals were treated with PBS (control) or $2.5 \times 10^7$ CFU CRC2631 administered intravenously every three days for a total of four treatments. Prostate tumor size was scored in control versus CRC2631-treated animals 21 days after treatment initiation, and CRC2631 did not significantly reduce prostate tumor size, compared to the PBS control (FIG. 5A; p<0.6799, 30.77 mm³±76.07 versus 42.30 mm³±52.79 respectively). CRC2631 targeted and directly killed murine and human prostate cancer cells in vitro (FIG. 6), raising the possibility that unknown resistance mechanisms protect tumor cells from CRC2631-mediated cell death in vivo. These inhibitory signals may be tumor cell-intrinsic and/or involve the tumor immune microenvironment.

Tumor-localized CRC2631 failed to reduce the size of primary prostate tumors in TRAMP animals. This could be due to a sub-optimal intra-tumoral CRC2631 load; a higher and safe dosing regimen and/or direct intra-tumoral CRC2631 delivery could be used. This result also could be due to the aggressiveness of the TRAMP model. In contrast to mouse cancer models where oncogenesis is triggered in a limited number of cells over a defined time interval, androgen-driven expression of SV40 antigens transforms prostatic tissues more broadly and continuously, leading to sustained and rapid tumor overgrowth. This may potentially mask a CRC2631 tumor suppressive effect. Prostate cancers progress more slowly in human patients. It is contemplated that the evaluation of CRC2631 therapeutic profile to other tumor models would be informative.

Concerning an interaction between CRC2631 and immune cells, the next line of inquiry was whether tumor-targeted CRC2631 generates an anti-tumor immune response that tumors rapidly inhibit via immune checkpoint mechanisms. Tumor cells express program death ligand-1 (PDL1), which interacts with PD1 on the surface of immune T-cells to inhibit anti-tumor immune activities.

RNA sequencing data showed an upregulation of immunogenic chemokines and cytokines (CXCL, CSF2, IL6, and TNF) in human prostate cancer cells (PC3, PC3M) or mice treated with CRC2631 (FIG. 5B and FIG. 2I-FIG. 2J, respectively). Similar to humans, TRAMP animals develop a robust immunosuppressive microenvironment in prostate tumors, which were thought to likely mask the effect of CRC2631. Thus, distant metastases were focused on to determine whether metastases-targeted CRC2631 recruits and activates tumor-infiltrating lymphocytes (TILs) in vivo. TRAMP animals develop unambiguous lymph node and visceral organ metastases that can be readily detected in MRI images (FIG. 3K-FIG. 3V). Lymph nodes containing MRI-verified metastases were harvested either from CRC2631-treated or PBS control TRAMP animals. Flow cytometric analyses showed that CRC2631 significantly elevated the frequency of activated CD4$^+$ (CD69$^+$/CD4$^+$) TILs in metastasized lymph node tissues (FIG. 5C). CD4$^+$ TILs mediate an anti-cancer immune response by activating tumoricidal CD8$^+$ T-cells. In contrast, regulatory T-cells (T$_{reg}$) suppress CD8$^+$ T-cells. CRC2631 treatment did not enhance T$_{reg}$ frequency compared to PBS control tissues. Interestingly, histological analyses did not show an increase of CD8$^+$ TILs in metastasized lymph nodes or lungs derived from the therapy animals compared to controls, suggesting T-cell exhaustion. Congruently, CRC2631 increased the proportion of CD4$^+$ TILs expressing the exhaustion marker PD1 (CD4$^+$ PD1$^+$) (FIG. 5D). Targeted inhibition of the PDL1-PD1 signaling axis restores anti-cancer immune activity and generates significant clinical benefits in patients with immunogenic cancers. The observations of the present disclosure suggest that CRC2631 may reduce tumor burden by enabling an anti-tumor immune response in the PDL1/PD1 blockade setting.

Eight-to-ten-week old animals (N=12) were scanned by MRI to control for tumor burden across groups. These animals were treated with 200 µL of PBS (vehicle control) or CRC2631 (2.5×10$^7$ CFU) or murine anti-PDL1 antibodies (Invivomab®, 0.5 mg) or a cocktail of CRC2631-Invivomab®. The dosing regimen consisted of a single dose of the indicated treatment every three days for a total of four infusions. Twelve to fourteen weeks after the last infusion animals received a single boost dose. Post-treatment lung and lymph node MRI images were used to enumerate and compare metastasis incidence across groups at 21 days after treatment (FIG. 5E-FIG. 5F). PBS control animals showed an average of 1.83±0.389 and 1.33±0.985 metastases in proper axial lymph nodes and lungs, respectively. Alone, CRC2631 or Invivomab® treatments did not significantly reduce metastasis to the lymph nodes or the lung. In contrast, the CRC2631-Invivomab® combination treatment reduced metastasis incidences in lymph nodes and the lung. CRC2631-Invivomab® averaged 1.27±1.01 proper axial lymph node metastatic incidences after 21 days compared to 1.83±0.577 in CRC2631 and 1.92±0.289 in Invivomab® alone. In the lung, CRC2631-Invivomab® showed an average of 0.727±0.786 metastases compared to 1.50±0.522 in CRC2631 and 1.75±1.06 in Invivomab® alone. Thus, CRC2631-checkpoint blockade combination treatment reduced metastatic burden.

Example 6. CRC2631 Exhibits Advantageous Properties in Combination with Chemotherapies and Androgen Receptor Antagonist Therapies Hyper activation of androgen signaling causes prostatic carcinomas (PCa), which progress into neuroendocrine prostate cancer (NEPC), a highly lethal subtype. Taxane-based chemotherapies and androgen deprivation therapy (ADT) are cornerstone treatments against prostate cancer. However, chemotherapies are non-specific and cause significant morbidity. ADT is comparatively better tolerated but it is largely ineffective, especially in patients with NEPC. Nearly all ADT treated patients eventually relapse and succumb to the disease months following treatment initiation. This underscores the need for novel targeted therapies that durably destroy prostate cancers, including NEPC.

The present disclosure is directed to an engineered *Salmonella typhimurium* bacterial strain (CRC2631) that specifically colonizes prostate tumor tissues and reduces metastasis burden at sub toxic levels in a murine model of NEPC (TRAMP). Importantly, transcriptomic and signaling pathway analyses have identified rationally selected combination treatments to achieve maximal cancer cell killing. Here it is shown that combining CRC2631 with chemotherapeutics (Birinipant or Docetaxel) or with hormone therapies (Enzalutamide) generates advantageous cell killing effects on PCa and NEPC cells.

Prostate adenocarcinomas are androgen sensitive. NEPCs commonly arise after hormonal therapy for prostate adenocarcinoma and are not androgen responsive. CRC2631's ability to target and destroy human prostate cancer cells was evaluated using a cell viability assay. Cell lines representing androgen-sensitive adenocarcinomas (LnCAP), androgen-insensitive carcinomas (PC3 and PC3M) and NEPC (NCI-H660) stages of prostate cancer were tested. CRC2631 treatment selectively targeted prostate cancer cells including NEPCs (NCI-H660) (FIG. 9A). CRC2631 did not exhibit any effect on benign prostate cells. Thus, CRC2631 specifically kills androgen-insensitive (PC3M) cells, but it is less effective against the fully differentiated NEPC (H660) cancer cells.

The transcriptional changes of human prostate cancer cells (PC3, PC3M) in response to CRC2631 (treated compared to non-treated) were examined. Both these cell lines are AR-negative, similar to NEPC cells. To identify transcriptional programs that are unique to prostate cancer (PC) cells, genes that were also differentially expressed in CRC2631-treated benign prostate cells (RWPE-1) were filtered out. Genes-pathways analyses led to the identification of the cellular Inhibitor of Apoptosis (cIAP) as a potential target. Birninapant is a safe peptidomimetic that binds to and inhibits the activity of IAPs. LnCAP (adenocarcinoma, AR sensitive), PC3M and NCI-H660 cells were treated with birinapant and CRC2631 alone or together to test a Birinapant-CRC2631 combination effect. The CRC2631-birinapant combination selectively and reproducibly killed prostate cancer (PC3M) cells and NCI-H660 (NEPC cells) with higher potency than either agent alone in vitro (FIG. 9B). Thus, CRC2631-Birninapant combination treatment has a therapeutic advantage over either treatment alone.

Docetaxel is the standard chemotherapeutic for prostate cancer. The cell killing capacity of CRC2631 was tested against PCa and NEPCs. The cell viability of prostate cells pre-treated with docetaxel followed by CRC2631 was tested. The result was that CRC2631 in combination with docetaxel (DOX) significantly reduces the viability of resistant NEPC (H660) (FIG. 9C). Thus, CRC2631-Docetaxel combination treatment has a therapeutic advantage over either treatment alone.

Furthermore, it was tested if CRC2631 would exhibit advantageous properties when in combination with the standard androgen deprivation therapy for prostate cancer (Enzalutamide). Susceptibility of PCa and NEPC cells pre-treated with enzalutamide (AZT) towards CRC2631 was tested. A cell viability assay indicated that CRC2631-enzalutamide combination advantageously killed NEPC (NCI-H660) cells (FIG. 9D).

Example 7. CRC2631 Also Targets and Restrains Pancreatic Cancer Tumors

In addition to determining the effects of CRC2631 on prostate cancer, its effects on pancreatic cancer were also examined.

First, the ability of CRC2631 to target pancreatic cancer tumors was shown. Groups (N=15) of tumor free (BL6) animals or animals carrying metastatic pancreatic cancer (B6Panc02H7) were treated intravenously with saline control (PBS) or iRFP-labeled CRC2631, with in vivo fluorescence imaging occurring 4 days after treatment to assess the CRC2631 biodistribution. CRC2631-iRFP signals were enriched in tumor-bearing B6Panc02H7 mice (FIG. 10A). Much less CRC2631 was detected in tumor-free BL6 animals (right-most animal) where signals were slightly above background (first and second animals from the left). Similarly, pancreatic cryosectioned tumor tissue obtained from tumor-bearing animals showed an enrichment of CRC2631$^{iRFP720-cat}$ fluorescence compared to tumor-free controls (FIG. 10B-FIG. 10C). Thus, CRC2631 localizes to pancreatic tumors.

Next, whether this pancreatic tumor targeted CRC2631 could reduce tumor size was determined. Tumors were harvested from PBS (control) or CRC2631$^{iRFP720-cat}$-treated animals and weighed to determine the effect of CRC2631 on tumor size. Both doses of CRC2631$^{iRFP720-cat}$ treatment caused a reduction in tumor size by weight (FIG. 10D), demonstrating that CRC2631 helps reduce tumor size in pancreatic cancer.

The effects of CRC2631 treatment on the life span of pancreatic cancer model mice were tested. B6PanC02H7 animals (N=6/group) were treated with saline (PBS), 2.5× $10^7$ CFU of CRC2631, or 5×$10^7$ CFU of CRC2631. Kaplan Meyer survival analyses were performed. No treatment-related animal lethality was observed. Instead, CRC2631-treated animals lived longer than controls (FIG. 10E). Thus, CRC2631 can increase life span in a pancreatic cancer mouse model.

The final experiment was to determine if CRC2531 induces an immune response in a pancreatic cancer mouse model. Immune response was measured as the percentage of CD69+/CD8+ cells for no treatment (NT) control B6Panc02H7 mice and CRC2631$^{iRFP720-cat}$ treated B6Panc02H7 mice. The results demonstrate that tumor-localized CRC2631$^{iRFP720-cat}$ activates anti-tumor CD8$^+$ immune cells in the spleen (FIG. 11), suggesting immune-mediated anti-cancer activity in this pancreatic cancer model.

---

SEQUENCE LISTING

The patent contains a lengthy sequence listing. A copy of the sequence listing is available in electronic form from the USPTO web site (https://seqdata.uspto.gov/docdetail?docId=US12648970B2). An electronic copy of the sequence listing will also be available from the USPTO upon request and payment of the fee set forth in 37 CFR 1.19(b)(3).

---

The invention claimed is:

1. A method for treating cancer in a patient in need thereof, the method comprising administering an effective amount of a biologically pure isolate of the genus *Salmonella* comprising archival strain CRC1674, wherein the isolate further comprises a disruption of at least one gene selected from the group consisting of aroA gene, rfaH gene, and thyA gene, and an agent of (i) a chemotherapy agent, (ii) an immunotherapy agent, or (iii) a chemotherapy and immunotherapy agent.

2. The method of claim 1, wherein the agent is the immunotherapy agent and comprises an immune checkpoint inhibitor.

3. The method of claim 2, wherein the immune checkpoint inhibitor comprises Atezolizumab, Avelumab, Durvalumab, Pembrolizumab, Nivolumab, Invivomab, Ipilimumab, or a combination thereof.

4. The method of claim 3, wherein the cancer is a solid tumor.

5. The method of claim 3, wherein the cancer is pancreatic cancer or prostate cancer.

6. A method for treating prostate cancer in a patient in need thereof, the method comprising administering an effective amount of a biologically pure isolate of the genus *Salmonella* comprising archival strain CRC1674, wherein the isolate further comprises a disruption of at least one gene selected from the group consisting of aroA gene, rfaH gene, and thyA gene and an agent of (i) a chemotherapy agent, (ii) an androgen receptor antagonist, or (iii) a chemotherapy agent and androgen receptor antagonist.

7. The method of claim 6, wherein the agent is the androgen receptor antagonist comprising bicalutamide, flutamide, enzalutamide, abiraterone, or a combination thereof.

8. The method of claim 7, wherein the cancer is a metastatic cancer.

9. The method of claim 7, wherein the administration is via intravenous injection.

10. The method of claim 1, wherein the effective amount of the isolate is at or below the clinically determined maximum tolerated dose.

11. The method of claim 1, wherein CRC2631 in combination with the chemotherapy agent, immunotherapy agent, androgen receptor antagonist, or combination thereof kills cancer cells more efficiently than CRC2631, chemotherapy agent, immunotherapy agent, or androgen receptor antagonist alone.

12. The method of claim 1, wherein the patient is a human.

13. The method of claim 1, wherein the agent is the chemotherapy agent and comprises birinipant, cabazitaxel, docetaxel, paclitaxel, mitoxantrone, carboplatin, vinorelbine, oftamoxifen, raloxifene, anastrozole, exemestane letrozole, imatanib, cyclophosphamide, lovastatin, minosine, gemcitabine, cytarabine, 5-fluorouracil, methotrexate, gosereline, vincristine, vinblastine, nocodazole, teniposide, etoposide, epithilone, vinorelbine, captothecin, daunorubicin, actinomycin D, mitoxantrone, acridine, doxorubicin, epirubicin, or idarubicin.

14. The method of claim 7, wherein the androgen receptor antagonist comprises enzalutamide.

15. The method of claim 13, wherein the chemotherapy agent comprises birinipant, docetaxel, or a combination thereof.

16. The method of claim 2, wherein the immune checkpoint inhibitor comprises Invivomab.

17. The method of claim 6, wherein the agent is the chemotherapy agent and comprises birinipant, cabazitaxel, docetaxel, paclitaxel, mitoxantrone, carboplatin, vinorelbine, oftamoxifen, raloxifene, anastrozole, exemestane letrozole, imatanib, cyclophosphamide, lovastatin, minosine, gemcitabine, cytarabine, 5-fluorouracil, methotrexate, gosereline, vincristine, vinblastine, nocodazole, teniposide, etoposide, epithilone, vinorelbine, captothecin, daunorubicin, actinomycin D, mitoxantrone, acridine, doxorubicin, epirubicin, or idarubicin.

18. The method of claim 17, wherein the chemotherapy agent comprises birinipant, docetaxel, or a combination thereof.

19. The method of claim 3, wherein the agent is the chemotherapy agent and androgen receptor antagonist, wherein the chemotherapy agent comprises birinipant, cabazitaxel, docetaxel, paclitaxel, mitoxantrone, carboplatin, vinorelbine, oftamoxifen, raloxifene, anastrozole, exemestane letrozole, imatanib, cyclophosphamide, lovastatin, minosine, gemcitabine, cytarabine, 5-fluorouracil, methotrexate, gosereline, vincristine, vinblastine, nocodazole, teniposide, etoposide, epithilone, vinorelbine, captothecin, daunorubicin, actinomycin D, mitoxantrone, acridine, doxorubicin, epirubicin, or idarubicin.

20. The method of claim 7, wherein the agent is the chemotherapy agent and androgen receptor antagonist, wherein the chemotherapy agent comprises birinipant, cabazitaxel, docetaxel, paclitaxel, mitoxantrone, carboplatin, vinorelbine, oftamoxifen, raloxifene, anastrozole, exemestane letrozole, imatanib, cyclophosphamide, lovastatin, minosine, gemcitabine, cytarabine, 5-fluorouracil, methotrexate, gosereline, vincristine, vinblastine, nocodazole, teniposide, etoposide, epithilone, vinorelbine, captothecin, daunorubicin, actinomycin D, mitoxantrone, acridine, doxorubicin, epirubicin, or idarubicin.

* * * * *